US011135282B2

(12) United States Patent
Marasco

(10) Patent No.: US 11,135,282 B2
(45) Date of Patent: Oct. 5, 2021

(54) HUMANIZED INFLUENZA MONOCLONAL ANTIBODIES AND METHODS OF USE THEREOF

(71) Applicant: Dana-Farber Cancer Institute, Inc., Boston, MA (US)

(72) Inventor: Wayne A. Marasco, Wellesley, MA (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 0 days.

(21) Appl. No.: 15/564,897

(22) PCT Filed: Apr. 8, 2016

(86) PCT No.: PCT/US2016/026800
§ 371 (c)(1),
(2) Date: Oct. 6, 2017

(87) PCT Pub. No.: WO2016/164835
PCT Pub. Date: Oct. 13, 2016

(65) Prior Publication Data
US 2018/0099040 A1 Apr. 12, 2018

Related U.S. Application Data

(60) Provisional application No. 62/144,729, filed on Apr. 8, 2015.

(51) Int. Cl.
C07K 16/28 (2006.01)
C07K 16/46 (2006.01)
A61K 39/145 (2006.01)
C07K 16/10 (2006.01)
A61P 31/16 (2006.01)
A61K 39/00 (2006.01)

(52) U.S. Cl.
CPC ............ A61K 39/145 (2013.01); A61P 31/16 (2018.01); C07K 16/1018 (2013.01); A61K 2039/505 (2013.01); C07K 2317/21 (2013.01); C07K 2317/33 (2013.01); C07K 2317/34 (2013.01); C07K 2317/565 (2013.01); C07K 2317/732 (2013.01); C07K 2317/76 (2013.01); C07K 2317/92 (2013.01)

(58) Field of Classification Search
None
See application file for complete search history.

(56) References Cited

U.S. PATENT DOCUMENTS

| 3,773,919 A | 11/1973 | Boswell et al. |
| 4,485,045 A | 11/1984 | Regen |
| 4,522,811 A | 6/1985 | Eppstein et al. |
| 4,544,545 A | 10/1985 | Ryan et al. |
| 4,676,980 A | 6/1987 | Segal et al. |
| 4,816,567 A | 3/1989 | Cabilly et al. |
| 4,946,778 A | 8/1990 | Ladner et al. |
| 5,013,556 A | 5/1991 | Woodle et al. |
| 5,030,719 A | 7/1991 | Umemoto et al. |
| 5,091,513 A | 2/1992 | Huston et al. |
| 5,132,405 A | 7/1992 | Huston et al. |
| 5,223,409 A | 6/1993 | Ladner et al. |
| 5,545,806 A | 8/1996 | Lonberg et al. |
| 5,545,807 A | 8/1996 | Surani et al. |
| 5,569,825 A | 10/1996 | Lonberg et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,916,771 A | 6/1999 | Hori et al. |
| 5,939,598 A | 8/1999 | Kucherlapati et al. |
| 2012/0058124 A1 | 3/2012 | Kurosawa |
| 2013/0302349 A1 | 11/2013 | Shriver |

FOREIGN PATENT DOCUMENTS

| WO | 91/00360 | 1/1991 |
| WO | 1992/020373 | 11/1992 |
| WO | 94/02602 | 2/1994 |
| WO | 94/11026 | 5/1994 |
| WO | 95/22618 | 8/1995 |
| WO | 96/33735 | 10/1996 |
| WO | 96/34096 | 10/1996 |
| WO | 99/53049 | 10/1999 |
| WO | 2010130636 A1 | 11/2010 |
| WO | 2011117848 A1 | 3/2012 |
| WO | 2013007770 A1 | 1/2013 |

(Continued)

OTHER PUBLICATIONS

McLean et al. (Molecular Immunology, 2006, p. 2012-2022).*
Fu et al. (Nature Communications, 2016, p. 1-13).*
Kohler and Milstein, Nature, 256:495 (1975).
Kozbor, et al., 1983 Immunol Today 4:72.
Kozbor, J. Immunol., 133:3001 (1984).
Lam, 1991. Nature 354:82-84.
Lam, 1997 Anticancer Drug Design 12:145.
Lanza et al., Proc. Natl. Acad. Sci. USA 90:11683-87 (1993).
LeGal LaSalle et al., Science, 259:988 (1993).
Lim, F., et al., in DNA Cloning: Mammaliam Systems, D. Gover, Ed. (Oxford Univ. Press, Oxford England) 1995.
Lonberg and Huszar, Intern. Rev. Immunol. 13 65-93 (1995).

(Continued)

Primary Examiner — Agnieszka Boesen
(74) Attorney, Agent, or Firm — Baker Donelson

(57) ABSTRACT

The present invention provides structural determinants important for binding to the stem domain of the HA protein of influenza virus, and methods of use thereof for production of high affinity neutralizing influenza virus antibodies based upon these determinants. The present invention further provides tools for determining the efficacy of an influenza virus vaccine. The present invention further provides a molecular signature useful for determining the efficacy of an influenza virus vaccine in a subject, or for predicting prior immunologic exposure or antigen responsiveness to vaccine or influenza virus infection.

10 Claims, 42 Drawing Sheets
Specification includes a Sequence Listing.

(56) References Cited

FOREIGN PATENT DOCUMENTS

| WO | 2013011347 A1 | 1/2013 |
|---|---|---|
| WO | 2014/078268 A2 | 5/2014 |

OTHER PUBLICATIONS

Lonberg et al., Nature 368 856-859 (1994).
Lunde et al., Biochem. Soc. Trans. 30:500-6 (2002).
Malmqvist, M. Nature 361:186-87 (1993).
Marasco et al., Proc. Natl. Acad. Sci. USA, 90: 7889-7893 (1993).
Marks et al., Bio/Technology 10, 779-783 (1992).
Marks et al., J. Mol. Biol., 222:581 (1991).
Martin et al., J. Biol. Chem., 257: 286-288 (1982).
Matthews et al., J. Immunol. 169:837 (2002).
Morrison et al., Am. J. Physiol. 266:292-305 (1994).
Morrison, Nature 368, 812-13 (1994).
Munson and Pollard, Anal. Biochem., 107:220 (1980).
Neuberger, Nature Biotechnology 14, 826 (1996).
Parren et al., Adv. Immunol. 77:195-262 (2001).
Peptide and Protein Drug Delivery (Advances in Parenteral Sciences, vol. 4), 1991, M. Dekker, New York.
Ramakrishnan, S. et al., Cancer Res. 44:201-208 (1984).
Remington: The Science and Practice of Pharmacy 19th ed. (Alfonso R. Gennaro, et al., editors) Mack Pub. Co., Easton, Pa., 1995.
Scott and Smith, 1990. Science 249:386-390.
Shibata et al., Nat Med. 5:204-10 (1999).
Shopes, J. Immunol., 148: 2918-2922 (1992).
Stevenson et al., Anti-Cancer Drug Design, 3:219-230 (1989).
Steward et al., J. Virol. 69:7668 (1995).
Vitetta et al., Science 238: 1098 (1987).
Yang, et al., J. Virol. 69:2004 (1995).
You et al., Cancer Res. 61:3704-11 (2001).
Zaghouani et al., Proc. Natl. Acad. Sci. USA 92:631-35 (1995).
Zanetti, Nature 355:476-77 (1992).
Zebedee et al., Proc. Natl. Acad. Sci. USA 89:3175-79 (1992).
Zuckermann, et al., 1994. J. Med. Chem. 37:2678.
"Conjugate Vaccines", Contributions to Microbiology and Immunology, J.M. Cruse and R. E. Lewis, Jr (eds), Carger Press, New York (1989).
"ELISA: Theory and Practice: Methods in Molecular Biology" vol. 42, J.R. Crowther (Ed.) Human Press, Totowa, N.J., 1995.
"Immunoassay" E Diamandis and T. Christopoulus, Academic Press, Inc., San Diego, Calif, 1996.
"Practice and Theory of Enzyme Immunoassays" P. Tijssen, Elsevier Science Publishers, Amsterdam, 1985.
Antibodies: A Laboratory Manual, Harlow E. and Land D., 1998, Cold Springs Harbor Laboratory Press, Cold Spring Harbor, N.Y.
Barbas et al., Proc. Natl. Acad. Sci. USA 89:9339-43 (1992).
Bobo et al., Proc. Natl. Acad. Sci. USA 91:2076-2080 (1994).
Bona et al., Immunol. Today 19:126-33 (1998).
Brodeur et al., Monoclonal Antibody Production Techniques and Applications, marcel Dekker, Inc., New York, (1987) pp. 51-63.
Burton, Natl. Rev. Immunol. 2:706-13 (2002).
Carell, et al., 1994. Angew. Che. Int. Ed. Engl. 33:2059.
Carell, et al., 1994. Angew. Chem. Int. Ed. Engl. 33:2061.
Caron et al., J. Exp Med., 176: 1191-1195 (1992).
Casadevall, Nat Biotechnol. 20:114 (2002).
Casares, et al., Viral Immunol. 10:129-36 (1997).
CDC's General Recommendation on Immunization (51(RR02) pp. 1-36.
Cho, et al., 1993. Science 261: 1303.
Cole, et al., 1985 In: Monoclonal Antibodies and Cancer Therapy, Alan R. LIss, Inc., pp. 77-96.
Cote, et al., 1983. Proc Natl Acad Sci USA 80: 2026-2030.
Cull, et al., 1992. Proc. Natl. Acad. Sci. USA 89:1965-1869.
Cwirla, et al., 1990. Proc. Natl. Acad. Sci. USA 87:6378-6382.
D. Wilkinson (The Scientist, published by the Scientist, Inc., Philadelphia Pa., vol. 14, No. 8 (Apr. 17, 2000), pp. 25-28.
Davidson, et al., Nat. Genet 3:219 (1993).
Davies et al. (1990) Annual Rev Biochem 59:439-473.
Devlin, 1990, Science 249:404-406.
DeWitt, et al., 1993. Proc. Natl. Acad. Sci. U.S.A. 90: 6909.
Drug Absorption Enhancement: Concepts, Possibilities, Limitations, and Trends, Harwood Academic Publishers, Langhorne, Pa., 1994.
Epstein et al., Proc. Natl. Acad. Sci. USA, 82: 3688 (1985).
Erb, et al., 1994. Roc. Natl. Acad. Ci. USA 91: 11422.
Felici, 1991. J. Mol. Biol. 222:301-310.
Fishwild et al, Nature Biotechnology 14, 845-51 (1996).
Fodor, 1993. Nature 364:555-556.
Gallop, et al., 1994. J. Med. Chem. 37:1233.
Garrity et al., J. Immunol. 159:279(1997).
Geller, A. I. et al, Proc natl. Acad. Sci: USA 90:7603 (1993).
Geller, A. I. et al., J. Neurochem, 64:487 (1995).
Geller, A. I., et al., Proc Natl. Acad. Sci USA 87:1149 (1990).
Gerloni et al., DNA Cell Biol. 16:611-25 (1997).
Gerloni et al., Nat. Biotech. 15:876-81 (1997).
Goding, Monoclonal Antibodies: Principles and Practice, Academic Press, (1986) pp. 59-103.
Hoogenboom and Winter, J. Mol. Biol. 227:381 (1991).
Houghton, 1992. Biotechniques 13:412-421.
Huse, et al., 1989 Science 246:1275-1281.
Huston et al. (1988) Proc Nat Acad Sci USA 85 (16): 5879-5883.
Hwang et al., Proc. Natl. Acad. Sci. USA, 77: 4030 (1980).
Igarashi et al., Nat. Med. 5:211-16 (1999).
Jansen et al., Immunological Reviews 62:185-216 (1982).
Kaplitt, M. G. et al., Nat. Genet. 8:148 (1994).
Keller et al., Clin. Microbiol. Rev. 13:602-14 (2000).
Killen and Lindstrom, Jour. Immun. 133:1335-2549 (1984).
Corti Davide et al: "A Neutralizing Antibody Selected from Plasma Cells That Binds to Group 1 and Group 2 Influenza A Hemagglutinins", Science, America Association for the Advancement of Science, vol. 333, No. 6044, Aug. 12, 2011 (Aug. 12, 2011), pp. 850-856.
Weibin Hu et al: "Fully human broadly neutralizing monoclonal antibodies influenza A viruses generated from the memory B cells of a 2009 pandemic H1N1 influenza vaccine recipient", Virology, vol. 435, No. 2, Jan. 1, 2013 (Jan. 1, 2013), pp. 320-328.
Hashem A M et al: "Universal antibodies against the highly conserved influenza fusion peptide cross-neutralize several subtypes of influenza A virus", Biochemical and Biophysical Research Communicaitons, Academic Press Inc. Orlando, FL, US, vol. 403, No. 2, Dec. 10, 2010 (Dec. 10, 2010), pp. 247-251.
Gerald Nakamura et al: "An in Vivo Human-Plasmablast Enrichment Technique Allows Rapid Identificaiton of Therapeutic Influenza A Antibodies", Cell Host & Microbe, vol. 14, No. 1, Jul. 1, 2013 (Jul. 1, 2013), pp. 93-103.

* cited by examiner

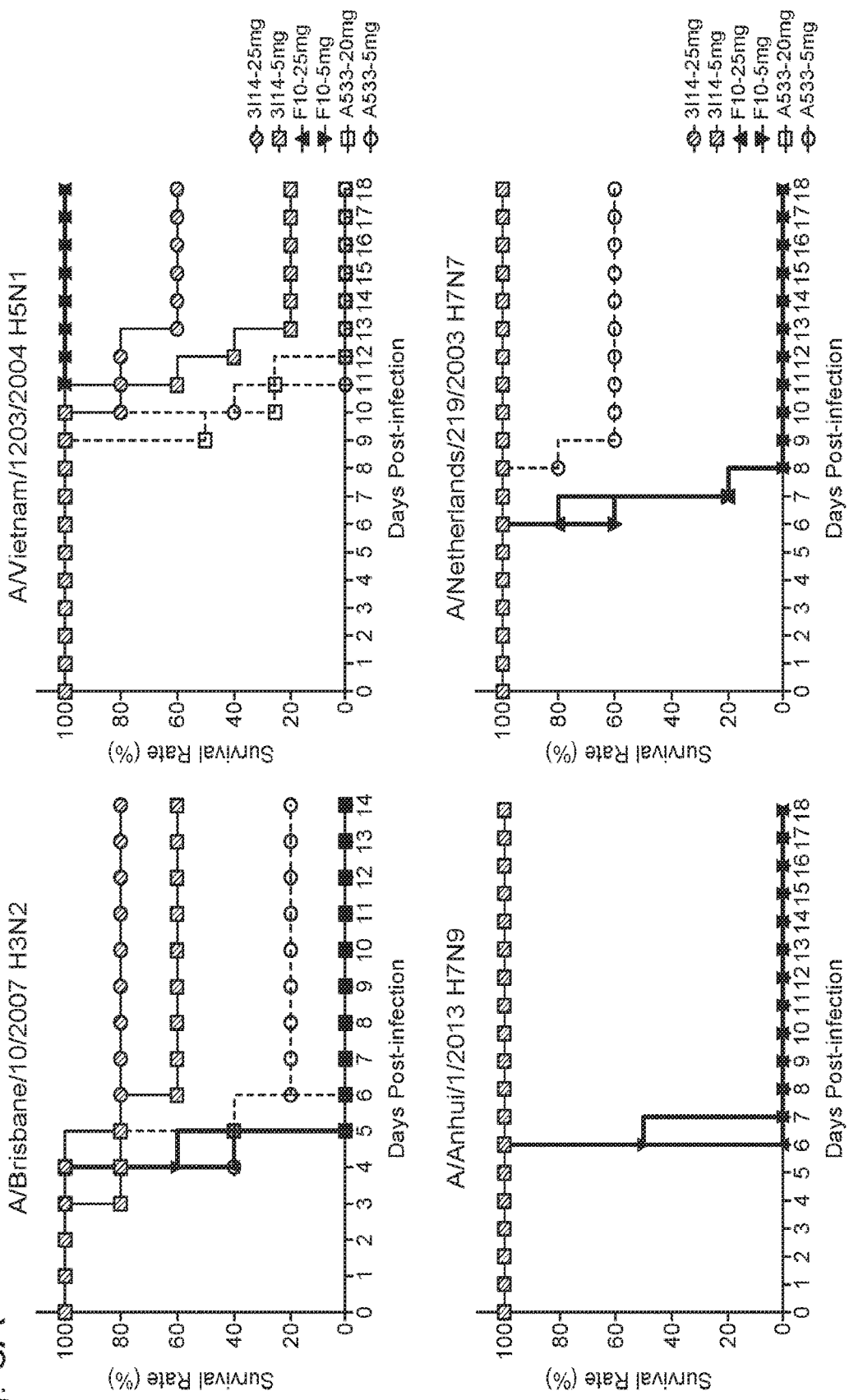

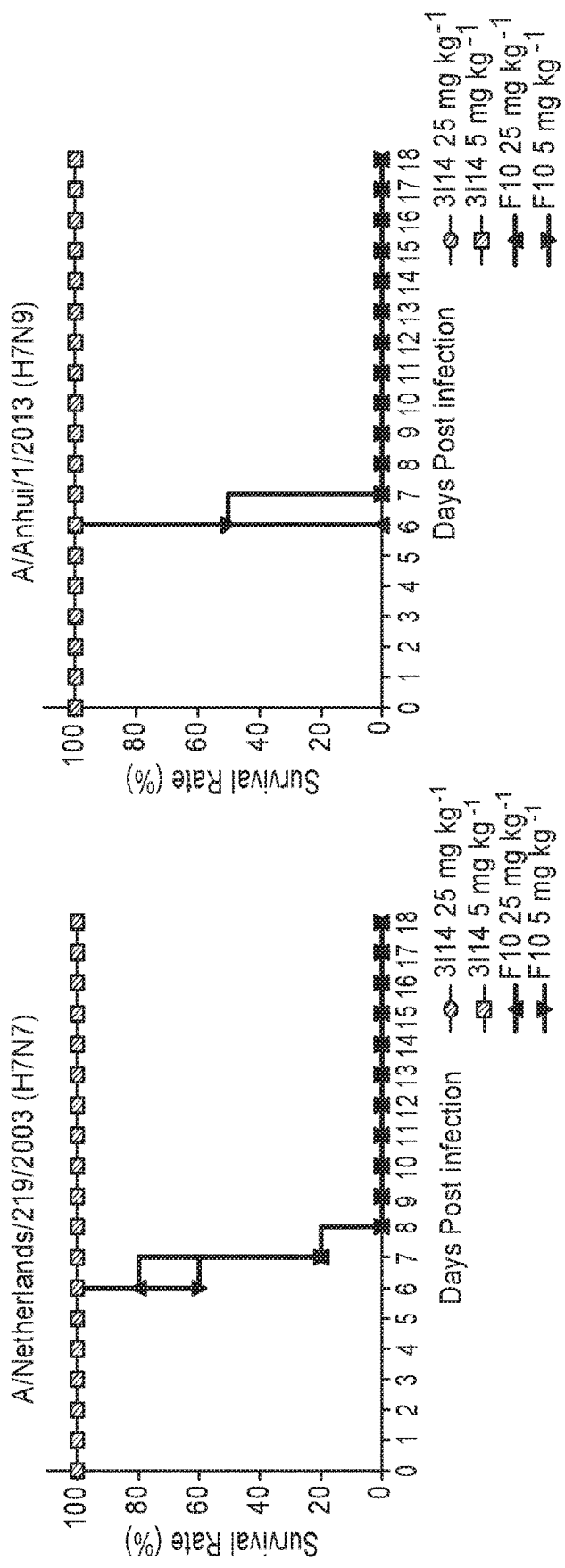

Fig. 9A
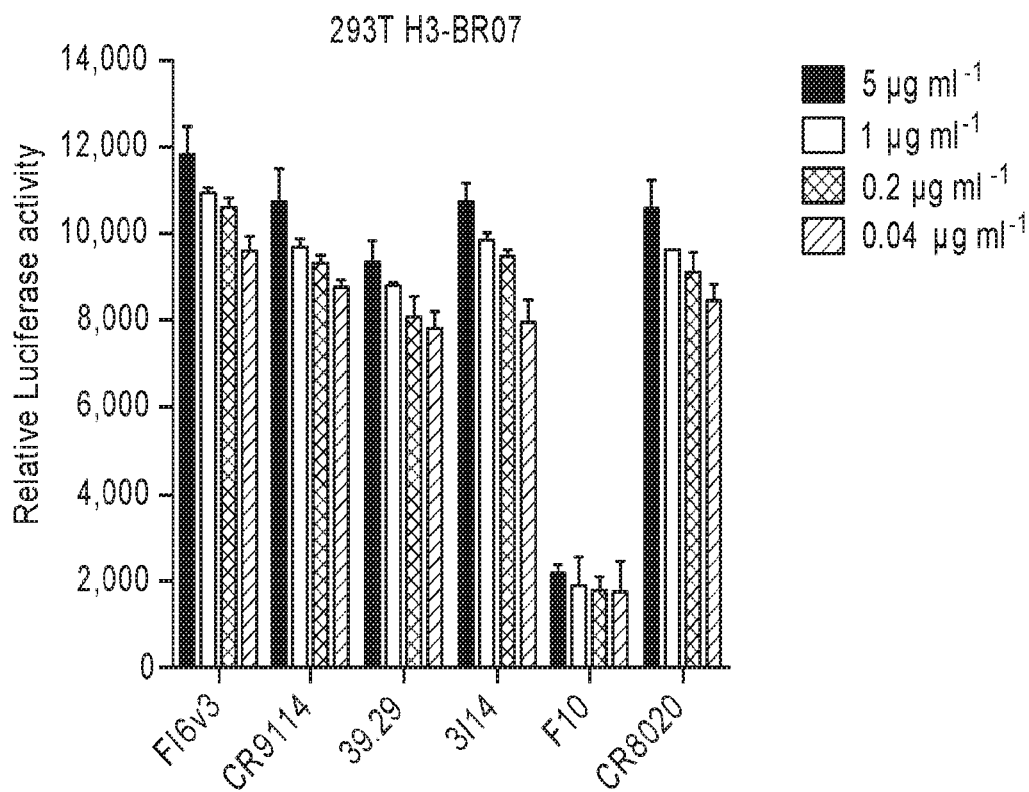
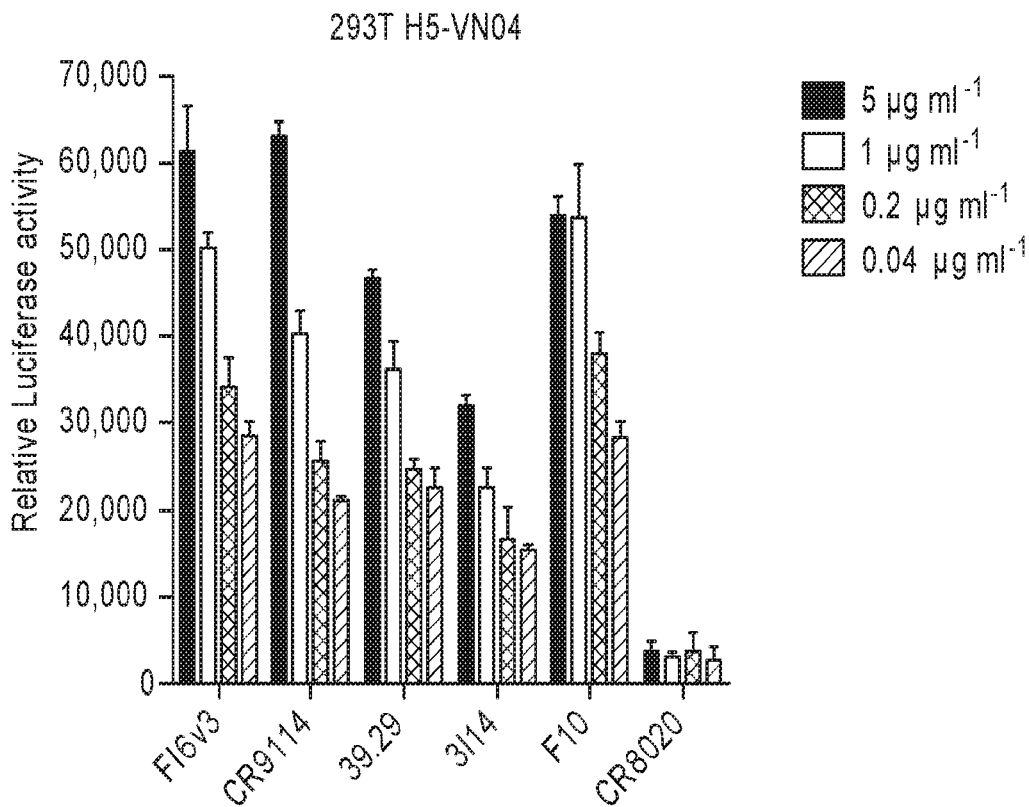

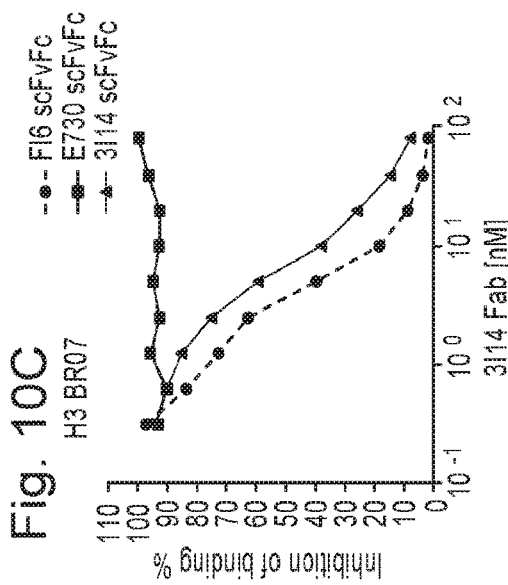
Fig. 10A H3 BR07
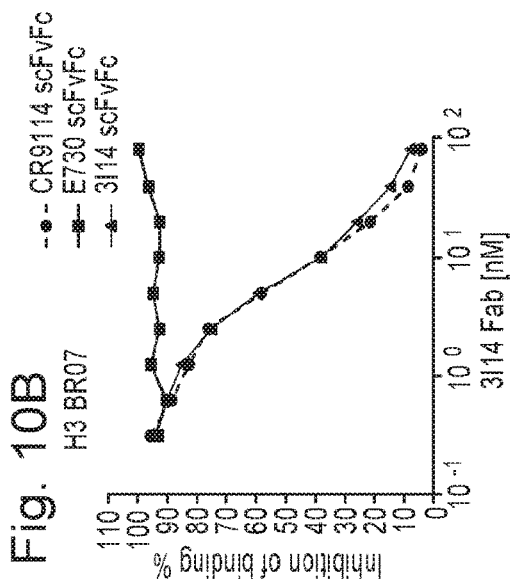
Fig. 10B H3 BR07
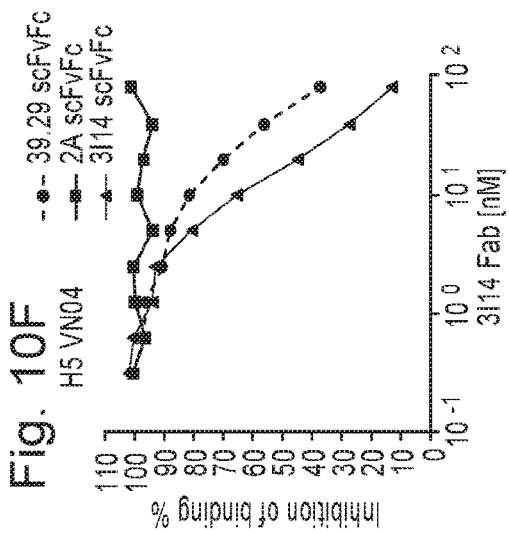
Fig. 10C H3 BR07
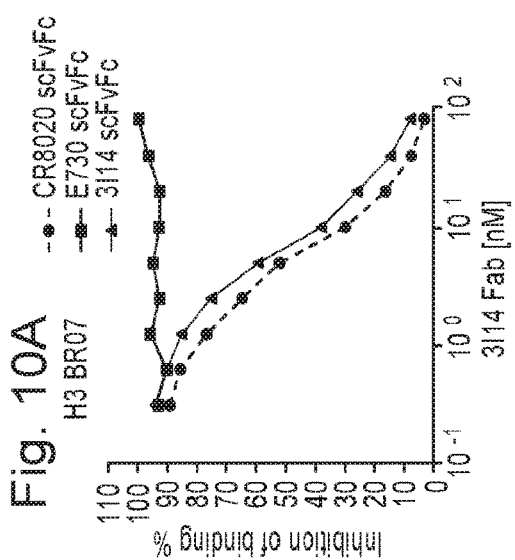
Fig. 10D H3 BR07
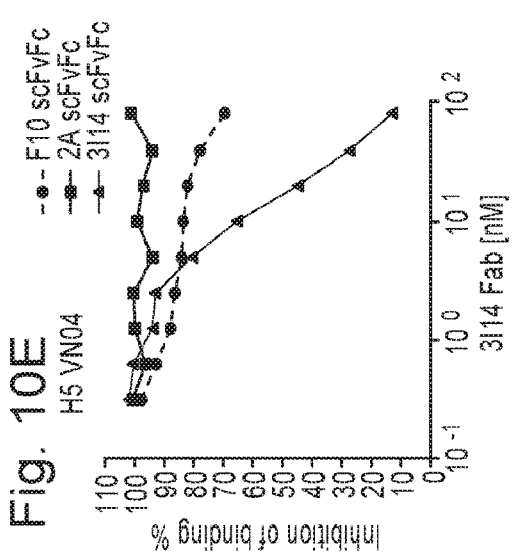
Fig. 10E H5 VN04
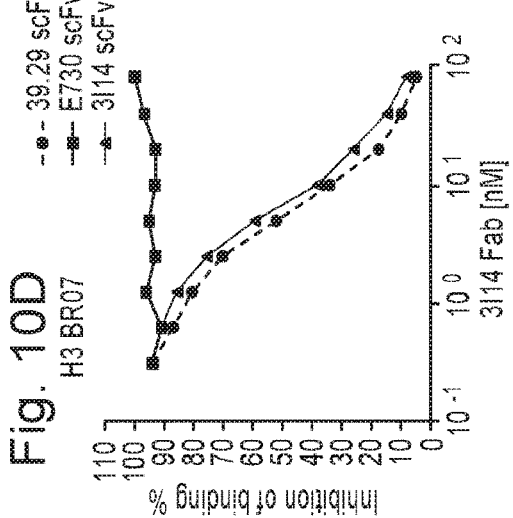
Fig. 10F H5 VN04

```
              1           10          20          30          40          50          60
3I14 VH       QVQLLESGGG  VVQPGRSLRL  SCAASGFTFS  NYGMHWVRQA  PGKGLEWVAI  ISFDGSKKYY
VH3-30*18     .....V....  ..........  ..........  .S........  ..........  .V...Y....N...
IGHD3-22*01
IGHJ4*02

70          80          90          100         110         120
3I14 VH       ANSVKGRSTI  SRDNSKNTLS  LQMNSLGPED  TALYYCAKLP  SPYYFDSRFV  WVAASAFHFW
VH3-30*18     .D.....F..  ..........  .......Y..  ..V.....R.  ..........  ..........
IGHD3-22*01                                       ...Y..
IGHJ4*02                                                                           Y.DY.

130
3I14 VH       GQGILVTVSS
VH3-30*18     ..........
IGHD3-22*01
IGHJ4*02      ...T......
```

B

```
              1           10          20          30          40          50          60
3I14 VL       NFMLTQPPSA  SGTPGQRVTI  SCSGSSSNIG  GNTVHWFQQL  PGTAPKLLIY  TNSLRPSGVP
IGLV1-44      QSV.......  ..........  ..........  .S...N.Y..  ..........  S.NQ......
IGLJ3*02

70          80          90          100         110
3I14 VL       DRFSGSKSGT  SASLAISGLQ  SEDEADYYCA  AWDDSLNGQV  FGGGTKLTVL
IGLV1-44      ..........  ..........  ..........  ..........  ..........
IGLJ3*02                                          .......W..  ..........
```

Fig. 11C

```
                     primer-flanking region                                                HCDR1
                     1              10         20                30            40           50        60            70
                     QVQLLESGGG VVQPGRSLRL SCAASGFTFS NYGMHWVRQA PGKGLEWVAI SFDGSKKY ANSVKGRSTI
3I14 VH              ...........................................................................
3I14 VHGL            ....V....................................S........V.....Y..N.............D......F..
VH3-30*18 (X92214)   ....V....................................S........V.....Y..N.............D......F..
IGHD3-22*01 (X93616)
IGHJ4*02 (X86355)

HCDR3
                     80            90         100           110            120          130
                     SRDNSKNTLS LQMNSLGPED TALYYC KLP SPYYFDSRFV WVAASAFHFW GQGILVTVSS
3I14 VH              ......................................................................
3I14 VHGL            ........Y.......RA.........V...R    ..Y..SGY YY   Y.DY    ...T........
VH3-30*18 (X92214)   ........Y.......RA.........V...
IGHD3-22*01 (X93616)                                    ..Y..SGY YY
IGHJ4*02 (X86355)                                                Y.DY       ...T........
                                                      V_H D_H junction   D_H J_H junction
```

Fig. 11D

```
                     primer-flanking region                              LCDR1                              LCDR2
                     1              10         20                30            40           50        60            70
                     NFMLTQPPSA SGTPGQRVTI SCSGS SNIG GNTTHWFQQL PGTAPKLLIY TNS RPSGVP DRFSGSKSGT
3I14 VL              QSV...........................................................S.N.........................
3I14 VLGL            QSV........................................S...N.Y..............S.N.........................
IGLV1-44 (Z73654)    QSV........................................S...N.Y..............S.N.........................
IGLJ3*02 (M15642)

LCDR3
                     80            90         100           110
                     SASLAISGLQ SEDEADYYC AWDDSLNGQV FGGGTKLTV
3I14 VH              .........................................
3I14 VLGL            ....................W.....................
IGLV1-44 (Z73654)    ....................W.....................
IGLJ3*02 (M15642)
```

|   | 18 | 19 | 20 | 21 |   | 38 | 39 |   | 41 | 42 |   | 45 | 46 | 47 |   | 48 | 49 | 50 |
|---|----|----|----|----|---|----|----|---|----|----|---|----|----|----|---|----|----|----|
| H3 | I | D | G | W |  | L | K |  | T | Q |  | I | D | Q |  | I | N | G |
| H5 | V | D | G | Q |  | K | E |  | T | Q |  | I | D | G |  | V | T | N |
| B  | I | A | G | W |  | L | K |  | T | Q |  | I | N | K |  | I | T | K |

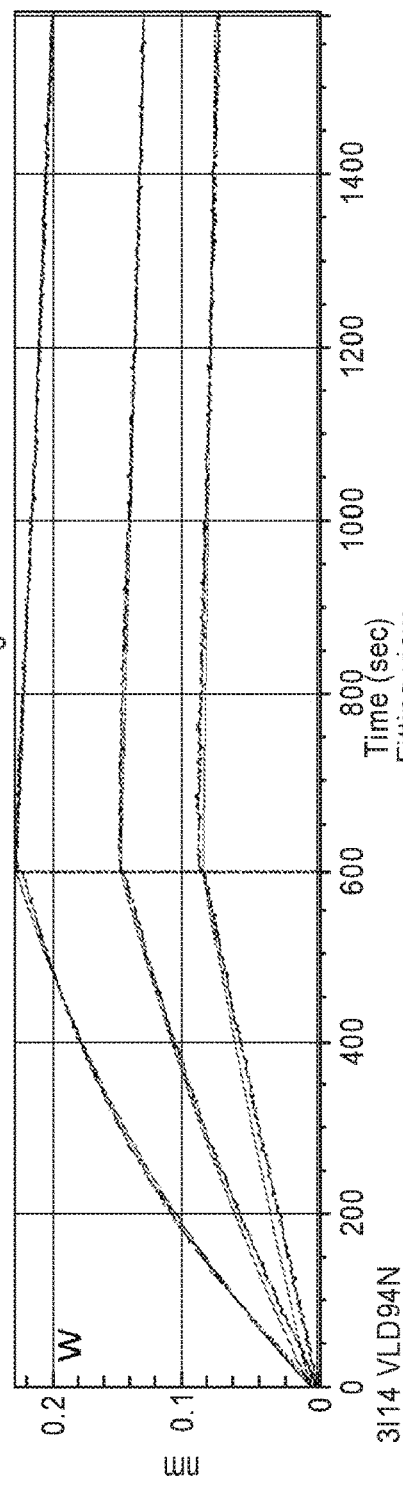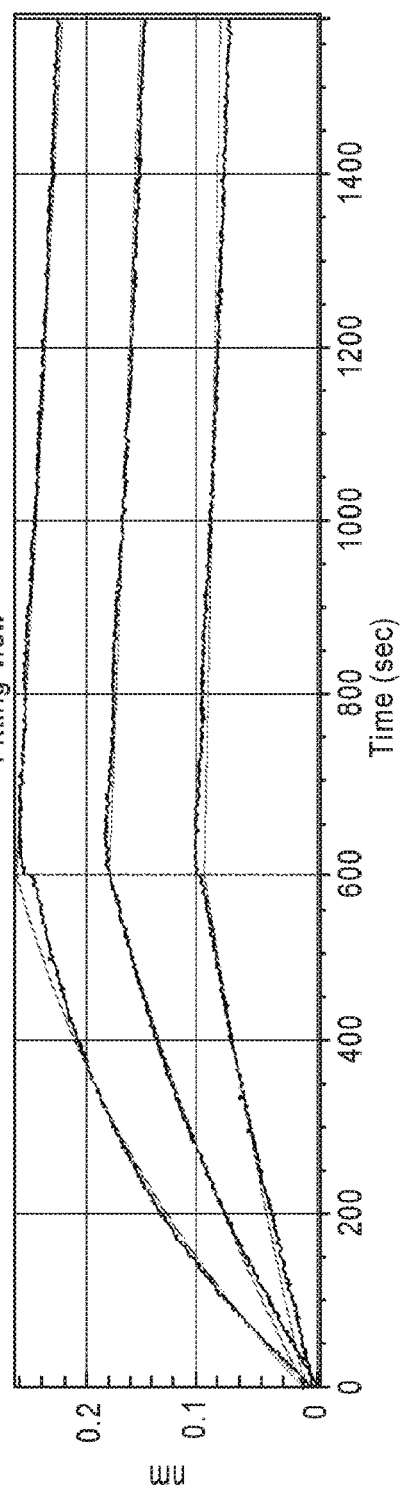
Fig. 15B

Fig. 15F
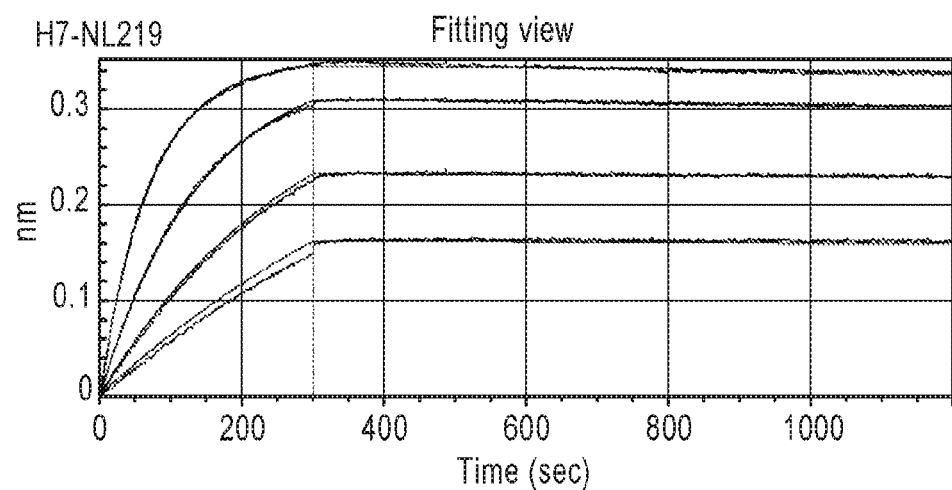
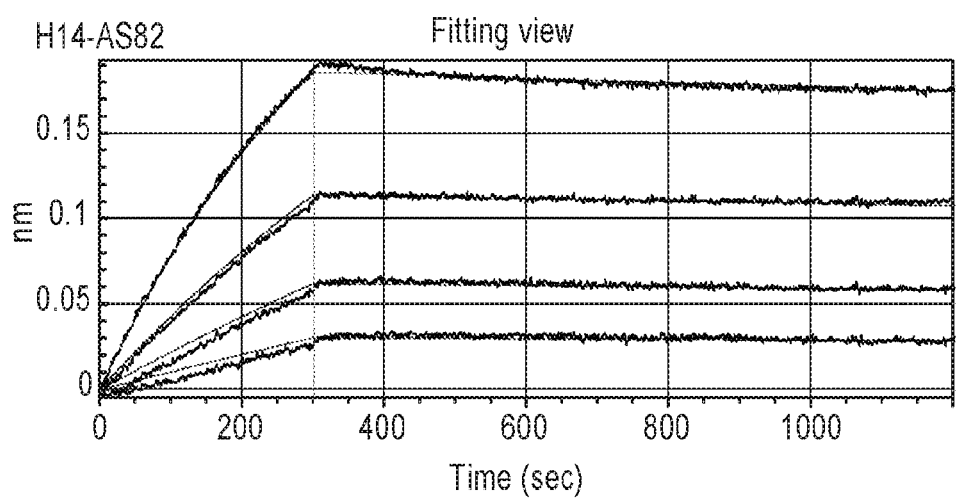

SEQUENCE LISTING

```
<160> NUMBER OF SEQ ID NOS: 25

<210> SEQ ID NO 1
<211> LENGTH: 390
<212> TYPE: DNA
<213> ORGANISM: Homo sapiens

<400> SEQUENCE: 1
caggtgcagc tgttggagtc tgggggaggc gtggtccagc ctgggaggtc cctgagactc      60
tcctgtgcag cctctggatt caccttcagt aactatggca tgcactgggt ccgccaggct     120
ccaggcaagg ggctggagtg ggtggcaatt atatcatttg atggaagtaa aaaatattat     180
gcaaactccg tgaagggccg atccaccatc tccagagaca attccaagaa cacgctgtct     240
ctgcaaatga acagcctggg acctgaggac acggctctat attactgtgc gaaactgccc     300
tccccgtatt actttgatag tcggttcgtg tgggtcgccg ccagcgcatt tcacttctgg     360
ggccagggaa tcctggtcac cgtctcttca                                      390

<210> SEQ ID NO 2
<211> LENGTH: 130
<212> TYPE: PRT
<213> ORGANISM: Homo sapiens

<400> SEQUENCE: 2

Gln Val Gln Leu Leu Glu Ser Gly Gly Gly Val Val Gln Pro Gly Arg
 1               5                  10                  15

Ser Leu Arg Leu Ser Cys Ala Ala Ser Gly Phe Thr Phe Ser Asn Tyr
            20                  25                  30
```

```
Gly Met His Trp Val Arg Gln Ala Pro Gly Lys Gly Leu Glu Trp Val
         35                  40                  45
Ala Ile Ile Ser Phe Asp Gly Ser Lys Lys Tyr Tyr Ala Asn Ser Val
 50                  55                  60
Lys Gly Arg Ser Thr Ile Ser Arg Asp Asn Ser Lys Asn Thr Leu Ser
 65                  70                  75                  80
Leu Gln Met Asn Ser Leu Gly Pro Glu Asp Thr Ala Leu Tyr Tyr Cys
                 85                  90                  95
Ala Lys Leu Pro Ser Pro Tyr Tyr Phe Asp Ser Arg Phe Val Trp Val
            100                 105                 110
Ala Ala Ser Ala Phe His Phe Trp Gly Gln Gly Ile Leu Val Thr Val
            115                 120                 125
Ser Ser
    130

<210> SEQ ID NO 3
<211> LENGTH: 330
<212> TYPE: DNA
<213> ORGANISM: Homo sapiens

<400> SEQUENCE: 3
aattttatgc tgactcagcc accctcagcg tctgggaccc ccgggcagag ggtcaccatc      60
tcttgctctg gaagcagctc aacatcgga ggtaatactg tacactggtt ccagcagctc     120
ccaggaacgg cccccaaact cctcatctat actaatagtc tgcggccctc aggggtccct     180
gaccgattct ctggctccaa gtctggcacc tcagcctccc tggccatcag tgggctccag     240
tctgaggatg aggctgatta ttactgtgca gcatgggatg acagcctaaa tggtcaggtg     300
ttcggcggag ggaccaagct gaccgtccta                                     330

<210> SEQ ID NO 4
<211> LENGTH: 110
<212> TYPE: PRT
<213> ORGANISM: Homo sapiens

<400> SEQUENCE: 4

Asn Phe Met Leu Thr Gln Pro Pro Ser Ala Ser Gly Thr Pro Gly Gln
 1               5                  10                  15
Arg Val Thr Ile Ser Cys Ser Gly Ser Ser Asn Ile Gly Gly Asn
            20                  25                  30
Thr Val His Trp Phe Gln Gln Leu Pro Gly Thr Ala Pro Lys Leu Leu
         35                  40                  45
Ile Tyr Thr Asn Ser Leu Arg Pro Ser Gly Val Pro Asp Arg Phe Ser
 50                  55                  60
Gly Ser Lys Ser Gly Thr Ser Ala Ser Leu Ala Ile Ser Gly Leu Gln
 65                  70                  75                  80
Ser Glu Asp Glu Ala Asp Tyr Tyr Cys Ala Ala Trp Asp Asp Ser Leu
                 85                  90                  95
Asn Gly Gln Val Phe Gly Gly Gly Thr Lys Leu Thr Val Leu
            100                 105                 110

<210> SEQ ID NO 5
<211> LENGTH: 330
<212> TYPE: DNA
<213> ORGANISM: Artificial Sequence
<220> FEATURE:
<223> OTHER INFORMATION: Modified VL chain of 3I14VLD94N nucleic acid

<400> SEQUENCE: 5
```

```
aattttatgc tgactcagcc accctcagcg tctgggaccc ccgggcagag ggtcaccatc     60
tcttgctctg gaagcagctc caacatcgga ggtaatactg tacactggtt ccagcagctc    120
ccaggaacgg cccccaaact cctcatctat actaatagtc tgcggccctc agggtccct    180 gaccgattct ctggctccaa gtctggcacc tcagcctccc tggccatcag tgggctccag    240
tctgaggatg aggctgatta ttactgtgca gcatgggata acagcctaaa tggtcaggtg    300
ttcggcggag ggaccaagct gaccgtccta                                     330
```

<210> SEQ ID NO 6
<211> LENGTH: 110
<212> TYPE: PRT
<213> ORGANISM: Artificial Sequence
<220> FEATURE:
<223> OTHER INFORMATION: Modified VL chain of 3I14VLD94N amino acid

<400> SEQUENCE: 6

```
Asn Phe Met Leu Thr Gln Pro Pro Ser Ala Ser Gly Thr Pro Gly Gln
1               5                   10                  15

Arg Val Thr Ile Ser Cys Ser Gly Ser Ser Asn Ile Gly Gly Asn
            20                  25                  30

Thr Val His Trp Phe Gln Gln Leu Pro Gly Thr Ala Pro Lys Leu Leu
        35                  40                  45

Ile Tyr Thr Asn Ser Leu Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asn Ser Leu
                85                  90                  95

Asn Gly Gln Val Phe Gly Gly Gly Thr Lys Leu Thr Val Leu
            100                 105                 110
```

<210> SEQ ID NO 7
<211> LENGTH: 8
<212> TYPE: PRT
<213> ORGANISM: Homo sapiens

<400> SEQUENCE: 7

```
Gly Phe Thr Phe Ser Asn Tyr Gly
1               5
```

<210> SEQ ID NO 8
<211> LENGTH: 8
<212> TYPE: PRT
<213> ORGANISM: Homo sapiens

<400> SEQUENCE: 8

```
Ile Ser Phe Asp Gly Ser Lys Lys
1               5
```

<210> SEQ ID NO 9
<211> LENGTH: 25
<212> TYPE: PRT
<213> ORGANISM: Homo sapiens

<400> SEQUENCE: 9

```
Cys Ala Lys Leu Pro Ser Pro Tyr Tyr Phe Asp Ser Arg Phe Val Trp
1               5                   10                  15

Val Ala Ala Ser Ala Phe His Phe Trp
            20                  25
```

```
<210> SEQ ID NO 10
<211> LENGTH: 8
<212> TYPE: PRT
<213> ORGANISM: Homo sapiens

<400> SEQUENCE: 10

Ser Ser Asn Ile Gly Gly Asn Thr
1               5

<210> SEQ ID NO 11
<211> LENGTH: 3
<212> TYPE: PRT
<213> ORGANISM: Homo sapiens

<400> SEQUENCE: 11

Thr Asn Ser
1

<210> SEQ ID NO 12
<211> LENGTH: 13
<212> TYPE: PRT
<213> ORGANISM: Homo sapiens

<400> SEQUENCE: 12

Cys Ala Ala Trp Asp Asp Ser Leu Asn Gly Gln Val Phe
1               5                   10

<210> SEQ ID NO 13
<211> LENGTH: 13
<212> TYPE: PRT
<213> ORGANISM: Artificial Sequence
<220> FEATURE:
<223> OTHER INFORMATION: Modified 3I14VLD94N Light CDR3

<400> SEQUENCE: 13

Cys Ala Ala Trp Asp Asn Ser Leu Asn Gly Gln Val Phe
1               5                   10

<210> SEQ ID NO 14
<211> LENGTH: 8
<212> TYPE: PRT
<213> ORGANISM: Artificial Sequence
<220> FEATURE:
<223> OTHER INFORMATION: Modified 3I14VLD94N Light CDR1
<220> FEATURE:
<221> NAME/KEY: MISC_FEATURE
<222> LOCATION: (6)..(6)
<223> OTHER INFORMATION: Xaa = Any amino acid other the glycine;
      preferably X is serine

<400> SEQUENCE: 14

Ser Ser Asn Ile Gly Xaa Asn Thr
1               5

<210> SEQ ID NO 15
<211> LENGTH: 324
<212> TYPE: PRT
<213> ORGANISM: Influenza A Virus

<400> SEQUENCE: 15

Asp Gln Ile Cys Ile Gly Tyr His Ala Asn Asn Ser Thr Glu Lys Val
1               5                   10                  15

Asp Thr Asn Leu Glu Arg Asn Val Thr Val Thr His Ala Lys Asp Ile
                20                  25                  30
```

```
Leu Glu Lys Thr His Asn Gly Lys Leu Cys Lys Leu Asn Gly Ile Pro
             35                  40                  45

Pro Leu Glu Leu Gly Asp Cys Ser Ile Ala Gly Trp Leu Leu Gly Asn
 50                  55                  60

Pro Glu Cys Asp Arg Leu Leu Ser Val Pro Glu Trp Ser Tyr Ile Met
 65                  70                  75                  80

Glu Lys Glu Asn Pro Arg Asp Gly Leu Cys Tyr Pro Gly Ser Phe Asn
             85                  90                  95

Asp Tyr Glu Glu Leu Lys His Leu Leu Ser Ser Val Lys His Phe Glu
            100                 105                 110

Lys Val Lys Ile Leu Pro Lys Asp Arg Trp Thr Gln His Thr Thr Thr
            115                 120                 125

Gly Gly Ser Arg Ala Cys Ala Val Ser Gly Asn Pro Ser Phe Phe Arg
130                 135                 140

Asn Met Val Trp Leu Thr Lys Glu Gly Ser Asp Tyr Pro Val Ala Lys
145                 150                 155                 160

Gly Ser Tyr Asn Asn Thr Ser Gly Glu Gln Met Leu Ile Ile Trp Gly
            165                 170                 175

Val His His Pro Ile Asp Glu Thr Glu Gln Arg Thr Leu Tyr Gln Asn
            180                 185                 190

Val Gly Thr Tyr Val Ser Val Gly Thr Ser Thr Leu Asn Lys Arg Ser
            195                 200                 205

Thr Pro Glu Ile Ala Thr Arg Pro Lys Val Asn Gly Gln Gly Gly Arg
            210                 215                 220

Met Glu Phe Ser Trp Thr Leu Leu Asp Met Trp Asp Thr Ile Asn Phe
225                 230                 235                 240

Glu Ser Thr Gly Asn Leu Ile Ala Pro Glu Tyr Gly Phe Lys Ile Ser
            245                 250                 255

Lys Arg Gly Ser Ser Gly Ile Met Lys Thr Glu Gly Thr Leu Glu Asn
            260                 265                 270

Cys Glu Thr Lys Cys Gln Thr Pro Leu Gly Ala Ile Asn Thr Thr Leu
            275                 280                 285

Pro Phe His Asn Val His Pro Leu Thr Ile Gly Glu Cys Pro Lys Tyr
            290                 295                 300

Val Lys Ser Glu Lys Leu Val Leu Ala Thr Gly Leu Arg Asn Val Pro
305                 310                 315                 320

Gln Ile Glu Ser

<210> SEQ ID NO 16
<211> LENGTH: 974
<212> TYPE: DNA
<213> ORGANISM: Influenza A Virus

<400> SEQUENCE: 16
gaccagatat gcattggata ccatgccaat aattccacag agatggtcga cacaattcta      60
gagcggaacg tcactgtgac tcatgccaag gacattcttg agaagaccca taacggaaag     120
ttatgcaaac taacggaat ccctccactt gaactagggg actgtagcat gccggatgg       180 ctccttggaa atccagaatg tgataggctt ctaagtgtgc cagaatggtc ctatataatg     240
gagaaagaaa acccgagaga cggtttgtgt tatccaggca gcttcaatga ttatgaagaa     300
ttgaaacatc tcctcagcag cgtgaaacat ttcgagaaag taagattct gcccaaagat     360 agatggacac agcatacaac aactggaggt tcacgggcct gcgcggtgtc tggtaatcca     420
tcattcttca ggaacatggt ctggctgaca aagaaaggat cagattatcc ggttgccaaa     480
```

```
ggatcgtaca acaatacaag cggagaacaa atgctaataa tttggggggt gcaccatccc      540
aatgatgaga cagaacaaag aacattgtac cagaatgtgg gaacctatgt ttccgtaggc      600
acatcaacat tgaacaaaag gtcaaccccc gaaatagcaa caaggcttaa agtgaatgga      660
caaggaggta gaatggaatt ctcttggacc ctcttggata tgtgggacac cataaatttt      720
gagagtactg gtaatctaat tgcaccagag tatggattca aaatatcgaa agaggtagt       780 tcagggatca tgaaaacaga aggaacactt gagaactgtg agaccaaatg ccaaactcct      840
ttgggagcaa taatacaac attgccttt cacaatgtcc acccactgac aataggtgag       900
tgccccaaat atgtaaaatc ggagaagttg gtcttagcaa caggactaag gaatgttccc      960
cagattgaat caag                                                       974
```

<210> SEQ ID NO 17
<211> LENGTH: 222
<212> TYPE: PRT
<213> ORGANISM: Influenza A Virus
<400> SEQUENCE: 17

```
Gly Leu Phe Gly Ala Ile Ala Gly Phe Ile Glu Gly Gly Trp Gln Gly
1               5                   10                  15

Met Val Asp Gly Trp Tyr Gly Tyr His His Ser Asn Asp Gln Gly Ser
            20                  25                  30

Gly Tyr Ala Ala Asp Lys Glu Ser Thr Gln Lys Ala Phe Asp Gly Ile
        35                  40                  45

Thr Asn Lys Val Asn Ser Val Ile Glu Lys Met Asn Thr Gln Phe Glu
    50                  55                  60

Ala Val Gly Lys Glu Phe Gly Asn Leu Glu Arg Arg Leu Glu Asn Leu
65                  70                  75                  80

Asn Lys Arg Met Glu Asp Gly Phe Leu Asp Val Trp Thr Tyr Asn Ala
                85                  90                  95

Glu Leu Leu Val Leu Met Glu Asn Glu Arg Thr Leu Asp Phe His Asp
            100                 105                 110

Ser Asn Val Lys Asn Leu Tyr Asp Lys Val Arg Met Gln Leu Arg Asp
        115                 120                 125

Asn Val Lys Glu Leu Gly Asn Gly Cys Phe Glu Phe Tyr His Lys Cys
    130                 135                 140

Asp Asp Glu Cys Met Asn Ser Val Lys Asn Gly Thr Tyr Asp Tyr Pro
145                 150                 155                 160

Lys Tyr Glu Glu Glu Ser Lys Leu Asn Arg Asn Glu Ile Lys Gly Val
                165                 170                 175

Lys Leu Ser Ser Met Gly Val Tyr Gln Ile Leu Ala Ile Tyr Ala Thr
            180                 185                 190

Val Ala Gly Ser Leu Ser Leu Ala Ile Met Met Ala Gly Ile Ser Phe
        195                 200                 205

Trp Met Cys Ser Asn Gly Ser Leu Gln Cys Arg Ile Cys Ile
    210                 215                 220
```

<210> SEQ ID NO 18
<211> LENGTH: 668
<212> TYPE: DNA
<213> ORGANISM: Influenza A Virus
<400> SEQ

```
ggtatggata ccatcacagc aatgaccagg gatcagggta tgcagcagac aaagaatcca      120
ctcaaaaggc atttgatgga atcaccaaca aggtaaattc tgtgattgaa agatgaaca       180 cccaatttga agctgttggg aaagaattca gtaacttaga gagaagactg agaacttga      240 acaaaaagat ggaagacggg tttctagatg tgtggacata caatgctgag cttctagttc     300
tgatggaaaa tgagaggaca cttgactttc atgattctaa tgtcaagaat ctgtatgata     360
aagtcagaat gcagttgaga gacaacgtca agaactagg aaatggatgt tttgaatttt      420
atcacaaatg tgatgatgaa tgcatgaata gtgtgaaaac cgggacgtat gattatccca    480
agtatgaaga gagtctaaa ctaaatagaa atgaaatcaa aggggtaaaa ttgagcagca      540
tgggggttta tcaaatcctt gccatttatg ctacagtagc aggttctctg tcactggcaa     600
tcatgatggc tgggatctct ttctggatgt gctccaacgg gtctctgcag tgcaggatct     660
gcatatga                                                              668

<210> SEQ ID NO 19
<211> LENGTH: 562
<212> TYPE: PRT
<213> ORGANISM: Influenza A Virus

<400> SEQUENCE: 19

Met Ala Ile Ile Tyr Leu Ile Leu Leu Phe Thr Ala Val Arg Gly Asp
1               5                   10                  15

Gln Ile Cys Ile Gly Tyr His Ala Asn Asn Ser Thr Glu Met Val Asp
            20                  25                  30

Thr Ile Leu Glu Arg Asn Val Thr Val Thr His Ala Lys Asp Ile Leu
        35                  40                  45

Glu Lys Thr His Asn Gly Lys Leu Cys Lys Leu Asn Gly Ile Pro Pro
    50                  55                  60

Leu Glu Leu Gly Asp Cys Ser Ile Ala Gly Trp Leu Leu Gly Asn Pro
65                  70                  75                  80

Glu Cys Asp Arg Leu Leu Ser Val Pro Glu Trp Ser Tyr Ile Met Glu
                85                  90                  95

Lys Glu Asn Pro Arg Asp Gly Leu Cys Tyr Pro Gly Ser Phe Asn Asp
            100                 105                 110

Tyr Glu Glu Leu Lys His Leu Leu Ser Ser Val Lys His Phe Glu Lys
        115                 120                 125

Val Lys Ile Leu Pro Lys Asp Arg Trp Thr Gln His Thr Thr Thr Gly
    130                 135                 140

Gly Ser Arg Ala Cys Ala Val Ser Gly Asn Pro Ser Phe Phe Arg Asn
145                 150                 155                 160

Met Val Trp Leu Thr Lys Lys Gly Ser Asp Tyr Pro Val Ala Lys Gly
                165                 170                 175

Ser Tyr Asn Asn Thr Ser Gly Glu Gln Met Leu Ile Ile Trp Gly Val
            180                 185                 190

His His Pro Asn Asp Glu Thr Glu Gln Arg Thr Leu Tyr Gln Asn Val
        195                 200                 205

Gly Thr Tyr Val Ser Val Gly Thr Ser Thr Leu Asn Lys Arg Ser Thr
    210                 215                 220

Pro Glu Ile Ala Thr Arg Leu Lys Val Asn Gly Gln Gly Gly Arg Met
225                 230                 235                 240

Glu Phe Ser Trp Thr Leu Leu Asp Met Trp Asp Thr Ile Asn Phe Glu
                245                 250                 255

Ser Thr Gly Asn Leu Ile Ala Pro Glu Tyr Gly Phe Lys Ile Ser Lys
```

-continued

```
            260                 265                 270

Arg Gly Ser Ser Gly Ile Met Lys Thr Glu Gly Thr Leu Glu Asn Cys
        275                 280                 285

Glu Thr Lys Cys Gln Thr Pro Leu Gly Ala Ile Asn Thr Thr Leu Pro
    290                 295                 300

Phe His Asn Val His Pro Leu Thr Ile Gly Glu Cys Pro Lys Tyr Val
305                 310                 315                 320

Lys Ser Glu Lys Leu Val Leu Ala Thr Gly Leu Arg Asn Val Pro Gln
                325                 330                 335

Ile Glu Ser Arg Gly Leu Phe Gly Ala Ile Ala Gly Phe Ile Glu Gly
            340                 345                 350

Gly Trp Gln Gly Met Val Asp Gly Trp Tyr Gly Tyr His His Ser Asn
        355                 360                 365

Asp Gln Gly Ser Gly Tyr Ala Ala Asp Lys Glu Ser Thr Gln Lys Ala
    370                 375                 380

Phe Asp Gly Ile Thr Asn Lys Val Asn Ser Val Ile Glu Lys Met Asn
385                 390                 395                 400

Thr Gln Phe Glu Ala Val Gly Lys Glu Phe Ser Asn Leu Glu Arg Arg
                405                 410                 415

Leu Glu Asn Leu Asn Lys Lys Met Glu Asp Gly Phe Leu Asp Val Trp
            420                 425                 430

Thr Tyr Asn Ala Glu Leu Leu Val Leu Met Glu Asn Glu Arg Thr Leu
        435                 440                 445

Asp Phe His Asp Ser Asn Val Lys Asn Leu Tyr Asp Lys Val Arg Met
    450                 455                 460

Gln Leu Arg Asp Asn Val Lys Glu Leu Gly Asn Gly Cys Phe Glu Phe
465                 470                 475                 480

Tyr His Lys Cys Asp Asp Glu Cys Met Asn Ser Val Lys Thr Gly Thr
                485                 490                 495

Tyr Asp Tyr Pro Lys Tyr Glu Glu Glu Ser Lys Leu Asn Arg Asn Glu
            500                 505                 510

Ile Lys Gly Val Lys Leu Ser Ser Met Gly Val Tyr Gln Ile Leu Ala
        515                 520                 525

Ile Tyr Ala Thr Val Ala Gly Ser Leu Ser Leu Ala Ile Met Met Ala
    530                 535                 540

Gly Ile Ser Phe Trp Met Cys Ser Asn Gly Ser Leu Gln Cys Arg Ile
545                 550                 555                 560

Cys Ile

<210> SEQ ID NO 20
<211> LENGTH: 1689
<212> TYPE: DNA
<213> ORGANISM: Influenza A Virus

<400> SEQUENCE: 20
atggccatca tttatctcat tctcctgttc acagcagtga gaggggacca gatatgcatt     60
ggataccatg ccaataattc cacagagatg gtcgacacaa ttctagagcg gaacgtcact    120
gtgactcatg ccaaggacat tcttgagaag acccataacg gaaagttatg caaactaaac    180
ggaatccctc cacttgaact aggggactgt agcattgccg gatggctcct tggaaatcca    240
gaatgtgata ggcttctaag tgtgccagaa tggtcctata taatggagaa agaaaacccg    300
agagacggtt tgtgttatcc aggcagcttc aatgattatg aagaattgaa acatctcctc    360
agcagcgtga aacatttcga gaaagtaaag attctgccca aagatagatg gacacagcat    420
```

-continued

```
acaacaactg gaggttcacg ggcctgcgcg gtgtctggta atccatcatt cttcaggaac      480
atggtctggc tgacaaagaa aggatcagat tatccggttg ccaaggatc gtacaacaat       540 acaagcggag aacaaatgct aataatttgg ggggtgcacc atcccaatga tgagacagaa      600
caaagaacat tgtaccagaa tgtgggaacc tatgtttccg taggcacatc aacattgaac      660
aaaaggtcaa ccccagaaat agcaacaagg cttaaagtga atggacaagg aggtagaatg      720
gaattctctt ggaccctctt ggatatgtgg gacaccataa attttgagag tactggtaat      780
ctaattgcac cagagtatgg attcaaaata tcgaaaagag gtagttcagg gatcatgaaa      840
acagaaggaa cacttgagaa ctgtgagacc aaatgccaaa ctccctttgg gagcaataaat     900 acaacattgc ttttcacaa tgtccaccca ctgacaatag gtgagtgccc caaatatgta       960
aaatcggaga agttggtctt agcaacagga ctaaggaatg ttccccagat tgaatcaaga      1020
ggattgtttg ggcaatagc tggttttata gaaggaggat ggcaaggaat ggttgatggt      1080
tggtatggat accatcacag caatgaccag ggatcagggt atgcagcaga caaagaatcc      1140
actcaaaagg catttgatgg aatcaccaac aaggtaaatt ctgtgattga aagatgaac      1200 acccaatttg aagctgttgg gaaagaattc agtaacttag agagaagact ggagaacttg      1260
aacaaaaaga tggaagacgg gttttctagat gtgtggacat acaatgctga gcttctagtt     1320
ctgatggaaa atgagaggac acttgacttt catgattcta atgtcaagaa tctgtatgat      1380
aaagtcagaa tgcagttgag agacaacgtc aaagaactag gaaatggatg tttttgaattt   1440 tatcacaaat gtgatgatga atgcatgaat agtgtgaaaa ccgggacgta tgattatccc      1500
aagtatgaag aagagtctaa actaaataga aatgaaatca aggggtaaa attgagcagc      1560 atggggtttt atcaaatcct tgccatttat gctacagtag caggttctct gtcactggca     1620
atcatgatgg ctgggatctc tttctggatg tgctccaacg ggtctctgca gtgcaggatc      1680
tgcatatga                                                                1689
```

`<210> SEQ ID NO 21`
`<211> LENGTH: 755`
`<212> TYPE: DNA`
`<213> ORGANISM: Homo sapiens`

`<400> SEQUENCE: 21`

```
catggagttt gggctgagct gggttttcct cgttgctctt ttaagaggtg attcatggag      60
aaatagagag actgagtgtg agtgaacatg agtgagaaaa actggatttg tgtggcattt     120
tctgataacg gtgtccttct gtttgcaggt gtccagtgtc aggtgcagct ggtggagtct      180
gggggaggcg tggtccagcc tgggaggtcc ctgagactct cctgtgcagc ctctggattc      240
accttcagta gctatggcat gcactgggtc cgccaggctc aggcaaggg gctggagtgg      300 gtggcagtta tatcatatga tggaagtaat aaatactatg cagactccgt gaagggccga      360
ttcaccatct ccagagacaa ttccaagaac acgctgtatc tgcaaatgaa cagcctgaga      420
gctgaggaca cggctgtgta ttactgtgcg aaagacacag tgagggaag tcattgtgcg      480 cccagacaca aacctccctg caggaacgct ggcgggaaat cagcggcagg gggcgctcag      540
gagccactga tcagagtcag ccctagaggc aggtgcagat ggaggctgtt tcctgtcagg     600
atgtgggact ttgtcttctt ctgacagttc cccaaggaac ctcttaaatt tagaaaactg      660
tgcctaacaa tgtcttctct atgcatatga ggacctttc tccctagcac aaaatgcaga      720
ttgacgctga cacggatgaa aattcctcaa ccatg                                   755
```

<210> SEQ ID NO 22
<211> LENGTH: 66
<212> TYPE: PRT
<213> ORGANISM: Homo sapiens

<400> SEQUENCE: 22

```
Val Ile Ser Tyr Asp Gly Ser Asn Lys Tyr Tyr Ala Asp Ser Val Lys
1               5                   10                  15

Gly Arg Leu Thr Ile Ser Arg Asp Asn Ser Lys Asn Thr Leu Tyr Leu
            20                  25                  30

Gln Met Asn Ser Leu Arg Ala Glu Asp Thr Ala Val Tyr Tyr Cys Ala
        35                  40                  45

Lys Asp Phe Gly Pro Lys Arg Pro Thr Gly Asp Tyr Phe Asp Tyr Trp
    50                  55                  60

Gly Gln
65
```

<210> SEQ ID NO 23
<211> LENGTH: 296
<212> TYPE: DNA
<213> ORGANISM: Homo sapiens

<400> SEQUENCE: 23

```
cagtctgtgc tgactcagcc accctcagcg tctgggaccc ccgggcagag ggtcaccatc    60
tcttgttctg gaagcagctc caacatcgga agtaatactg taaactggta ccagcagctc   120
ccaggaacgg cccccaaact cctcatctat agtaataatc agcggccctc agggtccct    180 gaccgattct ctggctccaa gtctggcacc tcagcctccc tggccatcag tgggctccag   240
tctgaggatg aggctgatta ttactgtgca gcatgggatg acagcctgaa tggtcc       296
```

<210> SEQ ID NO 24
<211> LENGTH: 98
<212> TYPE: PRT
<213> ORGANISM: Homo sapiens

<400> SEQUENCE: 24

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly
```

<210> SEQ ID NO 25
<211> LENGTH: 17
<212> TYPE: PRT
<213> ORGANISM: Artificial Sequence
<220> FEATURE:
<223> OTHER INFORMATION: C-terminal peptide tag

<400> SEQUENCE: 25

-continued

```
Gly Gly Gly Leu Asn Asp Ile Phe Glu Ala Gln Lys Ile Glu Trp His
1               5                   10                  15
Glu
```

HUMANIZED INFLUENZA MONOCLONAL ANTIBODIES AND METHODS OF USE THEREOF

RELATED APPLICATIONS

This application is a national stage entry of PCT Application No. PCT/US2016/026800, filed on Apr. 8, 2018, which claims priority to, and the benefit of, U.S. Provisional Application No. 62/144,729, filed on Apr. 8, 2016, the contents of which is incorporated herein by reference in its entirety.

GOVERNMENT INTEREST

This invention was made with government support under [ ] awarded by [ ]. The United States government has certain rights in the invention.

INCORPORATION OF SEQUENCE LISTING

The contents of the text file submitted electronically herewith are incorporated herein by reference in their entirety: A computer readable format copy of the Sequence Listing (filename: DFCI_109_N01US_SeqList_ST25.txt, date recorded: May 27, 2016, file size 25 kb).

FIELD OF THE INVENTION

This invention relates generally to influenza neutralizing antibodies and methods for use thereof.

BACKGROUND OF THE INVENTION

An influenza pandemic represents one of the greatest acute infectious threats to human health. Vaccination remains the principle means of preventing seasonal and pandemic influenza and its complications. A "universal" influenza vaccine that induces broad immunity against multiple subtypes of influenza viruses has been a long sought goal in medical research. The recent discovery of human broadly neutralizing "heterosubtypic" antibodies binding to a highly conserved hydrophobic pocket on the stem of HA (sBnAb) have reignited efforts to develop such a vaccine. However, only very low concentrations of sBnAbs are detected in the sera of seasonal influenza or H5N1 vaccines, or in commercial intravenous immunoglobulin (IVIG) preparations.

There is continuous effort to produce monoclonal antibodies (mAbs) and drugs for immunotherapies against the influenza virus. Specifically, efforts are directed to development of a therapeutic compound that neutralizes all of the various influenza strains. Currently, only a handful mAbs are reported that are able to achieve this goal. These mAbs were isolated by panning phage antibody libraries and by screening B-cells from vaccinated volunteers. However, an increased understanding of characteristics of broadly neutralizing influenza antibodies may be useful to incorporate certain structural determinants in a more rational design approach for discovery and production of a broad panel of neutralizing influenza antibodies.

Thus, there exists a great need for additional monoclonal antibodies that can broadly neutralize influenza virus and methods for increasing the affinity or efficacy of such antibodies through a rational design approach.

SUMMARY OF THE INVENTION

The present invention features an isolated recombinantly produced monoclonal antibody wherein the antibody has the following characteristics: a heavy chain variable region encoded by the IGHV3-30 germline gene; binds an epitope in the stem region of a hemaggluitinin (HA) protein; and neutralizes group 1 and group 2 influenza A viruses.

In one aspect, the monoclonal antibody has one or more of the following characteristics: a light chain variable region encoded by the IGLV1-44 germline gene; a heavy chain CDR 3 comprising the amino acid sequence of SEQ ID NO:9; binds uncleaved HA0; prevents HA0 cleavage; and/or binds a conformational epitope defined by amino acids 18, 19, 20, 21, 36, 38, 39, 41, 42, 45, 45, 49 and 53 of an HA2 polypeptide when numbered in accordance with SEQ ID NO:18

The present invention features an isolated monoclonal antibody that neutralizes an influenza virus comprising: a heavy chain comprising a CDR1 comprising the amino acid sequence of SEQ ID NO:7; a CDR2 comprising the amino acid sequence of SEQ ID NO: 8 and a CDR3 comprising the amino acid sequence of SEQ ID NO:9; and a light chain comprising a CDR1 comprising the amino acid sequence of SEQ ID NOs:10 or SEQ ID NO:14; a CDR2 comprising the amino acid sequence of SEQ ID NO: 11; and a CDR3 comprising the amino acid sequence of SEQ ID NO: 12 or SEQ ID NO:13.

The present invention also features an isolated monoclonal antibody wherein said antibody comprises a $V_H$ amino acid sequence of SEQ ID NO: 2 and a VL amino acid sequence of SEQ ID NO: 4 or SEQ ID NO: 6; a VH amino acid sequence of SEQ ID NO: 2 and a VL amino acid sequence of SEQ ID NO: 24; or a VH amino acid sequence of SEQ ID NO: 22 and a VL amino acid sequence of SEQ ID NO: 4 or 6.

The antibody binds a conformational epitope defined by amino acids 18, 19, 20, 21, 36, 38, 39, 41, 42, 45, 45, 49 and 53 of an HA2 polypeptide.

In one aspect, the antibody is a single chain Fv antibody, an $F_{ab}$ fragment, an $F_{ab'}$ fragment, or an $F_{(ab')2}$ fragment. In another aspect, the antibody is linked to a therapeutic agent. For example, the therapeutic agent is a toxin, a radiolabel, a siRNA, a small molecule, or a cytokine.

The present invention also features a composition comprising any of the antibodies disclosed herein, and a carrier.

The present invention provides a nucleic acid sequence comprising a nucleic acid sequence selected from SEQ ID NOs: 1, 3, and 5. In another embodiment, a nucleic acid sequence encoding a polypeptide comprising amino acid sequences selected from SEQ ID NO: 2, 4, and 6. In one aspect, a polypeptide comprising an amino acid sequence selected from SEQ ID NOs: 2, 4, and 6.

The present invention provides a vector comprising nucleic acid sequence selected from SEQ ID NOs: 1, 2, 3, 4, 5 and 6. In one aspect, the present invention provides a cell comprising the vector comprising nucleic acid sequences 1, 2, 3, 4, or 6.

The present invention further provides a cell producing any of the antibodies disclosed herein.

The present invention further provides a method for treating a disease or disorder caused by an influenza virus, by administering to a person at risk of suffering from said disease or disorder, a therapeutically effective amount of any of the monoclonal antibodies described herein. Optionally, the method further includes administering an anti-viral agent.

Other features and advantages of the invention will be apparent from and are encompassed by the following detailed description and claims.

BRIEF DESCRIPTION OF THE DRAWINGS

In FIG. 5 B anti-group 1 mAb F10 scFvFc was used for reference.

FIGS. 9A and 9B demonstrate that 3I14 mediates Antibody-Dependent Cellular Cytotoxicity (ADCC). FIG. 9A is a graph that depicts the results of the ADCC based assay. 3I14 and other anti-stem bnAbs, FI6v3, CR9114, 39.29, F10 and CR8020 induced ADCC in H3- and H5-expressed 293T cells. For these assays, $1\times10^4$/well H3 or H5-expressed 293T cells were attached to the plates prior to assay, and the medium was then replaced with low IgG serum assay buffer (RPMI 1640 with 0.5% low IgG FBS). Different bnAbs were added to each well at a concentration of 5, 1, 0.2 and 0.04 µg ml-1. After one-hour, Jurkat effector cells were added at $6.0\times10^4$ cells/well to assay plates in low IgG serum assay buffer and incubated for 6 hours. The supernatants were harvested and luciferase activity was measured using Bio-Glo™ Luciferase Assay kits (Promega). FIG. 9B is a series of graphs that depict 3I14 and other anti-stem bnAbs, FI6v3, CR9114, 39.29, F10 and CR8020 induced ADCC in H3- and H5-expressed 293T cells. $2\times10^4$/well H3 or H5-expressing 293T cells were attached to the plates prior to the assay, and the medium was then replaced with low IgG serum assay buffer (RPMI 1640 with 0.5% low IgG FBS). Different bnAbs were added to each well at a concentration of 10, 5, 2.5 and 1.25 µg ml$^{-1}$. After one-hour, PBMCs were added at $1.2\times10^5$ cells/well to assay plates in low IgG serum assay buffer and incubated for 6 hours. The supernatants were harvested and luciferase activity was measured using LDH Cytotoxicity Assay Kit (Pierce). Data represent mean±S.E.M. Experiments were performed three times with similar results. Data are representative of one independent experiment with three replicates per group.

FIG. 10 is a series of graphs that depict 3I14 cross-competes for the binding of other anti-stem bnAbs, FI6v3, CR9114, 39.29, F10 and CR8020 to H3 or H5. For these assays, 5 µg/ml H3-BR07 or H5-VN04 protein was immobilized on ELISA plates and were incubated with a 2-fold serial dilution of 3I14 Fab ranging in concentration from 80 nM to 0.3 nM; these were further mixed with other scFvFc Abs at 5 nM. The binding of scFvFc Abs was detected using HRP conjugated anti-human CH2 antibodies.

FIG. 11 depicts an amino acid sequence alignment of 3I14 and other germline heavy chain (A, C) or light chain regions (B, D). The corresponding V, D and J sequences were determined using the IMGT database and are shown for comparison.

The bnAbs are displayed in ribbon representations. In FIG. 12B, the heavy chain is in blue and the light chain is in cyan. The HCDR3s are highlighted with 3I14 in red, FI6v3 in magenta, 39.29 in yellow and MAb 3.1 in green.

FIGS. 15A-15F is a graph and a table that depicts $K_d$ binding values of 3I14 WT and the VLD94N IgG1 variants binding to recombinant H5-VN04 (A) and H3-PE09 (B). Green or blue curves are the experimental trace obtained from biolayer interferometry experiments, and red curves are the best global fits to the data used to calculate the $K_d$ values. Affinity measurements (Kd values) for the binding curves are reported in Table 4. 3I14 WT bound purified H5-VN04 with $K_d$ value at 1.15 nM, while 3I14 VLD94N mutant bound H5-VN04 with 10-fold higher affinity at 0.19 nM. FIG. 15 C-F are a series of graphs that depict 3I14 scFvFc binding to recombinant Ha.

DETAILED DESCRIPTION

Figure 1A:
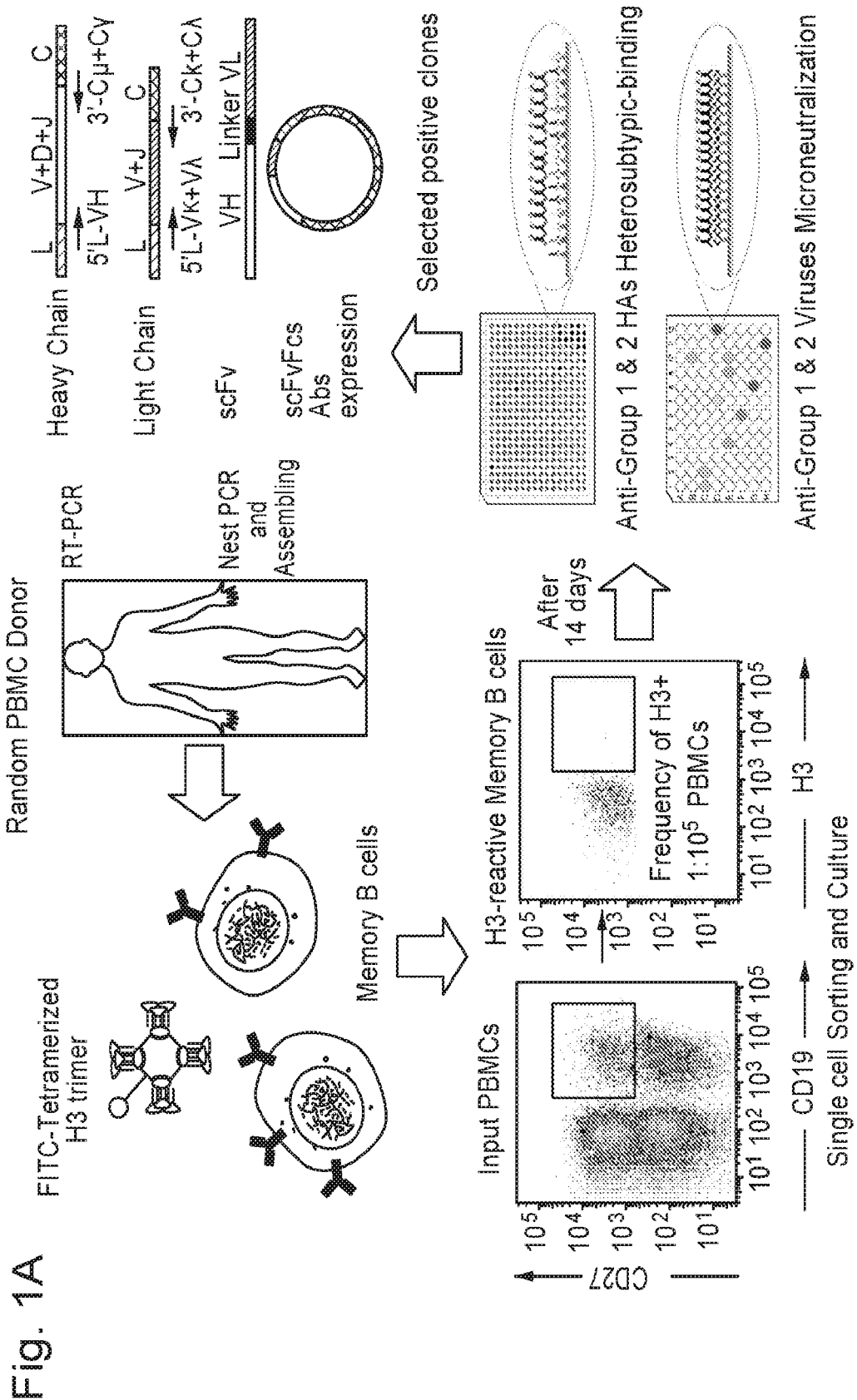
FIG. 1A is a schematic that depicts the isolation of broadly neutralizing Abs against influenza viruses from human memory B cell repertoire. Representative fluorescence-labeled cell sorting (FACS) data are also presented. The FACS data indicate the frequency of H3-reactive memory B cells isolated from total PBMCs.

Influenza A is a negative-sense, single-stranded RNA virus, with an eight-segment genome encoding 10 proteins. It belongs to the family Orthomyxoviridae which includes the genera of influenza virus A, B and C as defined by the antigenicity of the nucleocapsid and matrix proteins. Generally, influenza A virus is associated with more severe disease in humans. Influenza A virus is further subtyped by two surface proteins, hemagglutinin (HA) which attaches the virion to the host cell for cell entry, and neuraminidase (NA) which facilitates the spread of the progeny virus by cleaving the host sialic acid attached to the progeny virus or cell surface.

There are 16 HA subtypes and 9 NA subtypes which make up all subtypes of influenza A viruses by various combinations of HA and NA. All combinations of the 16 HA and 9 NA virus subtypes are found in water fowl. Of the hundreds of strains of avian influenza A viruses, only four are known to have caused human infections: H5N1, H7N3, H7N7 and H9N2. In general, human infection with these viruses has resulted in mild symptoms and very little severe illness: there has been only one fatal case of pneumonia caused by H7N7. However, the exception is the highly pathogenic H5N1 virus, for which there is no natural immunity in humans. The infidelity of the RNA polymerase and the selective pressure of host immunity can lead to the accumulation of mutations and change in surface antigenicity of these proteins. This antigenic change is called antigenic drift. In addition, as a result of its segmented genome, shuffling of gene segments can occur if two different subtypes of influenza A virus infect the same cell. For example, if a human H3N2 virus and an avian H5N1 virus co-infect a human or other member of a mammalian species, such an event can produce a novel H5N2. This novel virus can then be efficiently transmitted from human to human because all of most of the gene segments come from the human virus. Such genetic reassortment would lead to a major antigen change, a so-called antigenic shift, which would mean that most of the global population would not have any neutralizing antibodies against the reassortant virus. Such a situation, coupled with the high mortality of influenza H5N1 pneumonia, is one of the most feared scenarios in the field of public health.

Influenza virus hemagglutinin (HA) is the most variable antigen of influenza virus, and is responsible for virus entry into cells. It is synthesized as a trimeric precursor polypeptide HA0 which is post-translationally cleaved to two polypeptides HA' and HA2 linked by a single disulphide bond. The HA' chain of HA is responsible for the attachment of virus to the cell surface. HA2 mediates the fusion of viral and cell membranes in endosomes, allowing the release of the ribonucleoprotein complex into the cytoplasm. In contrast to HA1, the HA2 molecule represents a relatively conserved part of HA. A second immunogenic influenza protein is neuraminidase (NA). This tetrameric glycoprotein is responsible for releasing virions from surface sialic acid on producer cells, and may also have a role in promoting access to target cells in the airways. Although neutralizing antibodies against NA are protective in animals and man, there is a paucity of data on their mechanisms of action. A recent report on the crystal structure of N1 neuraminidase demonstrated the presence of a cavity adjacent to its active site that may be exploited to develop new anti-influenza drugs, including antibodies. This finding is particularly important in light of the reports of emergence of drug resistance to oseltamivir (Tamiflu) and zanamivir (Relenza) for H5N1 viruses.

More than two decades ago, the HA molecule of the H3 subtype was characterized by sequencing the HA of antigenic drift variants and escape mutants, and the antigenic epitopes were mapped on the molecule's three-dimensional structure. Since then, the antigenic sites on H1, H2 and H5 of an avian pathogenic virus were mapped on the three-dimensional structures of H3. After the outbreak of H5N1 infection in humans in Hong Kong in 1997 and the isolation of H9N2 virus from human cases in 1999, the X-ray structures of both proteins were solved. However, antigenic drift of the 1997 swine isolate (A/Duck/Singapore/3/97) that was used to solve the structure, and more recently isolated highly pathogenic strains, is significant. Indeed, there are 28 minor changes and two potentially major changes between the swine isolate (A/Duck/Singapore/3/97) and the HPAI H5N1 strain (A/Vietnam1203/04).

Phylogenetic analyses of the H5 HA genes from the 2004-2005 outbreak have shown two different lineages of HA genes, termed clades 1 and 2. HPAI H5N1 strain (A/Vietnam1203/04) is a member of clade 1. Viruses in each of these clades are distributed in non-overlapping geographic regions of Asia. The H5N1 viruses from Indochina are tightly clustered within clade 1, whereas H5N1 isolated from several surrounding countries are distinct from clade 1 isolates, and belong in a more divergent clade 2. Clade 1 viruses were isolated from humans and birds in Vietnam, Thailand and Cambodia but only from birds in Laos and Malaysia. The clade 2 viruses were found in viruses isolated exclusively from birds in China, Indonesia, Japan, and South Korea. The most recent epidemiologic studies analyzed 82 H5N1 viruses isolated from poultry throughout Indonesia and Vietnam, as well as 11 human isolates from southern Vietnam together with sequence data available in public databases, to address questions relevant to virus introduction, endemicity and evolution[36]. Phylogenetic analysis showed that all viruses from Indonesia form a distinct sublineage of H5N1 genotype Z viruses, suggesting that this outbreak likely originated from a single introduction via spread throughout the country during the past two years. Continued virus activities in Indonesia were attributed to transmission via poultry movement within the country, rather than through repeated introductions by bird migration. Within Indonesia and Vietnam, H5N1 viruses have evolved over time into geographically distinct groups within each country.

Recently, the structure of HA from A/Vietnam1203/4 was solved. Comparison of its amino acid sequences with the HA genes from HPAI 2004 and 2005 isolates from clade 1 and 2 viruses identified 13 positions of antigenic variation that are mainly clustered around the receptor binding domain, while the rest are within the vestigual esterase domain. Regions of antigenic variation have been identified in H1 and H3 serotypes. For H1, these sites are designated Sa, Sb, Ca and Cb while for H3, sites are designated A, B, C and D. Escape mutants of H5 HAs can be clustered into three epitopes; site 1: an exposed loop (HA' 140-145) that overlaps antigenic sites A of H3 and Ca2 of $H^2$; site 2: HA1 residues 156 and 157 that corresponds to antigenic site B in H3 serotypes; and 3) HA1 129-133, which is restricted to the Sa site in H1 HAs and H9 serotypes. In the recent studies by Smith, detection of positive selection at the amino acid level indicated that eight residues in the HA proteins were under positive selection. These residues include five in antigenic sites A and E (positions 83, 86, 138, 140 and 141); two involved in receptor binding (positions 129 and 175); and positions 156 is a site for potential N-linked glycosylation that is near the receptor-binding site. The results further revealed that three residues in HA (Val 86, Ser 129 and Thr 156) were more frequently observed in human isolates than in chicken or duck isolates and likely represented early adaptation of H5N1 genotype Z to humans. Another important finding from these studies is that the phylogenetic differences between the Indonesian and Vietnamese sublineages was also reflected in significant differences in antigenic cross-reactivity between these two group of viruses. Specifically, viruses from Indonesia did not react to ferret antisera against A/Vietnam1203/04, and representative viruses from Vietnam did not react with ferret antisera against Indonesian viruses IDN/5/06 and Dk/IDN/MS/04. These findings are in agreement with earlier studies with immune human serum and human 1997 and 2003 H5N1 viruses that these strains were not only phylogenetically but also antigenically distinct. Thus, natural variation as well as escape mutants suggests that continued evolution of the virus should impact the decision on which strain(s) should be used for passive and active immunization Identification and Characterization of scFvs and Monoclonal Antibodies High affinity, cross-subtype, broadly-neutralizing human anti-HA mAbs have been identified. Antigen-specific memory B cells were isolated from human PBMCs using tetramerized H3 (A/Brisbane/10/2007) hemagglutinin (HA) trimers. The H3-reactive single memory B cells were sorted into plates and stimulated in vitro. More than 40% sorted B cells produced on average 200 ng/ml IgG in the supernatant after 14 days. Supernatants from the expanded B cells were measured for their heterosubtypic binding specificity and neutralizing activity by MSD or a highly sensitive neutralization assay. Antibody genes from selective clones were recovered by single cell RT-PCR.

Through screening 2688 memory B clones from 7 individuals, 11% clonable memory B cells were reactive with H3 hemagglutinin. Among them, H3/H7, H3/H7/H1 and H3/H7/H1/influenza B heterosubtypic binding population were 16%, 6.9% and 0.35%, respectively. A new broadly neutralizing Ab, 3I14 was identified. 3I14 was characterized and shown to possess cross-reactive binding and neutralization activity against both group 1 and group 2 influenza A viruses. This is in contrast to other known anti-influenza antibodies, such as F10, CR6261, MAb 3.1 and CR8020 which neutralize either group 1 or group 2 influenza A viruses. Only, anti-influenza antibodies FI6v3, CR9114, 39.39, MAb 1.12 and CT149 are capable of neutralizing human influenza A viruses from both group 1 and group 2. In contrast to FI6v3, CR9114, 39.39, MAb 1.12 and CT149 which were isolated from cultures of human plasma cells, plasmablasts and CD138+ HA specific antibody secreting cells, the antibodies of the present invention, e.g. 3I14, were isolated from memory B-cells. In response to viral reinfection and vaccination, long-lived plasma cells produce neutralizing antibodies, specifically recalling the original virus, whereas the memory B cells contribute by producing high-affinity neutralizing antibodies specific for the variant virus by re-entering germinal centers. Furthermore, the somatic mutations of memory B cells could be accumulated in older individuals through repeated cycles of antibody divergence and selection. Thus, memory B cells have a broader repertoire of antigen specificity than long-lived plasma cells. It is considered essential for a long-lasting, broadly efficacious vaccine to develop the stable population of memory B cells and elicit potent bnAb responses. Accordingly the antibodies of the present invention will have greater therapeutic utility than the other known anti-influenza antibodies.

The antibody of the invention binds surface-expressed HAs across serotypes of both group 2 (H3, H4, H7, H14 and H15) and group 1 (H1, H2, H5, H6, H8, H9, H11, H12 and H16) influenza A. Specially, the binding affinity (Kd) of the antibodies of the invention is between about 1 pM to 1 µM, between about 1 pM to 1 nM or between about 1 nM to 1 µM. For example, the antibody has binding affinity to group 1 (H1, H5, and H9) and group 2 (H3, H4, H7 and H17) of between about 1 pM to 1 µM. Preferably, the binding affinity to group 1 (H1, H5, and H9) and group 2 (H3, H4, H7 and H17) the Kd is about 0.01 nM to 10 nM. In some embodiments, the antibody has a binding affinity to group 2 HAs (H3, H4, H7 and H14) of between about 1 µM to 1 µM for group 2 influenza A viruses. Preferably, the binding affinity to group 2 HAs (H3, H4, H7 and H14) the Kd is <1 nM.

Specifically, 3I14 bound purified HA proteins of different subtypes that belong to group 2 (H3, H4, H7 and H14) and group 1 (H1, H5 and H9) with dissociation constants ($K_d$) ranging from 0.01 nM to 10 nM and to all tested group 2 HAs (H3, H4, H7 and H14) with high affinity (mean $K_d$<0.1 nM). In addition, 3I14 bound to group 1 H1 subtypes (H1-CA09, H1-SI06 and H1-PR8) with high affinity, whereas its affinity for other group 1 subtypes (H5-VN04, H5-1N05 and H9-HK99) was lower (mean $K_d$=1.02, 1.05 and 5.23 nM, respectively). This lower binding affinity to H5 influenza viral subtypes is unlike other broadly neutralizing antibodies previously describe such as FI6v3 and 39.29.

The antibody of the invention neutralizes influenza A virus. By "neutralize" or "neutralization" is meant cause a reduction in viral infectivity by the binding of the antibody to the viral particles, thus blocking a step in the replication cycle of the virus that precedes virally encoded transcription or synthesis. The antibody may neutralize virus by various mechanisms, for example, the antibody may neutralize a virus by interfering with a virion binding to a receptor, block uptake into cells, prevent uncoating of the genomes in endosomes, or can cause the virus particles to aggregate, or lyse.

The antibody of the invention neutralizes across serotypes of both group 2 and group 1 influenza A virus. The antibody of the invention has a half maximal inhibitory concentration (IC50) of between about 0.001 to 5 µg/mL$^{-1}$, between about 0.001 to 4 µg/mL$^{-1}$ or between about 0.001 to 3 µg/mL$^{-1}$. Preferably, the antibody has an IC50 of between about 0.03 to 2 µg/mL, between about 0.03 to 1.0 µg/mL$^{-1}$. Even more preferably the antibody has an IC50 of between about 0.001 to 0.5 µg/mL$^{-1}$, between about 0.001 to 0.05 µg/mL$^{-1}$, or between about 0.001 to 0.03 µg/mL$^{-1}$. Even more preferably, the antibody has a IC50 of between about 0.01 and 0.5 µg/mL$^{-1}$, between about 0.1 and 0.5 µg/mL$^{-1}$, and between about 0.2 and 0.5 µg/mL$^{-1}$. Preferably, the antibody has a IC50 of between about 0.05 and 0.008 µg/mL$^{-1}$, and between about 0.04 and 0.008 µg/mL$^{-1}$. Most preferably the antibody has a IC50 of between about 0.03 to 1.08 µg/mL$^{-1}$, between about 0.007 to 0.027 µg ml$^{-1}$, between about 0.225 and 0.413 µg ml$^{-1}$ or between about 0.040 and 0.008 µg ml$^{-1}$ Specifically, the antibody of the invention of neutralize group 2 viruses (e.g. H3, H7, A/Wisconsin/67/05 (HA, NA)×A/Puerto Rico/8/34 and A/Aichi/2/68 (HA, NA) x A/Puerto Rico/8/34, and H7N9-AH13). The antibody of invention also neutralizes pseudoviruses H7N1-FPN and H7N1-NL219 strains. In addition, the antibodies of the invention neutralizes group 1 H1 stains (H1-CA09 and H1-PR8) and pseudoviruses H5-VN04 and H5-HK97

The antibody of the invention has prophylactic efficacy against both group 1 and group 2 influenza A viruses in vivo. The antibody of the invention provides 50%, 60%, 70%, 80%, 90%, 95% or 100% prophylactic protection against viral infection. Specifically the antibody of the invention fully protects from H7N7-NL219 or H7N9-AH13 challenge 80% protection against a H3N2-BR07 challenge and 60% protection against a H5N1-VN04 challenge.

The antibody of the invention prevents cleavage of immature HA0. If the HA0 protein is not cleaved to form HA' and HA2, virus-host membrane fusion cannot occur. Therefore influenza viruses with uncleaved HA are not infectious. Thus the antibodies of the invention are useful for blocking influenza infection and there for may be used in combination with other anti-viral agent, such as for example Tamiflu.

Importantly, the antibody of the invention binds uncleaved HA precursor (HA0) protein and the two mature forms HA1 protein and HA2 protein Additionally, the antibody of the invention prevents low pH-triggered HA conformational rearrangements.

The antibody mediates Fc-dependent viral clearance. In some embodiments, the antibody enhances antibody-dependent cellular cytotoxicity (ADCC). Alternatively, the antibody engages an Fc-dependent immune-mediated mechanism for in vivo protection.

The variable heavy chain of the antibody of the invention is encoded by the IGHV3-30 germline gene. The variable light chain of the antibody is encoded by the IGLV1-44 germline gene. IGHV3-30 antibodies use HCDR3 to form a hydrophobic core that contributes to HA binding. The antibody has a rearranged heavy chain such as to produce a long complementarity determining region 3 (HCDR3). The length of the long HCDR3 can be between about 12 to 30 amino acids (e.g. 12, 13, 14, 15, 16, 17, 18, 19, 20, 21, 22, 23, 24, 25, 26, 27, 28, 29, 30). In a preferred embodiment, the long HCDR 3 is about 23 amino acids in length. In some embodiments, the long HCDR3 uses the IGHD3-22*01 DH segment flanked by large N-additions at both VH and IGHJ4*02 junctions.

The antibody has somatic mutations in the variable heavy chain and/or the variable light chain. The number of somatic mutations in the variable heavy chain can be between about 2 to 30 (e.g. 2, 3, 4, 5, 6, 7, 8, 9, 10, 11, 12, 13, 14, 15, 16, 17, 18, 19, 20, 21, 22, 23, 24, 25, 26, 27, 28, 29, 30). In some embodiments, the number of somatic mutations in the variable heavy chain is about 15. The number of somatic mutations in the variable light chain can be between about 2 and 15 (e.g. 2, 3, 4, 5, 6, 7, 8, 9, 10, 11, 12, 13, 14, 15). In some embodiments, the number of somatic mutations is about 7.

Epitope mapping and competition assay revealed a highly conserved epitope located in the HA stem. For example, the antibodies of the invention bind a conformational epitope defined by amino acids residues 18, 19, 20, 21, 36, 38, 39, 41, 42, 45, 46, 49 and 53 of HA2 when numbered in accordance with SEQ ID NO: 18. Alternatively, the antibodies of the invention bind a conformational epitope defined by amino acids residues 18, 19, 20, 21, 38, 39, 41, 42, 45, 46, 47, 48, 49 and 50 of HA2 when numbered in accordance with SEQ ID NO: 18. Optionally, the antibody binds HA1.

The conserved epitope residue sequences is defined by peptides residues

Structure-bases antibody engineering has been used to optimize 3I14 to improve its potency against otherwise moderate subtype HA strain. This high affinity variant of 3I14 is referred to herein as 3I14VLD94N and was produced by an Aspartic acid (D) to Asparagine (N) amino acid substitution in the 3I14 VH at amino acid position 9.

The VLD94L substitution allows for or increases the antibody's binding to H5. The increase in binding affinity to H5 is between about 5 to 15-fold compared to wild-type 3I14. The Kd for the 3I14VLD94N to H5-VN04 is about less than 0.2 nM.

Additional structure based engineering can increase the binding affinity to H5 Specifically, increases binding affinity to H5 is achieved by substitution of glycine (G) at residue 31 in the LCDR1 with another amino acid. For example, glycine (G) at residue 31 can be substituted with a serine (S).

The nucleic acid and amino acid sequence of the neutralizing influenza antibodies according to the invention are provided below:

TABLE 1A

Antibody 3I14 Variable Region
nucleic acid sequences $V_H$ chain of 3I14 (SEQ ID NO: 1)

CAGGTGCAGCTGTTGGAGTCTGGGGGAGGCGTGGTCCAGCCTGGG
AGGTCCCTGAGACTCTCCTGTGCAGCCTCTGGATTCACCTTCAGT
AACTATGGCATGCACTGGGTCCGCCAGGCTCCAGGCAAGGGGCTG
GAGTGGGTGGCAATTATATCATTTGATGGAAGTAAAAAATATTAT
GCAAACTCCGTGAAGGGCCGATCCACCATCTCCAGAGACAATTCC
AAGAACACGCTGTCTCTGCAAATGAACAGCCTGGGACCTGAGGAC
ACGGCTCTATATTACTGTGCGAAACTGCCCTCCCCGTATTACTTT
GATAGTCGGTTCGTGTGGGTCGCCGCCAGCGCATTTCACTTCTGG
GGCCAGGGAATCCTGGTCACCGTCTCTTCA $V_L$ chain of 3I14 (SEQ ID NO: 3)

AATTTTATGCTGACTCAGCCACCCTCAGCGTCTGGGACCCCCGGG
CAGAGGGTCACCATCTCTTGCTCTGGAAGCAGCTCCAACATCGGA
GGTAATACTGTACACTGGTTCCAGCAGCTCCCAGGAACGGCCCCC
AAACTCCTCATCTATACTAATAGTCTGCGGCCCTCAGGGGTCCCT
GACCGATTCTCTGGCTCCAAGTCTGGCACCTCAGCCTCCCTGGCC
ATCAGTGGGCTCCAGTCTGAGGATGAGGCTGATTATTACTGTGCA
GCATGGGATGACAGCCTAAATGGTCAGGTGTTCGGCGGAGGGACC
AAGCTGACCGTCCTA

TABLE 1B

Antibody 3I14 Variable Region amino acid sequences $V_H$ chain of 3I14 (SEQ ID NO: 2)

QVQLLESGGGVVQPGRSLRLSCAASGFTFSNYGMHWVRQAPGKGLEWVA
IISFDGSKKYYANSVKGRSTISRDNSKNTLSLQMNSLGPEDTALYYCAK
LPSPYYFDSRFVWVAASAFHFWGQGILVTVSS

TABLE 1B-continued

Antibody 3I14 Variable Region amino acid sequences $V_L$ chain of 3I14 (SEQ ID NO: 4)

NFMLTQPPSASGTPGQRVTISCSGSSSNIGGNTVHWFQQLPGTAPKLLI
YTNSLRPSGVPDRFSGSKSGTSASLAISGLQSEDEADYYCAAWDDSLNG
QVFGGGTKLTVL

TABLE 1C

Antibody 3I14$V_L$D94N Variable Region
nucleic acid sequence $V_L$ chain of 3I14$V_L$D94N (SEQ ID NO: 5)

AATTTTATGCTGACTCAGCCACCCTCAGCGTCTGGGACCCCCGGGCAG
AGGGTCACCATCTCTTGCTCTGGAAGCAGCTCCAACATCGGAGGTAAT
ACTGTACACTGGTTCCAGCAGCTCCCAGGAACGGCCCCCAAACTCCTC
ATCTATACTAATAGTCTGCGGCCCTCAGGGGTCCCTGACCGATTCTCT
GGCTCCAAGTCTGGCACCTCAGCCTCCCTGGCCATCAGTGGGCTCCAG
TCTGAGGATGAGGCTGATTATTACTGTGCAGCATGGGATAACAGCCTAA
ATGGTCAGGTGTTCGGCGGAGGGACCAAGCTGACCGTCCTA $V_L$ chain of 3I14$V_L$D94N (SEQ ID NO: 6)

NFMLTQPPSASGTPGQRVTISCSGSSSNIGGNTVHWFQQLPGTAPKLL
IYTNSLRPSGVPDRFSGSKSGTSASLAISGLQSEDEADYYCAAWDNSL
NGQVFGGGTKLTVL

TABLE 8

Nucleic Acid Sequences of
IGHV3-03*18 and IGLV1-44*01

IGHV3-30*18-nucleic acid sequence-
SEQ ID NO: 21

CATGGAGTTTGGGCTGAGCTGGGTTTTCCTCGTTGCTCTTTTAAGAGG
TGATTCATGGAGAAATAGAGAGACTGAGTGTGAGTGAACATGAGTGAG
AAAAACTGGATTTGTGTGGCATTTTCTGATAACGGTGTCCTTCTGTTT
GCAGGTGTCCAGTGTCAGGTGCAGCTGGTGGAGTCTGGGGGAGGCGTG
GTCCAGCCTGGGAGGTCCCTGAGACTCTCCTGTGCAGCCTCTGGATTC
ACCTTCAGTAGCTATGGCATGCACTGGGTCCGCCAGGCTCCAGGCAAG
GGGCTGGAGTGGGTGGCAGTTATATCATATGATGGAAGTAATAAATAC
TATGCAGACTCCGTGAAGGGCCGATTCACCATCTCCAGAGACAATTCC
AAGAACACGCTGTATCTGCAAATGAACAGCCTGAGAGCTGAGGACACG
GCTGTGTATTACTGTGCGAAAGACACAGTGAGGGGAAGTCATTGTGCG
CCCAGACACAAACCTCCCTGCAGGAACGCTGGCGGGAAATCAGCGGCA
GGGGGCGCTCAGGAGCCACTGATCAGAGTCAGCCCTAGAGGCAGGTGC
AGATGGAGGCTGTTTCCTGTCAGGATGTGGGACTTTGTCTTCTTCTGA
CAGTTCCCCAAGGAACCTCTTAAATTTAGAAAACTGTGCCTAACAATG

TABLE 8-continued

Nucleic Acid Sequences of
IGHV3-03*18 and IGLV1-44*01

TCTTCTCTATGCATATGAGGACCTTTTCTCCCTAGCACAAAATGCAGA

TTGACGCTGACACGGATGAAAATTCCTCAACCATG

IGHV3-30*18-Amino acid sequence-
SEQ ID NO: 22

VISYDGSNKYYADSVKGRLTISRDNSKNTLYLQMNSLRAEDTAVYYCA

KDFGPKRPTGDYFDYWGQ

IGLV1-44*01-Nucleic Acid Sequence-
SEQ ID NO: 23

CAGTCTGTGCTGACTCAGCCACCCTCAGCGTCTGGGACCCCCGGGCAG

AGGGTCACCATCTCTTGTTCTGGAAGCAGCTCCAACATCGGAAGTAAT

ACTGTAAACTGGTACCAGCAGCTCCCAGGAACGGCCCCCAAACTCCTC

ATCTATAGTAATAATCAGCGGCCCTCAGGGGTCCCTGACCGATTCTCT

GGCTCCAAGTCTGGCACCTCAGCCTCCCTGGCCATCAGTGGGCTCCAG

TCTGAGGATGAGGCTGATTATTACTGTGCAGCATGGGATGACAGCCTG

AATGGTCC

IGLV1-44*01-Nucleic Acid Sequence
SEQ ID NO: 24

QSVLTQPPSASGTPGQRVTISCSGSSSNIGSNTVNWYQQLPGTAPKLL

IYSNNQRPSGVPDRFSGSKSGTSASLAISGLQSEDEADYYCAAWDDSL

NG

The amino acid sequences of the heavy and light chain complementary determining regions of the 3I14 and 3I14VLD94N neutralizing influenza antibodies are shown in Table 2 below

TABLE 2

| HCDR1 | GFTFSNYG | (SEQ ID NO: 7) |
| HCDR2 | ISFDGSKK | (SEQ ID NO: 8) |
| HCDR3 | CAKLPSPYYFDSRFVWVAASAFHFW | (SEQ ID NO: 9) |
| LCDR1 | SSNIGGNT | (SEQ ID NO: 10) |
| LCDR2 | TNS | (SEQ ID NO: 11) |
| LCDR3 | CAAWDDSLNGQVF | (SEQ ID NO: 12) |
| 3I14$V_L$D94N LCDR3 | CAAWDNSLNGQVF | (SEQ ID NO: 13) |
| 3I14 G31X LCDR1 | SSNIGX[1]NT | (SEQ ID NO: 14) |

[1]X can be any amino acid other than glycine. Preferably X is a serine.

TABLE 9

Hemagglutinin nucleic acid and amino acid sequences

A/Japan/305/1957(H2N2)-HA1 amino acid sequence-
SEQ ID NO: 15

DQICIGYHANNSTEKVDTNLERNVTVTHAKDILEKTHNGKLCKLNGIPP

LELGDCSIAGWLLGNPECDRLLSVPEWSYIMEKENPRDGLCYPGSFNDY

EELKHLLSSVKHFEKVKILPKDRWTQHTTTGGSRACAVSGNPSFFRNMV

WLTKEGSDYPVAKGSYNNTSGEQMLIIWGVHHPIDETEQRTLYQNVGTY

VSVGTSTLNKRSTPEIATRPKVNGQGGRMEFSWTLLDMWDTINFESTGN

LIAPEYGFKISKRGSSGIMKTEGTLENCETKCQTPLGAINTTLPFHNVH

PLTIGECPKYVKSEKLVLATGLRNVPQIES

A/Japan/305/1957(H2N2)-HA1 nucleic acid sequence-
SEQ ID NO: 16

GACCAGATATGCATTGGATACCATGCCAATAATTCCACAGAGATGGTCG

ACACAATTCTAGAGCGGAACGTCACTGTGACTCATGCCAAGGACATTCT

TGAGAAGACCCATAACGGAAAGTTATGCAAACTAAACGGAATCCCTCCA

CTTGAACTAGGGGACTGTAGCATTGCCGGATGGCTCCTTGGAAATCCAG

AATGTGATAGGCTTCTAAGTGTGCCAGAATGGTCCTATATAATGGAGAA

AGAAAACCCGAGAGACGGTTTGTGTTATCCAGGCAGCTTCAATGATTAT

GAAGAATTGAAACATCTCCTCAGCAGCGTGAAACATTTCGAGAAAGTAA

AGATTCTGCCCAAAGATAGATGGACACAGCATACAACAACTGGAGGTTC

ACGGGCCTGCGCGGTGTCTGGTAATCCATCATTCTTCAGGAACATGGTC

TGGCTGACAAAGAAAGGATCAGATTATCCGGTTGCCAAAGGATCGTACA

ACAATACAAGCGGAGAACAAATGCTAATAATTTGGGGGGTGCACCATCC

CAATGATGAGACAGAACAAAGAACATTGTACCAGAATGTGGGAACCTAT

GTTTCCGTAGGCACATCAACATTGAACAAAAGGTCAACCCCAGAAATAG

CAACAAGGCTTAAAGTGAATGGACAAGGAGGTAGAATGGAATTCTCTTG

GACCCTCTTGGATATGTGGGACACCATAAATTTTGAGAGTACTGGTAAT

CTAATTGCACCAGAGTATGGATTCAAAATATCGAAAAGAGGTAGTTCAG

GGATCATGAAAACAGAAGGAACACTTGAGAACTGTGAGACCAAATGCCA

AACTCCTTTGGGAGCAATAAATACAACATTGCCTTTTCACAATGTCCAC

CCACTGACAATAGGTGAGTGCCCCAAATATGTAAAATCGGAGAAGTTGG

TCTTAGCAACAGGACTAAGGAATGTTCCCCAGATTGAATCAAG

A/Japan/305/1957(H2N2)-HA2 amino acid sequence-
SEQ ID NO: 17

GLFGAIAGFIEGGWQGMVDGWYGYHHSNDQGSGYAADKESTQKAFDGIT

NKVNSVIEKMNTQFEAVGKEFGNLERRLENLNKRMEDGFLDVWTYNAEL

LVLMENERTLDFHDSNVKNLYDKVRMQLRDNVKELGNGCFEFYHKCDDE

CMNSVKNGTYDYPKYEEESKLNRNEIKGVKLSSMGVYQILAIYATVAGS

LSLAIMMAGISFWMCSNGSLQCRICI

TABLE 9-continued

Hemagglutinin nucleic acid and amino acid sequences

A/Japan/305/1957(H2N2)-HA2 nucleic acid sequence-SEQ ID NO: 18

GATTGTTTGGGGCAATAGCTGGTTTTATAGAAGGAGGATGGCAAGGAAT

GGTTGATGGTTGGTATGGATACCATCACAGCAATGACCAGGGATCAGGG

TATGCAGCAGACAAAGAATCCACTCAAAAGGCATTTGATGGAATCACCA

ACAAGGTAAATTCTGTGATTGAAAAGATGAACACCCAATTTGAAGCTGT

TGGGAAAGAATTCAGTAACTTAGAGAGAAGACTGGAGAACTTGAACAAA

AAGATGGAAGACGGGTTTCTAGATGTGTGGACATACAATGCTGAGCTTC

TAGTTCTGATGGAAAATGAGAGGACACTTGACTTTCATGATTCTAATGT

CAAGAATCTGTATGATAAAGTCAGAATGCAGTTGAGAGACAACGTCAAA

GAACTAGGAAATGGATGTTTTGAATTTTATCACAAATGTGATGATGAAT

GCATGAATAGTGTGAAAACCGGGACGTATGATTATCCCAAGTATGAAGA

AGAGTCTAAACTAAATAGAAATGAAATCAAAGGGGTAAAATTGAGCAGC

ATGGGGGTTTATCAAATCCTTGCCATTTATGCTACAGTAGCAGGTTCTC

TGTCACTGGCAATCATGATGGCTGGGATCTCTTTCTGGATGTGCTCCAA

CGGGTCTCTGCAGTGCAGGATCTGCATATGA

A/Japan/305/1957(H2N2)-Full HA amino acid sequence-SEQ ID NO: 19

MAIIYLILLFTAVRGDQICIGYHANNSTEMVDTILERNVTVTHAKDILE

KTHNGKLCKLNGIPPLELGDCSIAGWLLGNPECDRLLSVPEWSYIMEKE

NPRDGLCYPGSFNDYEELKHLLSSVKHFEKVKILPKDRWTQ chemically separated, light and heavy polypeptide chains from an antibody V region into an scFv molecule, which will fold into a three dimensional structure substantially similar to the structure of an antigen-binding site. See, e.g., U.S. Pat. Nos. 5,091,513; 5,132,405; and 4,946,778.

Very large naïve human scFv libraries have been and can be created to offer a large source of rearranged antibody genes against a plethora of target molecules. Smaller libraries can be constructed from individuals with infectious diseases in order to isolate disease-specific antibodies. (See Barbas et al., Proc. Natl. Acad. Sci. USA 89:9339-43 (1992); Zebedee et al., Proc. Natl. Acad. Sci. USA 89:3175-79 (1992)).

In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, IgG2, IgG3, IgG4, and others. Furthermore, in humans, the light chain may be a kappa chain or a lambda chain. Preferably the antibody is $IgG_1$ or $IgG_4$.

The antibody is a chimeric antibody. Chimeric antibodies are produced by pairing mature antibody heavy chain with germline light chain (mHgL) or by pairing germline heavy chain with mature light chain (gHmL). The chimeric antibodies have increased binding affinity (Kd) in comparison to the wild type (WT) antibody. For example, the binding affinity of the mHgL and gHmL chimeric variants to certain viruses (e.g. H1-CA09) can have a binding affinity of about less than 0.001 nM. Alternatively, the binding affinity (Kd) of the mHgL and gHmL chimeric variants is less than is found in the WT antibody (e.g. for viruses H5-VN04 and H3-PE09). Optionally, the binding affinity of the mHgL and gHmL chimeric variants is about the same as the binding affinity of the WT antibody.

The term "antigen-binding site" or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs."

As used herein, the term "epitope" includes any protein determinant capable of specific binding to an immunoglobulin, an scFv, or a T-cell receptor. Epitopic determinants usually consist of chemically active surface groupings of molecules such as amino acids or sugar side chains and usually have specific three dimensional structural characteristics, as well as specific charge characteristics. For example, antibodies may be raised against N-terminal or C-terminal peptides of a polypeptide.

As used herein, the terms "immunological binding," and "immunological binding properties" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473). An antibody of the present invention is said to specifically bind to a influenza epitope when the equilibrium binding constant ($K_d$) is 1 μM, preferably 100 nM, more preferably 10 nM, and most preferably 100 μM to about 1 μM, as measured by assays such as radioligand binding assays or similar assays known to those skilled in the art.

An influenza protein (e.g., HA or neuramindase) of the invention, or a derivative, fragment, analog, homolog or ortholog thereof, may be utilized as an immunogen in the generation of antibodies that immunospecifically bind these protein components.

Those skilled in the art will recognize that it is possible to determine, without undue experimentation, if a human monoclonal antibody has the same specificity as a human monoclonal antibody of the invention by ascertaining whether the former prevents the latter from binding to the HA protein of the influenza virus. If the human monoclonal antibody being tested competes with the human monoclonal antibody of the invention, as shown by a decrease in binding by the human monoclonal antibody of the invention, then it is likely that the two monoclonal antibodies bind to the same, or to a closely related, epitope.

Another way to determine whether a human monoclonal antibody has the specificity of a human monoclonal antibody of the invention is to pre-incubate the human monoclonal antibody of the invention with the influenza HA protein, with which it is normally reactive, and then add the human monoclonal antibody being tested to determine if the human monoclonal antibody being tested is inhibited in its ability to bind the HA protein. If the human monoclonal antibody being tested is inhibited then, in all likelihood, it has the same, or functionally equivalent, epitopic specificity as the monoclonal antibody of the invention. Screening of human monoclonal antibodies of the invention, can be also carried out by utilizing the influenza virus and determining whether the test monoclonal antibody is able to neutralize the influenza virus.

Various procedures known within the art may be used for the production of polyclonal or monoclonal antibodies directed against a protein of the invention, or against derivatives, fragments, analogs homologs or orthologs thereof (See, for example, Antibodies: A Laboratory Manual, Harlow E, and Lane D, 1988, Cold Spring Harbor Laboratory Press, Cold Spring Harbor, N.Y., incorporated herein by reference).

Antibodies can be purified by well-known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25-28).

The term "monoclonal antibody" or "MAb" or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

Monoclonal antibodies can be prepared using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the protein antigen, a fragment thereof or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, *Monoclonal Antibodies: Principles and Practice*, Academic Press, (1986) pp. 59-103). Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies. (See Kozbor, J. Immunol., 133:3001 (1984); Brodeur et al., Monoclonal Antibody Production Techniques and Applications, Marcel Dekker, Inc., New York, (1987) pp. 51-63)).

The culture medium in which the hybridoma cells are cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, Anal. Biochem., 107:220 (1980). Moreover, in therapeutic applications of monoclonal antibodies, it is important to identify antibodies having a high degree of specificity and a high binding affinity for the target antigen.

After the desired hybridoma cells are identified, the clones can be subcloned by limiting dilution procedures and grown by standard methods. (See Goding, *Monoclonal Antibodies: Principles and Practice*, Academic Press, (1986) pp. 59-103). Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

Monoclonal antibodies can also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (see U.S. Pat. No. 4,816,567; Morrison, Nature 368, 812-13 (1994)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

Fully human antibodies are antibody molecules in which the entire sequence of both the light chain and the heavy chain, including the CDRs, arise from human genes. Such antibodies are termed "human antibodies", or "fully human antibodies" herein. Human monoclonal antibodies can be prepared by using trioma technique; the human B-cell hybridoma technique (see Kozbor, et al., 1983 Immunol Today 4: 72); and the EBV hybridoma technique to produce human monoclonal antibodies (see Cole, et al., 1985 In: MONOCLONAL ANTIBODIES AND CANCER THERAPY, Alan R. Liss, Inc., pp. 77-96). Human monoclonal antibodies may be utilized and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96).

In addition, human antibodies can also be produced using additional techniques, including phage display libraries. (See Hoogenboom and Winter, J. Mol. Biol., 227:381

(1991); Marks et al., J. Mol. Biol., 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in Marks et al., Bio/Technology 10, 779-783 (1992); Lonberg et al., Nature 368 856-859 (1994); Morrison, Nature 368, 812-13 (1994); Fishwild et al, Nature Biotechnology 14, 845-51 (1996); Neuberger, Nature Biotechnology 14, 826 (1996); and Lonberg and Huszar, Intern. Rev. Immunol. 13 65-93 (1995).

Human antibodies may additionally be produced using transgenic nonhuman animals which are modified so as to produce fully human antibodies rather than the animal's endogenous antibodies in response to challenge by an antigen. (See PCT publication WO94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. The preferred embodiment of such a nonhuman animal is a mouse, and is termed the Xenomouse™ as disclosed in PCT publications WO 96/33735 and WO 96/34096. This animal produces B cells which secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies.

Additionally, the genes encoding the immunoglobulins with human variable regions can be recovered and expressed to obtain the antibodies directly, or can be further modified to obtain analogs of antibodies such as, for example, single chain Fv (scFv) molecules.

An example of a method of producing a nonhuman host, exemplified as a mouse, lacking expression of an endogenous immunoglobulin heavy chain is disclosed in U.S. Pat. No. 5,939,598. It can be obtained by a method, which includes deleting the J segment genes from at least one endogenous heavy chain locus in an embryonic stem cell to prevent rearrangement of the locus and to prevent formation of a transcript of a rearranged immunoglobulin heavy chain locus, the deletion being effected by a targeting vector containing a gene encoding a selectable marker; and producing from the embryonic stem cell a transgenic mouse whose somatic and germ cells contain the gene encoding the selectable marker.

One method for producing an antibody of interest, such as a human antibody, is disclosed in U.S. Pat. No. 5,916,771. This method includes introducing an expression vector that contains a nucleotide sequence encoding a heavy chain into one mammalian host cell in culture, introducing an expression vector containing a nucleotide sequence encoding a light chain into another mammalian host cell, and fusing the two cells to form a hybrid cell. The hybrid cell expresses an antibody containing the heavy chain and the light chain.

In a further improvement on this procedure, a method for identifying a clinically relevant epitope on an immunogen, and a correlative method for selecting an antibody that binds immunospecifically to the relevant epitope with high affinity, are disclosed in PCT publication WO 99/53049.

The antibody can be expressed by a vector containing a DNA segment encoding the single chain antibody described above.

These can include vectors, liposomes, naked DNA, adjuvant-assisted DNA, gene gun, catheters, etc. Vectors include chemical conjugates such as described in WO 93/64701, which has targeting moiety (e.g. a ligand to a cellular surface receptor), and a nucleic acid binding moiety (e.g. polylysine), viral vector (e.g. a DNA or RNA viral vector), fusion proteins such as described in PCT/US 95/02140 (WO 95/22618) which is a fusion protein containing a target moiety (e.g. an antibody specific for a target cell) and a nucleic acid binding moiety (e.g. a protamine), plasmids, phage, etc. The vectors can be chromosomal, non-chromosomal or synthetic.

Preferred vectors include viral vectors, fusion proteins and chemical conjugates. Retroviral vectors include moloney murine leukemia viruses. DNA viral vectors are preferred. These vectors include pox vectors such as orthopox or avipox vectors, herpesvirus vectors such as a herpes simplex I virus (HSV) vector (see Geller, A. I. et al., J. Neurochem, 64:487 (1995); Lim, F., et al., in DNA Cloning: Mammalian Systems, D. Glover, Ed. (Oxford Univ. Press, Oxford England) (1995); Geller, A. I. et al., Proc Natl. Acad. Sci.: U.S.A. 90:7603 (1993); Geller, A. I., et al., Proc Natl. Acad. Sci USA 87:1149 (1990), Adenovirus Vectors (see LeGal LaSalle et al., Science, 259:988 (1993); Davidson, et al., Nat. Genet 3:219 (1993); Yang, et al., J. Virol. 69:2004 (1995) and Adeno-associated Virus Vectors (see Kaplitt, M. G. et al., Nat. Genet. 8:148 (1994).

Pox viral vectors introduce the gene into the cells cytoplasm. Avipox virus vectors result in only a short term expression of the nucleic acid. Adenovirus vectors, adeno-associated virus vectors and herpes simplex virus (HSV) vectors are preferred for introducing the nucleic acid into neural cells. The adenovirus vector results in a shorter term expression (about 2 months) than adeno-associated virus (about 4 months), which in turn is shorter than HSV vectors. The particular vector chosen will depend upon the target cell and the condition being treated. The introduction can be by standard techniques, e.g. infection, transfection, transduction or transformation. Examples of modes of gene transfer include e.g., naked DNA, $CaPO_4$ precipitation, DEAE dextran, electroporation, protoplast fusion, lipofection, cell microinjection, and viral vectors.

The vector can be employed to target essentially any desired target cell. For example, stereotaxic injection can be used to direct the vectors (e.g. adenovirus, HSV) to a desired location. Additionally, the particles can be delivered by intracerebroventricular (icy) infusion using a minipump infusion system, such as a SynchroMed Infusion System. A method based on bulk flow, termed convection, has also proven effective at delivering large molecules to extended areas of the brain and may be useful in delivering the vector to the target cell. (See Bobo et al., Proc. Natl. Acad. Sci. USA 91:2076-2080 (1994); Morrison et al., Am. J. Physiol. 266:292-305 (1994)). Other methods that can be used include catheters, intravenous, parenteral, intraperitoneal and subcutaneous injection, and oral or other known routes of administration.

These vectors can be used to express large quantities of antibodies that can be used in a variety of ways. For example, to detect the presence of an influenza virus in a sample. The antibody can also be used to try to bind to and disrupt influenza virus cell membrane fusion.

Techniques can be adapted for the production of single-chain antibodies specific to an antigenic protein of the invention (see e.g., U.S. Pat. No. 4,946,778). In addition, methods can be adapted for the construction of $F_{ab}$ expression libraries (see e.g., Huse, et al., 1989 Science 246: 1275-1281) to allow rapid and effective identification of monoclonal $F_{ab}$ fragments with the desired specificity for a protein or derivatives, fragments, analogs or homologs thereof. Antibody fragments that contain the idiotypes to a protein antigen may be produced by techniques known in the art including, but not limited to: (i) an $F_{(ab')2}$ fragment produced by pepsin digestion of an antibody molecule; (ii) an $F_{ab}$ fragment generated by reducing the disulfide bridges of an $F_{(ab')2}$ fragment; (iii) an $F_{ab}$ fragment generated by the treatment of the antibody molecule with papain and a reducing agent and (iv) $F_v$ fragments.

Heteroconjugate antibodies are also within the scope of the present invention. Heteroconjugate antibodies are composed of two covalently joined antibodies. Such antibodies have, for example, been proposed to target immune system cells to unwanted cells (see U.S. Pat. No. 4,676,980), and for treatment of HIV infection (see WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

It can be desirable to modify the antibody of the invention with respect to effector function, so as to enhance, e.g., the effectiveness of the antibody in treating influenza. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). (See Caron et al., J. Exp Med., 176: 1191-1195 (1992) and Shopes, J. Immunol., 148: 2918-2922 (1992)). Alternatively, an antibody can be engineered that has dual Fc regions and can thereby have enhanced complement lysis and ADCC capabilities. (See Stevenson et al., Anti-Cancer Drug Design, 3: 219-230 (1989)).

The invention also pertains to immunoconjugates comprising an antibody conjugated to a cytotoxic agent such as a toxin (e.g., an enzymatically active toxin of bacterial, fungal, plant, or animal origin, or fragments thereof), or a radioactive isotope (i.e., a radioconjugate).

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. (See WO94/11026).

Those of ordinary skill in the art will recognize that a large variety of possible moieties can be coupled to the resultant antibodies or to other molecules of the invention. (See, for example, "Conjugate Vaccines", Contributions to Microbiology and Immunology, J. M. Cruse and R. E. Lewis, Jr (eds), Carger Press, New York, (1989), the entire contents of which are incorporated herein by reference).

Coupling may be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. The preferred binding is, however, covalent binding. Covalent binding can be achieved either by direct condensation of existing side chains or by the incorporation of external bridging molecules. Many bivalent or polyvalent linking agents are useful in coupling protein molecules, such as the antibodies of the present invention, to other molecules. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents. (See Killen and Lindstrom, Jour. Immun. 133:1335-2549 (1984); Jansen et al., Immunological Reviews 62:185-216 (1982); and Vitetta et al., Science 238:1098 (1987)).

Preferred linkers are described in the literature. (See, for example, Ramakrishnan, S. et al., Cancer Res. 44:201-208 (1984) describing use of MBS (M-maleimidobenzoyl-N-hydroxysuccinimide ester). See also, U.S. Pat. No. 5,030, 719, describing use of halogenated acetyl hydrazide derivative coupled to an antibody by way of an oligopeptide linker. Particularly preferred linkers include: (i) EDC (1-ethyl-3-(3-dimethylamino-propyl) carbodiimide hydrochloride; (ii) SMPT (4-succinimidyloxycarbonyl-alpha-methyl-alpha-(2-pridyl-dithio)-toluene (Pierce Chem. Co., Cat. (21558G); (iii) SPDP (succinimidyl-6 [3-(2-pyridyldithio) propionamido]hexanoate (Pierce Chem. Co., Cat #21651G); (iv) Sulfo-LC-SPDP (sulfosuccinimidyl 6 [3-(2-pyridyldithio)-propianamide] hexanoate (Pierce Chem. Co. Cat. #2165-G); and (v) sulfo-NHS (N-hydroxysulfo-succinimide: Pierce Chem. Co., Cat. #24510) conjugated to EDC.

The linkers described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

The antibodies disclosed herein can also be formulated as immunoliposomes. Liposomes containing the antibody are prepared by methods known in the art, such as described in Epstein et al., Proc. Natl. Acad. Sci. USA, 82: 3688 (1985); Hwang et al., Proc. Natl Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem., 257: 286-288 (1982) via a disulfide-interchange reaction.

Use of Antibodies Against Influenza Virus

Methods for the screening of antibodies that possess the desired specificity include, but are not limited to, enzyme linked immunosorbent assay (ELISA) and other immunologically mediated techniques known within the art.

Antibodies directed against a influenza virus protein such as HA (or a fragment thereof) may be used in methods known within the art relating to the localization and/or quantitation of a influenza virus protein (e.g., for use in measuring levels of the influenza virus protein within appropriate physiological samples, for use in diagnostic methods, for use in imaging the protein, and the like). In a given embodiment, antibodies specific to an influenza virus protein, or derivative, fragment, analog or homolog thereof, that contain the antibody derived antigen binding domain, are utilized as pharmacologically active compounds (referred to hereinafter as "Therapeutics").

An antibody specific for an influenza virus protein of the invention can be used to isolate an influenza virus polypeptide by standard techniques, such as immunoaffinity, chromatography or immunoprecipitation. Antibodies directed against an influenza virus protein (or a fragment thereof) can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, □-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Antibodies of the invention, including polyclonal, monoclonal, humanized and fully human antibodies, may used as therapeutic agents. Such agents will generally be employed to treat or prevent an influenza virus-related disease or pathology (e.g., bird flu) in a subject. An antibody preparation, preferably one having high specificity and high affinity for its target antigen, is administered to the subject and will generally have an effect due to its binding with the target. Administration of the antibody may abrogate or inhibit or interfere with the internalization of the virus into a cell. In this case, the antibody binds to the target and masks a binding site of the naturally occurring ligand, thereby blocking fusion the virus to the cell membrane inhibiting internalization of the virus.

A therapeutically effective amount of an antibody of the invention relates generally to the amount needed to achieve a therapeutic objective. As noted above, this may be a binding interaction between the antibody and its target antigen that, in certain cases, interferes with the functioning of the target. The amount required to be administered will furthermore depend on the binding affinity of the antibody for its specific antigen, and will also depend on the rate at which an administered antibody is depleted from the free volume other subject to which it is administered. Common ranges for therapeutically effective dosing of an antibody or antibody fragment of the invention may be, by way of nonlimiting example, from about 0.1 mg/kg body weight to about 50 mg/kg body weight. Common dosing frequencies may range, for example, from twice daily to once a week.

Antibodies specifically binding an influenza virus protein or a fragment thereof of the invention, as well as other molecules identified by the screening assays disclosed herein, can be administered for the treatment of an influenza virus-related disorders in the form of pharmaceutical compositions. Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Easton, Pa., 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. (See, e.g., Marasco et al., Proc. Natl. Acad. Sci. USA, 90: 7889-7893 (1993)). The formulation can also contain more than one active compound as necessary for the particular indication being treated, preferably those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

The formulations to be used for in vivo administration must be sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

An antibody according to the invention can be used as an agent for detecting the presence of an influenza virus (or a protein or a protein fragment thereof) in a sample. Preferably, the antibody contains a detectable label. Antibodies can be polyclonal, or more preferably, monoclonal. An intact antibody, or a fragment thereof (e.g., $F_{ab}$, scFv, or $F_{(ab)2}$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. That is, the detection method of the invention can be used to detect an analyte mRNA, protein, or genomic DNA in a biological sample in vitro as well as in vivo. For example, in vitro techniques for detection of an analyte mRNA include Northern hybridizations and in situ hybridizations. In vitro techniques for detection of an analyte protein include enzyme linked immunosorbent assays (ELISAs), Western blots, immunoprecipitations, and immunofluorescence. In vitro techniques for detection of an analyte genomic DNA include Southern hybridizations. Procedures for conducting immunoassays are described, for example in "ELISA: Theory and Practice: Methods in Molecular Biology", Vol. 42, J. R. Crowther (Ed.) Human Press, Totowa, N.J., 1995; "Immunoassay", E. Diamandis and T. Christopoulus, Academic Press, Inc., San Diego, Calif., 1996; and "Practice and Theory of Enzyme Immunoassays", P. Tijssen, Elsevier Science Publishers, Amsterdam, 1985. Furthermore, in vivo techniques for detection of an analyte protein include introducing into a subject a labeled anti-analyte protein antibody. For example, the antibody can be labeled with a radioactive marker whose presence and location in a subject can be detected by standard imaging techniques.

Pharmaceutical Compositions

The antibodies or agents of the invention (also referred to herein as "active compounds"), and derivatives, fragments, analogs and homologs thereof, can be incorporated into pharmaceutical compositions suitable for administration. Such compositions typically comprise the antibody or agent and a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL□ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

Screening Methods

The invention provides methods (also referred to herein as "screening assays") for identifying modulators, i.e., candidate or test compounds or agents (e.g., peptides, peptidomimetics, small molecules or other drugs) that modulate or otherwise interfere with the fusion of an influenza virus to the cell membrane. Also provided are methods of identifying compounds useful to treat influenza infection. The invention also encompasses compounds identified using the screening assays described herein.

For example, the invention provides assays for screening candidate or test compounds which modulate the interaction between the influenza virus and the cell membrane. The test compounds of the invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds. (See, e.g., Lam, 1997. Anticancer Drug Design 12: 145).

A "small molecule" as used herein, is meant to refer to a composition that has a molecular weight of less than about 5 kD and most preferably less than about 4 kD. Small molecules can be, e.g., nucleic acids, peptides, polypeptides, peptidomimetics, carbohydrates, lipids or other organic or inorganic molecules. Libraries of chemical and/or biological mixtures, such as fungal, bacterial, or algal extracts, are known in the art and can be screened with any of the assays of the invention.

Examples of methods for the synthesis of molecular libraries can be found in the art, for example in: DeWitt, et al., 1993. Proc. Natl. Acad. Sci. U.S.A. 90: 6909; Erb, et al., 1994. Proc. Natl. Acad. Sci. U.S.A. 91: 11422; Zuckermann, et al., 1994. J. Med. Chem. 37: 2678; Cho, et al., 1993. Science 261: 1303; Carrell, et al., 1994. Angew. Chem. Int. Ed. Engl. 33: 2059; Carell, et al., 1994. Angew. Chem. Int. Ed. Engl. 33: 2061; and Gallop, et al., 1994. J. Med. Chem. 37: 1233.

Libraries of compounds may be presented in solution (see e.g., Houghten, 1992. Biotechniques 13: 412-421), or on beads (see Lam, 1991. Nature 354: 82-84), on chips (see Fodor, 1993. Nature 364: 555-556), bacteria (see U.S. Pat. No. 5,223,409), spores (see U.S. Pat. No. 5,233,409), plasmids (see Cull, et al., 1992. Proc. Natl. Acad. Sci. USA 89: 1865-1869) or on phage (see Scott and Smith, 1990. Science 249: 386-390; Devlin, 1990. Science 249: 404-406; Cwirla, et al., 1990. Proc. Natl. Acad. Sci. U.S.A. 87: 6378-6382; Felici, 1991. J. Mol. Biol. 222: 301-310; and U.S. Pat. No. 5,233,409).

In one embodiment, a candidate compound is introduced to an antibody-antigen complex and determining whether the candidate compound disrupts the antibody-antigen complex, wherein a disruption of this complex indicates that the candidate compound modulates the interaction between an influenza virus and the cell membrane.

In another embodiment, at least one HA protein is provided, which is exposed to at least one neutralizing monoclonal antibody. Formation of an antibody-antigen complex is detected, and one or more candidate compounds are introduced to the complex. If the antibody-antigen complex is disrupted following introduction of the one or more candidate compounds, the candidate compounds is useful to treat an influenza virus-related disease or disorder, e.g. bird flu. For example, the at least one influenza virus protein may be provided as an influenza virus molecule.

Determining the ability of the test compound to interfere with or disrupt the antibody-antigen complex can be accomplished, for example, by coupling the test compound with a radioisotope or enzymatic label such that binding of the test compound to the antigen or biologically-active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemission or by scintillation counting. Alternatively, test compounds can be enzymatically-labeled with, for example, horseradish peroxidase, alkaline phosphatase, or luciferase, and the enzymatic label detected by determination of conversion of an appropriate substrate to product.

In one embodiment, the assay comprises contacting an antibody-antigen complex with a test compound, and determining the ability of the test compound to interact with the antigen or otherwise disrupt the existing antibody-antigen complex. In this embodiment, determining the ability of the test compound to interact with the antigen and/or disrupt the antibody-antigen complex comprises determining the ability of the test compound to preferentially bind to the antigen or a biologically-active portion thereof, as compared to the antibody.

In another embodiment, the assay comprises contacting an antibody-antigen complex with a test compound and determining the ability of the test compound to modulate the antibody-antigen complex. Determining the ability of the test compound to modulate the antibody-antigen complex can be accomplished, for example, by determining the ability of the antigen to bind to or interact with the antibody, in the presence of the test compound.

Those skilled in the art will recognize that, in any of the screening methods disclosed herein, the antibody may be a an influenza virus neutralizing antibody. Additionally, the antigen may be a HA protein, or a portion thereof. In any of the assays described herein, the ability of a candidate compound to interfere with the binding between the monoclonal antibodies of the invention and the HA protein indicates that the candidate compound will be able to interfere with or modulate the fusion of the influenza virus and the cell membrane Moreover, because the binding of the HA protein to cell is responsible for influenza virus entry into cells such candidate compounds will also be useful in the treatment of a influenza virus related disease or disorder, e.g. bird flu.

The screening methods disclosed herein may be performed as a cell-based assay or as a cell-free assay. The cell-free assays of the invention are amenable to use of both the soluble form or the membrane-bound form of the HA proteins and fragments thereof. In the case of cell-free assays comprising the membrane-bound forms of the HA proteins, it may be desirable to utilize a solubilizing agent such that the membrane-bound form of the proteins are maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, N-dodecyl-N,N-dimethyl-3-ammonio-1-propane sulfonate, 3-(3-cholamidopropyl) dimethylamminiol-1-propane sulfonate (CHAPS), or 3-(3-cholamidopropyl)dimethylamminiol-2-hydroxy-1-propane sulfonate (CHAPSO).

In more than one embodiment, it may be desirable to immobilize either the antibody or the antigen to facilitate separation of complexed from uncomplexed forms of one or both following introduction of the candidate compound, as well as to accommodate automation of the assay. Observation of the antibody-antigen complex in the presence and absence of a candidate compound, can be accomplished in any vessel suitable for containing the reactants. Examples of such vessels include microtiter plates, test tubes, and micro-centrifuge tubes. In one embodiment, a fusion protein can be provided that adds a domain that allows one or both of the proteins to be bound to a matrix. For example, GST-antibody fusion proteins or GST-antigen fusion proteins can be adsorbed onto glutathione sepharose beads (Sigma Chemical, St. Louis, Mo.) or glutathione derivatized microtiter plates, that are then combined with the test compound, and the mixture is incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly. Alternatively, the complexes can be dissociated from the matrix, and the level of antibody-antigen complex formation can be determined using standard techniques.

Other techniques for immobilizing proteins on matrices can also be used in the screening assays of the invention. For example, either the antibody or the antigen (e.g. the can be immobilized utilizing conjugation of biotin and streptavidin. Biotinylated antibody or antigen molecules can be prepared from biotin-NHS (N-hydroxy-succinimide) using techniques well-known within the art (e.g., biotinylation kit, Pierce Chemicals, Rockford, Ill.), and immobilized in the wells of streptavidin-coated 96 well plates (Pierce Chemical). Alternatively, other antibodies reactive with the antibody or antigen of interest, but which do not interfere with the formation of the antibody-antigen complex of interest, can be derivatized to the wells of the plate, and unbound antibody or antigen trapped in the wells by antibody conjugation. Methods for detecting such complexes, in addition to those described above for the GST-immobilized complexes, include immunodetection of complexes using such other antibodies reactive with the antibody or antigen.

The invention further pertains to novel agents identified by any of the aforementioned screening assays and uses thereof for treatments as described herein.

Diagnostic Assays

Antibodies of the present invention can be detected by appropriate assays, e.g., conventional types of immunoassays. For example, a an assay can be performed in which a influenza protein (e.g., HA1, HA 2 or neurominidase) or fragment thereof is affixed to a solid phase. Incubation is maintained for a sufficient period of time to allow the antibody in the sample to bind to the immobilized polypeptide on the solid phase. After this first incubation, the solid phase is separated from the sample. The solid phase is washed to remove unbound materials and interfering substances such as non-specific proteins which may also be present in the sample. The solid phase containing the antibody of interest bound to the immobilized polypeptide is subsequently incubated with a second, labeled antibody or antibody bound to a coupling agent such as biotin or avidin. This second antibody may be another anti-influenza antibody or another antibody. Labels for antibodies are well-known in the art and include radionuclides, enzymes (e.g. maleate dehydrogenase, horseradish peroxidase, glucose oxidase, catalase), fluors (fluorescein isothiocyanate, rhodamine, phycocyanin, fluorescarmine), biotin, and the like. The labeled antibodies are incubated with the solid and the label bound to the solid phase is measured. These and other immunoassays can be easily performed by those of ordinary skill in the art.

An exemplary method for detecting the presence or absence of a influenza virus (in a biological sample involves obtaining a biological sample from a test subject and contacting the biological sample with a labeled monoclonal or scFv antibody according to the invention such that the presence of the influenza virus is detected in the biological sample.

As used herein, the term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. That is, the detection method of the invention can be used to detect an influenza virus in a biological sample in vitro as well as in vivo. For example, in vitro techniques for detection of an influenza virus include enzyme linked immunosorbent assays (ELISAs), Western blots, immunoprecipitations, and immunofluorescence. Furthermore, in vivo techniques for detection of an influenza virus include introducing into a subject a labeled anti-influenza virus antibody. For example, the antibody can be labeled with a radioactive marker whose presence and location in a subject can be detected by standard imaging techniques.

In one embodiment, the biological sample contains protein molecules from the test subject. One preferred biological sample is a peripheral blood leukocyte sample isolated by conventional means from a subject.

The invention also encompasses kits for detecting the presence of an influenza virus in a biological sample. For example, the kit can comprise: a labeled compound or agent capable of detecting an influenza virus (e.g., an anti-influenza scFv or monoclonal antibody) in a biological sample; means for determining the amount of an influenza virus in the sample; and means for comparing the amount of an influenza virus in the sample with a standard. The compound or agent can be packaged in a suitable container. The kit can further comprise instructions for using the kit to detect an influenza virus in a sample.

Passive Immunization

Passive immunization has proven to be an effective and safe strategy for the prevention and treatment of viral diseases. (See Keller et al., Clin. Microbiol. Rev. 13:602-14 (2000); Casadevall, Nat. Biotechnol. 20:114 (2002); Shibata et al., Nat. Med. 5:204-10 (1999); and Igarashi et al., Nat. Med. 5:211-16 (1999), each of which are incorporated herein by reference)). Passive immunization using neutralizing human monoclonal antibodies could provide an immediate treatment strategy for emergency prophylaxis and treatment of influenza such as bird flu while the alternative and more time-consuming development of vaccines and new drugs in underway.

Subunit vaccines potentially offer significant advantages over conventional immunogens. They avoid the safety hazards inherent in production, distribution, and delivery of conventional killed or attenuated whole-pathogen vaccines. Furthermore, they can be rationally designed to include only confirmed protective epitopes, thereby avoiding suppressive T epitopes (see Steward et al., J. Virol. 69:7668 (1995)) or immunodominant B epitopes that subvert the immune system by inducing futile, non-protective responses (e.g. "decoy" epitopes). (See Garrity et al., J. Immunol. 159:279 (1997)).

Moreover, those skilled in the art will recognize that good correlation exists between the antibody neutralizing activity in vitro and the protection in vivo for many different viruses, challenge routes, and animal models. (See Burton, Natl. Rev. Immunol. 2:706-13 (2002); Parren et al., Adv. Immunol. 77:195-262 (2001)). The data presented herein demonstrate that the D7, D8, F10, G17, H40, A66, D80, E88, E90, and H98 human monoclonal antibodies can be further developed and tested in in vivo animal studies to determine its clinical utility as a potent viral entry inhibitor for emergency prophylaxis and treatment of influenza.

Antigen-Ig Chimeras in Vaccination

It has been over a decade since the first antibodies were used as scaffolds for the efficient presentation of antigenic determinants to the immune systems. (See Zanetti, Nature 355:476-77 (1992); Zaghouani et al., Proc. Natl. Acad. Sci. USA 92:631-35 (1995)). When a peptide is included as an integral part of an IgG molecule (e.g., the 11A or 256 IgG1 monoclonal antibody described herein), the antigenicity and immunogenicity of the peptide epitopes are greatly enhanced as compared to the free peptide. Such enhancement is possibly due to the antigen-IgG chimeras longer half-life, better presentation and constrained conformation, which mimic their native structures.

Moreover, an added advantage of using an antigen-Ig chimera is that either the variable or the Fc region of the antigen-Ig chimera can be used for targeting professional antigen-presenting cells (APCs). To date, recombinant Igs have been generated in which the complementarity-determining regions (CDRs) of the heavy chain variable gene ($V_H$) are replaced with various antigenic peptides recognized by B or T cells. Such antigen-Ig chimeras have been used to induce both humoral and cellular immune responses. (See Bona et al., Immunol. Today 19:126-33 (1998)).

Chimeras with specific epitopes engrafted into the CDR3 loop have been used to induce humoral responses to either HIV-1 gp120 V3-loop or the first extracellular domain (D1) of human CD4 receptor. (See Lanza et al., Proc. Natl. Acad. Sci. USA 90:11683-87 (1993); Zaghouani et al., Proc. Natl. Acad. Sci. USA 92:631-35 (1995)). The immune sera were able to prevent infection of CD4 SupT1 cells by HIV-1MN (anti-gp120 V3C) or inhibit syncytia formation (anti-CD4-D1). The CDR2 and CDR3 can be replaced with peptide epitopes simultaneously, and the length of peptide inserted can be up to 19 amino acids long.

Alternatively, one group has developed a "troybody" strategy in which peptide antigens are presented in the loops of the Ig constant (C) region and the variable region of the chimera can be used to target IgD on the surface of B-cells or MHC class II molecules on professional APCs including B-cells, dendritic cells (DC) and macrophages. (See Lunde et al., Biochem. Soc. Trans. 30:500-6 (2002)).

An antigen-Ig chimera can also be made by directly fusing the antigen with the Fc portion of an IgG molecule. You et al., Cancer Res. 61:3704-11 (2001) were able to obtain all arms of specific immune response, including very high levels of antibodies to hepatitis B virus core antigen using this method.

DNA Vaccination

DNA vaccines are stable, can provide the antigen an opportunity to be naturally processed, and can induce a longer-lasting response. Although a very attractive immunization strategy, DNA vaccines often have very limited potency to induce immune responses. Poor uptake of injected DNA by professional APCs, such as dendritic cells (DCs), may be the main cause of such limitation. Combined with the antigen-Ig chimera vaccines, a promising new DNA vaccine strategy based on the enhancement of APC antigen presentation has been reported (see Casares, et al., Viral Immunol. 10:129-36 (1997); Gerloni et al., Nat. Biotech. 15:876-81 (1997); Gerloni et al., DNA Cell Biol. 16:611-25 (1997); You et al., Cancer Res. 61:3704-11 (2001)), which takes advantage of the presence of Fc receptors (Fc□Rs) on the surface of DCs.

It is possible to generate a DNA vaccine encoding an antigen (Ag)-Ig chimera. Upon immunization, Ag-Ig fusion proteins will be expressed and secreted by the cells taking up the DNA molecules. The secreted Ag-Ig fusion proteins, while inducing B-cell responses, can be captured and internalized by interaction of the Fc fragment with Fc□Rs on DC surface, which will promote efficient antigen presentation and greatly enhance antigen-specific immune responses. Applying the same principle, DNA encoding antigen-Ig chimeras carrying a functional anti-MHC II specific scFv region gene can also target the immunogens to all three types of APCs. The immune responses could be further boosted with use of the same protein antigens generated in vitro (i.e., "prime and boost"), if necessary. Using this strategy, specific cellular and humoral immune responses against infection of influenza virus were accomplished through intramuscular (i.m.) injection of a DNA vaccine. (See Casares et al., Viral. Immunol. 10:129-36 (1997)).

Vaccine Compositions

Therapeutic or prophylactic compositions are provided herein, which generally comprise mixtures of one or more monoclonal antibodies or ScFvs and combinations thereof. The prophylactic vaccines can be used to prevent an influenza virus infection and the therapeutic vaccines can be used to treat individuals following an influenza virus infection. Prophylactic uses include the provision of increased antibody titer to an influenza virus in a vaccination subject. In this manner, subjects at high risk of contracting influenza can be provided with passive immunity to an influenza virus These vaccine compositions can be administered in conjunction with ancillary immunoregulatory agents. For example, cytokines, lymphokines, and chemokines, including, but not limited to, IL-2, modified IL-2 (Cys125→Ser125), GM-CSF, IL-12, γ-interferon, IP-10, MIP1β, and RANTES.

Methods of Immunization

The vaccines of the present invention have superior immunoprotective and immunotherapeutic properties over other anti-viral vaccines The invention provides a method of immunization, e.g., inducing an immune response, of a subject. A subject is immunized by administration to the subject a composition containing a membrane fusion protein of a pathogenic enveloped virus. The fusion protein is coated or embedded in a biologically compatible matrix.

The fusion protein is glycosylated, e.g. contains acarbohydrate moiety. The carbohydrate moiety may be in the form of a monosaccharide, disaccharide(s). oligosaccharide(s), polysaccharide(s), or their derivatives (e.g. sulfo- or phospho-substituted). The carbohydrate is linear or branched. The carbohydrate moiety is N-linked or O-linked to a polypeptide. N-linked glycosylation is to the amide nitrogen of asparagine side chains and O-linked glycosylation is to the hydroxy oxygen of serine and threonine side chains.

The carbohydrate moiety is endogenous to the subject being vaccinated. Alternatively, the carbohydrate moiety is exogenous to the subject being vaccinated. The carbohydrate moiety are carbohydrate moieties that are not typically expressed on polypeptides of the subject being vaccinated. For example, the carbohydrate moieties are plant-specific carbohydrates. Plant specific carbohydrate moieties include for example N-linked glycan having a core bound α1,3 fucose or a core bound β1,2 xylose. Alternatively, the carbohydrate moiety are carbohydrate moieties that are expressed on polypeptides or lipids of the subject being vaccinate. For example many host cells have been genetically engineered to produce human proteins with human-like sugar attachments.

For example, the fusion protein is a trimeric hemagglutinin protein. Optionally, the hemagglutinin protein is produced in a non-mammalian cell such as a plant cell.

The subject is at risk of developing or suffering from a viral infection. Enveloped viruses include for example, epstein-barr virus, herpes simplex virus, type 1 and 2, human cytomegalovirus, human herpesvirus, type 8, varicella zoster virus, hepatitis B virus, hepatitis C virus, human immunodeficiency virus, influenza virus, measles virus, mumps virus, parainfluenza virus, respiratory syncytial virus, rabies virus, and rubella virus.

The methods described herein lead to a reduction in the severity or the alleviation of one or more symptoms of a viral infection. Infections are diagnosed and or monitored, typically by a physician using standard methodologies A subject requiring immunization is identified by methods know in the art. For example subjects are immunized as outlined in the CDC's General Recommendation on Immunization (51(RR02) pp 1-36) Cancer is diagnosed for example by physical exam, biopsy, blood test, or x-ray.

The subject is e.g., any mammal, e.g., a human, a primate, mouse, rat, dog, cat, cow, horse, pig, a fish or a bird. The treatment is administered prior to diagnosis of the infection. Alternatively, treatment is administered after diagnosis.

Efficaciousness of treatment is determined in association with any known method for diagnosing or treating the particular disorder or infection. Alleviation of one or more symptoms of the disorder indicates that the compound confers a clinical benefit.

Evaluation of Antigenic Protein Fragments (APFs) for Vaccine Potential

A vaccine candidate targeting humoral immunity must fulfill at least three criteria to be successful: it must provoke a strong antibody response ("immunogenicity"); a significant fraction of the antibodies it provokes must cross-react with the pathogen ("immunogenic fitness"); and the antibodies it provokes must be protective. While immunogenicity can often be enhanced using adjuvants or carriers, immunogenic fitness and the ability to induce protection (as evidenced by neutralization) are intrinsic properties of an antigen which will ultimately determine the success of that antigen as a vaccine component.

Evaluation of Immunogenic Fitness

"Immunogenic fitness" is defined as the fraction of antibodies induced by an antigen that cross-react with the pathogen. (See Matthews et al., J. Immunol. 169:837 (2002)). It is distinct from immunogenicity, which is gauged by the titer of all of the antibodies induced by an antigen, including those antibodies that do not cross-react with the pathogen. Inadequate immunogenic fitness has probably contributed to the disappointing track record of peptide vaccines to date. Peptides that bind with high affinity to antibodies and provoke high antibody titers frequently lack adequate immunogenic fitness, and, therefore, they fail as potential vaccine components. Therefore, it is important to include immunogenic fitness as one of the criteria for selecting influenza vaccine candidates.

A common explanation for poor immunogenic fitness is the conformational flexibility of most short peptides. Specifically, a flexible peptide may bind well to antibodies from patients, and elicit substantial antibody titers in naïve subjects. However, if the peptide has a large repertoire of conformations, a preponderance of the antibodies it induces in naïve subjects may fail to cross-react with the corresponding native epitope on intact pathogen.

Like short peptides, some APFs may be highly flexible and, therefore may fail as vaccine components. The most immunogenically fit APFs are likely to consist of self-folding protein subdomains that are intrinsically constrained outside the context of the whole protein.

Because immunogenic fitness is primarily a property of the APF itself, and not of the responding immune system, immunogenic fitness can be evaluated in an animal model (e.g. in mice) even though ultimately the APF will have to perform in humans.

The immunogenic fitness achieved by APFs is evaluated by immunosorption of anti-APF sera with purified spike or membrane protein, in a procedure analogous to that described in Matthews et al., J. Immunol. 169:837 (2002). IgG is purified from sera collected from mice that have been immunized. Purified, biotinylated proteins (as appropriate, depending on the particular APF with which the mice were immunized) are mixed with the mouse IgG and incubated. Streptavidin-coated sepharose beads are then added in sufficient quantity to capture all of the biotinylated protein, along with any bound IgG. The streptavidin-coated beads are removed by centrifugation at 13,000 rpm in a microcentrifuge, leaving IgG that has been depleted of antibodies directed against the protein, respectively. Mock immunoabsorptions are performed in parallel in the same way, except that biotinylated BSA will be substituted for influenza protein as a mock absorbent.

To measure the immunogenic fitness of APFs, the absorbed antibodies and the mock-absorbed antibodies are titered side-by-side in ELISA against the immunizing APF. For APFs affinity selected from a phage display NPL, the antigen for these ELISAs will be purified APF-GST fusion proteins. For the potentially glycosylated APFs from the mammalian cell display NPL, the antigen for these ELISAs will be APF-Fc fusion proteins secreted by mammalian cells and purified with protein A. The percentage decrease in the anti-APF titer of absorbed antibodies compared with the mock-absorbed antibodies will provide a measure of the immunogenic fitness of the APF.

Methods of Treatment

The invention provides for both prophylactic and therapeutic methods of treating a subject at risk of (or susceptible to) an influenza virus-related disease or disorder. Such diseases or disorders include but are not limited to, e.g., bird flu.

Prophylactic Methods

In one aspect, the invention provides methods for preventing an influenza virus-related disease or disorder in a subject by administering to the subject a monoclonal antibody or scFv antibody of the invention or an agent identified according to the methods of the invention. For example, scFv and/or monoclonal antibody may be administered in therapeutically effective amounts. Optionally, two or more anti-influenza antibodies are co-administered.

Subjects at risk for an influenza virus-related diseases or disorders include patients who have come into contact with an infected person or who have been exposed to the influenza virus in some other way. Administration of a prophylactic agent can occur prior to the manifestation of symptoms characteristic of the influenza virus-related disease or disorder, such that a disease or disorder is prevented or, alternatively, delayed in its progression.

The appropriate agent can be determined based on screening assays described herein. Alternatively, or in addition, the agent to be administered is a scFv or monoclonal antibody that neutralizes an influenza virus that has been identified according to the methods of the invention.

Therapeutic Methods

Another aspect of the invention pertains to methods of treating an influenza virus-related disease or disorder in a patient. In one embodiment, the method involves administering an agent (e.g., an agent identified by a screening assay described herein and/or an scFv antibody or monoclonal antibody identified according to the methods of the invention), or combination of agents that neutralize the influenza to a patient suffering from the disease or disorder. For example, the antibodies of the invention may be used in combination with other anti-viral agents such as for example Tamiflu.

The invention will be further described in the following examples, which do not limit the scope of the invention described in the claims.

Examples

Example 1: Isolation of bnAbs Against Influenza Viruses from Cultures of Single Memory B Cells A schematic representation of the broadly neutralizing antibody (BnAb) isolation procedure is depicted in FIG. 1. To isolate bnAbs against influenza viruses from human memory B cell repertoire, we established a rapid and reliable culture method, which allowed for human memory B cell activation and differentiation in vitro. Antigen-specific human memory B cells (CD19+CD27+) were isolated from peripheral blood mononuclear cells (PBMCs) of 7 healthy donors using tetramerized H3 (A/Brisbane/10/07) trimers; only 0.19%-1.08% of memory B cells were reactive with H3 (Table 3). These B cells were sorted into 384-well plates at the density of one cell per well and cultured in the presence of irradiated CD40L-transfected cells. After 14 days, 1051 (39.1% in 2688 cultures) culture supernatants derived from 7 donors were found to secrete IgG or IgM and were sequentially tested for reactivity with H3 (A/Brisbane/10/07), H7 (A/Canada/RV444/04), H1 (A/California/04/09) and HA of influenza B (B/Malaysia/2506/04). Through this screen, 237 (22.55%) expanded memory B cells were found to secrete Igs that bound to H3 (Table 3). This in vitro expansion step resulted in a 37-fold increase in H3-reactive B cell recovery compared to 0.61% recovery by sorting plus RT-PCR only (data not shown). The average percentage of cross-reactive clones within the group 2 strains H3/H7 was 18.14%. Remarkably, 13.08% and 8.44% of the H3 binding clones showed heterosubtypic binding to group 1 H1 strains and H7/H1 strains, respectively. Only 3.38% H3-reactive (H3+) clones were found to also bind influenza B. Next, the supernatants of memory B cell clones that showed heterosubtypic binding were tested for microneutralization against H3N2 (A/Brisbane/10/07). One bnAb, 3I14, derived from donor 3 that showed H3/H7/H1 cross-reactivity and neutralization was further characterized.

TABLE 3

Expanded memory B cells (mB) in 7 healthy donors

| Donor # | H3+ population of mB (CD19+/CD27+) | Clonable H3+ mB | Clonable H3+ mB cross to H7+ | Clonable H3+ mB cross to H1+ | Clonable H3+ mB cross to H1+/H7+ | Clonable H3+ mB cross to B+ |
|---|---|---|---|---|---|---|
| 1 | 0.94% | 29 | 0 | 1 | 0 | 1 |
| 2 | 0.30% | 32 | 6 | 1 | 0 | 0 |
| 3 | 0.32% | 29 | 8 | 10 | 6 | 0 |
| 4 | 0.19% | 28 | 4 | 2 | 1 | 0 |
| 5 | 0.95% | 31 | 2 | 0 | 0 | 2 |
| 6 | 0.51% | 66 | 20 | 14 | 11 | 5 |
| 7 | 1.08% | 22 | 3 | 3 | 2 | 0 |
| Total | — | 237 | 43 | 31 | 20 | 8 |
| Average Percentage (%) | 0.61 | 22.55* | 18.14** | 13.08** | 8.44** | 3.38** |

*Percent clonable mBs are from 1051 Ig positive cultures.
**Percent clonable mBs are from 237 H3 positive cultures.

3I14 is a Highly Mutated IGHV3-30-Encoded Antibody

Figure 20:
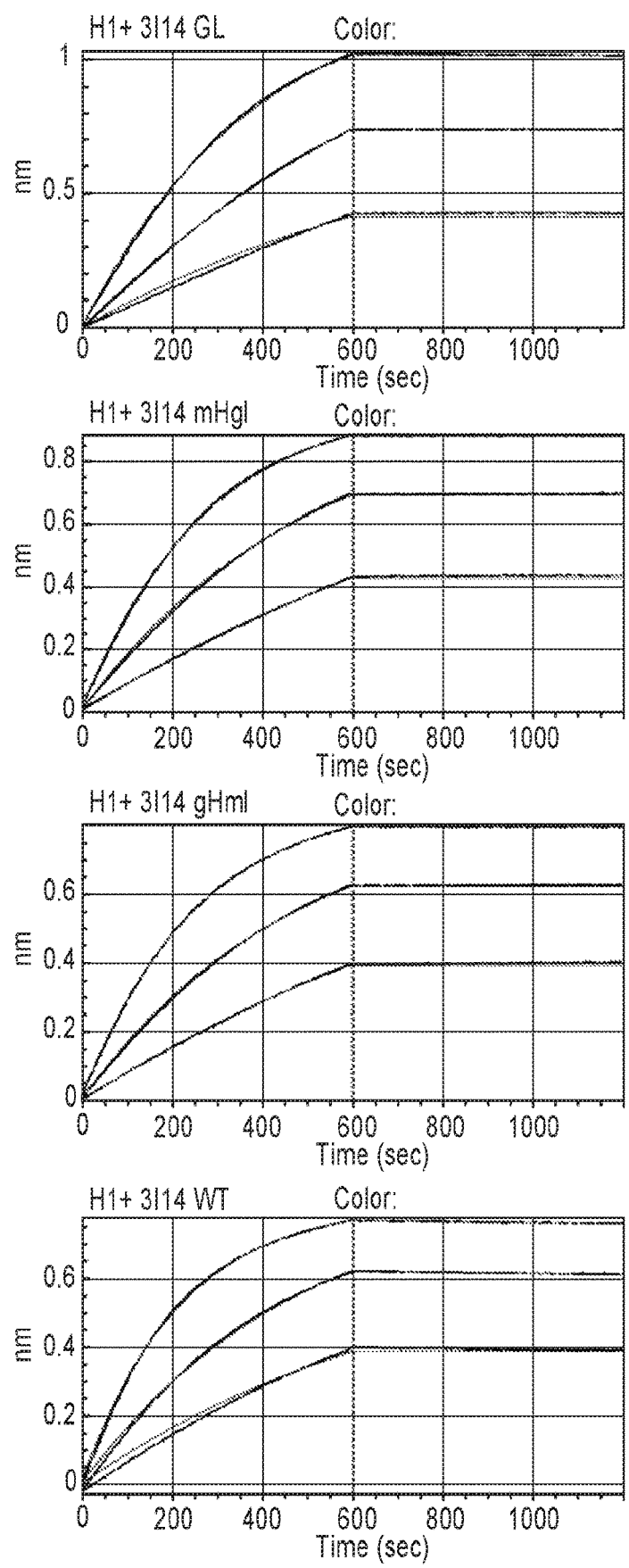
FIG. 20 is a series of graphs that depict binding of the 3I14 IgG1 variants to recombinant H1, H3 and H5. Blue curves are the experimental trace obtained from biolayer interferometry experiments, and red curves are the best global fits to the data used to calculate the $K_d$s presented in Table 7.
Figure 20:
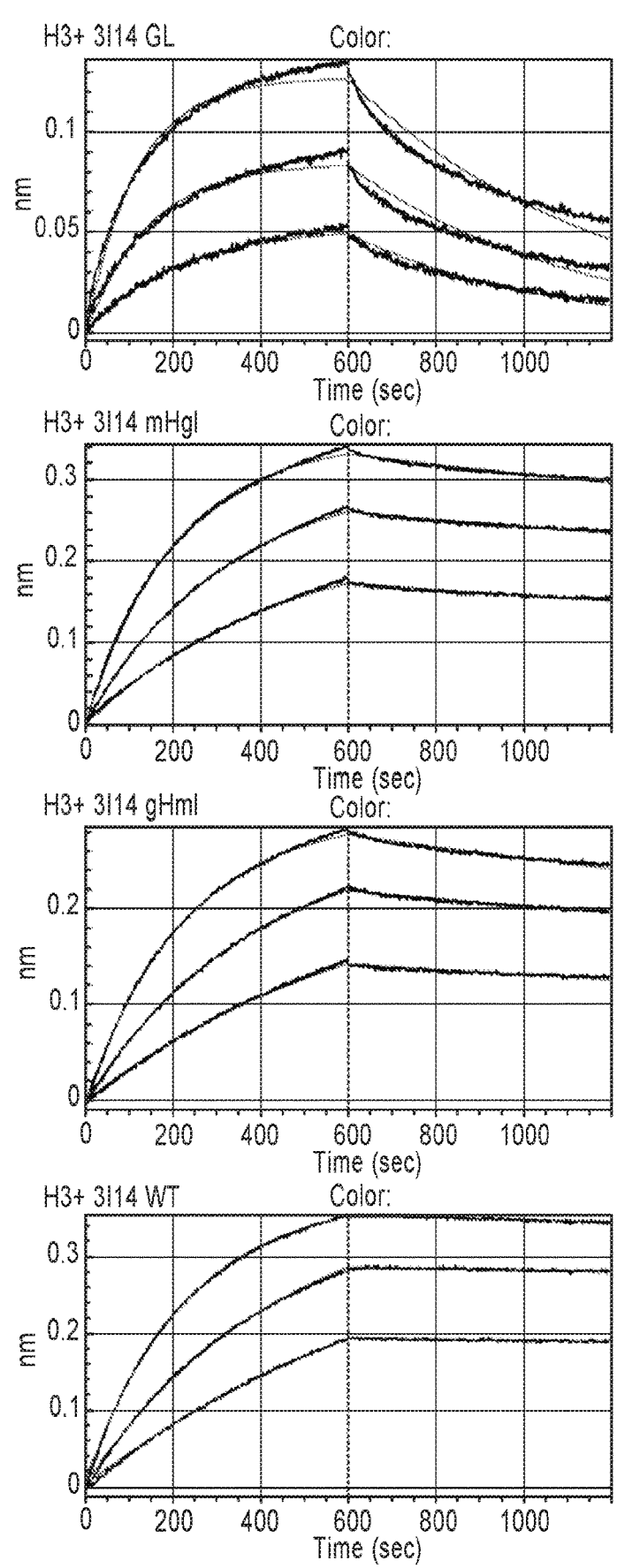
Figure 20:
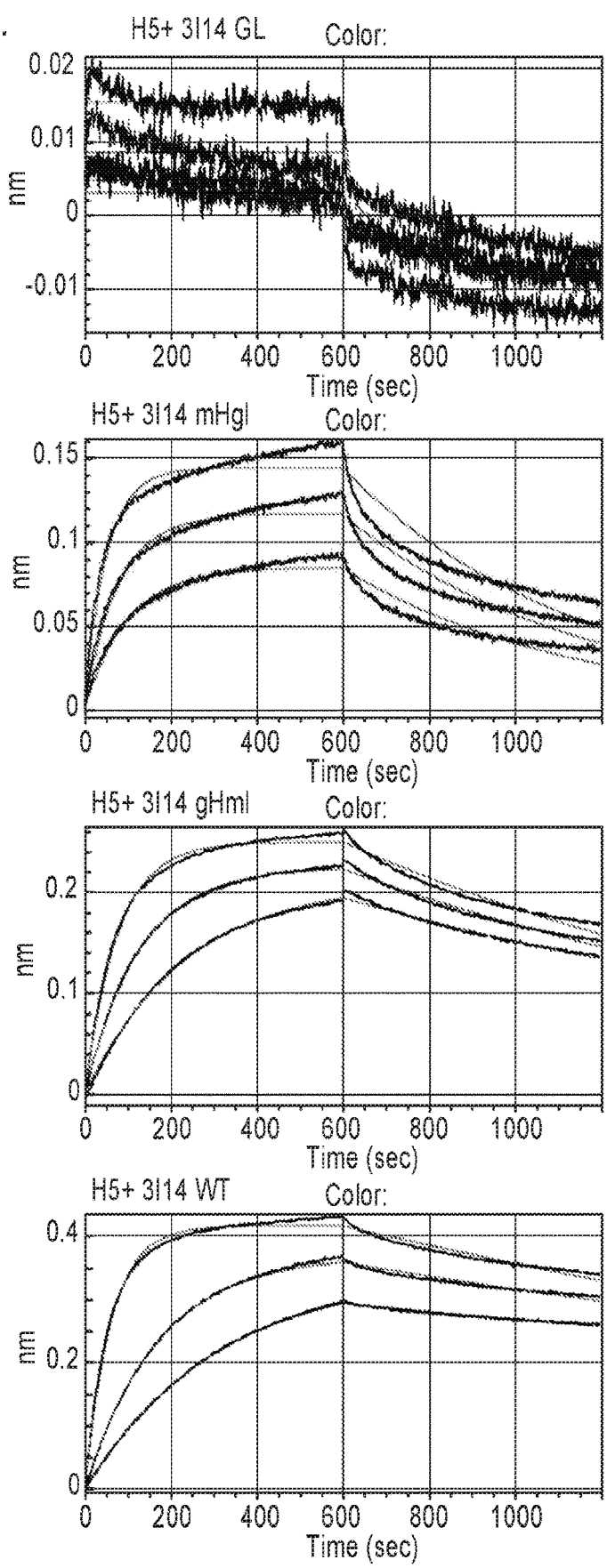

To assess the contribution of somatic mutations on affinity maturation, we produced the 3I14 VH and VL germline versions (3I14-GL), and chimeric antibodies formed by mature (m) 3I14 heavy chain paired with germline (g) light chain (3I14-mHgL) and vice versa (3I14-gHmL) (FIG. 11). The 3I14 variant antibodies were expressed as human IgG1 and their binding affinity against H1, H5 and H3 was evaluated (Table 4 and FIG. 20). Remarkably, 3I14-GL variant still bound H3 and H1 in the nM and sub-nM range while showing a >15-fold decrease in binding affinity to H3 and a 4.7-fold increase in binding affinity to H1, respectively (Table 4). These changes in 3I14-GL binding affinity to H3 and H1 were predominantly caused by an increase and decrease in $K_{off}$ by 13.9- or 7.5-fold, respectively. Interesting, 3I14-GL did not bind H5 under these assay conditions.

TABLE 4

The binding affinity of 3I14 germline variants.

| 3I14 Variants | H5-VN04 | | | H3-PE09 | | | H1-CA09 | | |
|---|---|---|---|---|---|---|---|---|---|
| | $K_d$ (nM) | $K_{on}$ (M$^{-1}$s$^{-1}$) | $K_{off}$ (s$^{-1}$) | $K_d$ (nM) | $K_{on}$ (M$^{-1}$s$^{-1}$) | $K_{off}$ (s$^{-1}$) | $K_d$ (nM) | $K_{on}$ (M$^{-1}$s$^{-1}$) | $K_{off}$ (s$^{-1}$) |
| GL | n* | n* | n* | 4.02 (−Δ15.3) | 1.39E+05 | 5.56E−04 (−Δ13.9) | 0.0597 (Δ4.7) | 1.09E+05 | 6.50E−06 (Δ7.5) |
| mHgL | 7.71 (−Δ7.5) | 2.58E+05 | 1.99E−03 (−Δ5.2) | 0.658 (−Δ2.5) | 1.92E+05 | 1.26E−04 (−Δ3.2) | <0.001** | 1.38E+05 | <1.0E−07** |
| gHmL | 1.95 (−Δ1.9) | 4.34E+05 | 8.44E−04 (−Δ2.2) | 0.733 (−Δ2.7) | 1.71E+05 | 1.25E−04 (−Δ3.1) | <0.001** | 1.55E+05 | <1.0E−07** |
| 3I14 WT | 1.02 | 3.75E+05 | 3.83E−04 | 0.263 | 1.52E+05 | 3.99E−05 | 0.279 | 1.74E+05 | 4.87E−05 |

(Δ) indicates the fold-increase or (−Δ) fold-decrease compared to WT.
*n indicates no binding detected.
**indicates no detectable dissociation.

Comparing the two chimeric forms to wild type (WT) 3I14, the somatic mutations present in both VH and VL of 3I14 appear to make equal contributions to H3 binding ($K_d$: 0.658 nM vs. 0.733 nM). In addition, both the heavy and light chain chimeras resulted in essentially irreversible binding to H1 with $K_{off} < 1.0E-7s^{-1}$. However, in the case of H5, VL mutations contribute more to the affinity increase than VH mutations (7.5-fold vs. 1.9-fold) due to a 5.2-fold and 2.2-fold decrease in $K_{off}$, respectively. From these studies we conclude that 3I14-GL shows higher affinity binding to H1 and moderate affinity to H3 with changes in $K_{off}$ being largely responsible for kinetic differences to compare to 3I14-WT. For H5 binding, the somatic mutations in 3I14 are absolutely required for binding with VL mutations providing a greater contribution to binding than VH changes. All changes in binding affinity to H1, H3 and H5 are mainly the consequence of changes in dissociation rate ($K_{off}$) constants.

The sequences of the variable regions of heavy chain (VH) and light chain (VL) were recovered from the expanded single cell culture using RT-PCR. 3I14 is encoded by the IGHV3-30*18 and IGLV1-44*01 germline genes. The rearranged heavy chain possesses a long complementarity determining region 3 (HCDR3) (23 amino acids) and uses the IGHD3-22*01 DH segment flanked by large N-additions at both VH and IGHJ4*02 junctions (FIGS. 11C and 11D). 3I14 mAb has 15 variable heavy chain and 7 variable light chain somatic mutations excluding the primer-flanking regions, which are observed in both the framework and CDRs.

Example 2: 3I14 Confers Binding and Neutralization to Both Group 1 and Group 2 Influenza Viruses 3I14 bound cell surface-expressed HAs across serotypes of both group 2 (H3, H4, H7, H14 and H15) and group 1 (H1, H2, H5, H6, H8, H9, H11, H12 and H16) influenza A viruses by flow cytometry (FIG. 2). 3I14 also bound purified HA proteins of different subtypes that belong to group 2 (H3, H4, H7 and H14) and group 1 (H1, H5 and H9) with dissociation constants (Kd) ranging from 0.01 nM to 10 nM (FIG. 3 and FIG. 15C). 3I14 bound to all tested group 2 HAs (H3, H4, H7 and H14) with high affinity (mean Kd<0.1 nM). In addition, 3I14 bound to group 1 H1 subtypes (H1-CA09, H1-SI06 and H1-PR8) with high affinity, whereas its affinity for other group 1 subtypes (H5-VN04, H5-IN05 and H9-HK99) was lower (mean Kd=1.02, 1.05 and 5.23 nM, respectively).

Figure 4A:
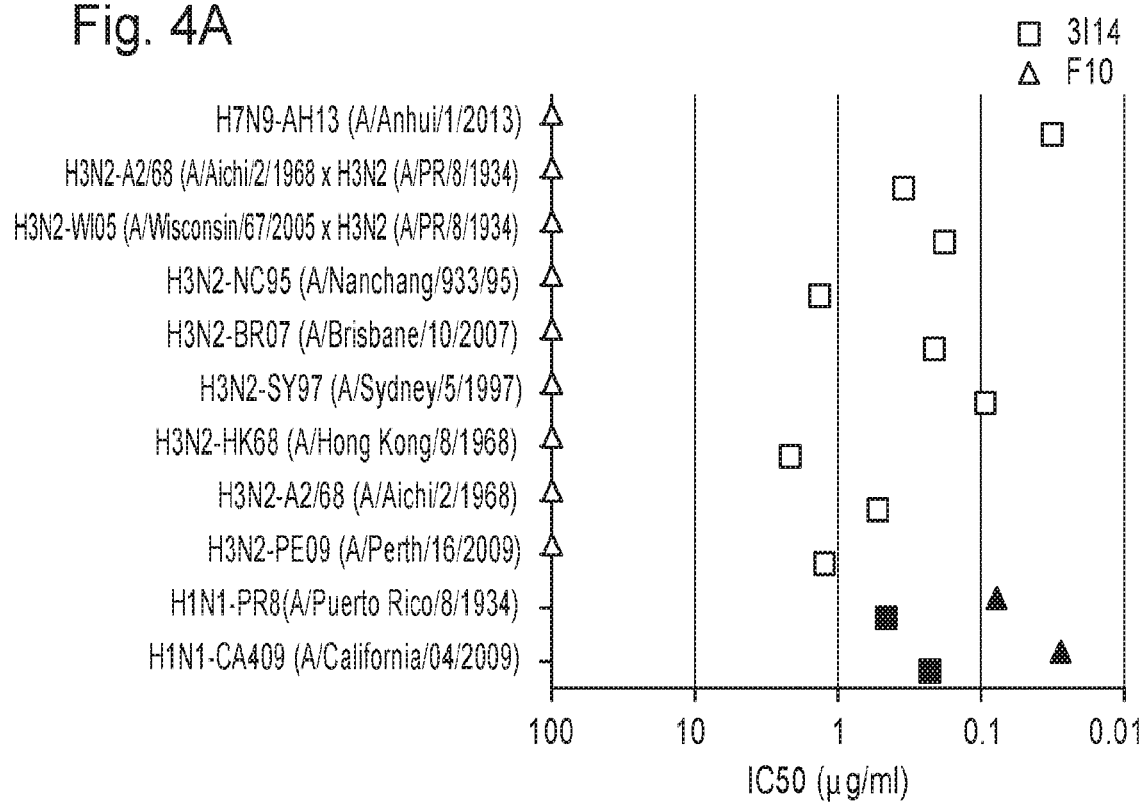
FIG. 4 is a series of graphs that depicts 3I14 IgG1 neutralization (A) ($IC_{50}$ values) or 3I14 scFvFc Ab neutralization ($IC_{50}$ values) of infectious viruses of group 1 (red) or group 2 (blue) subtypes. 3I14 was represented by squares; anti-group 1 mAb F10 was represented by triangles. Graphs used for IC50 values were determined by averaging neutralization titer of 2-3 independent experiments.
Figure 4B:
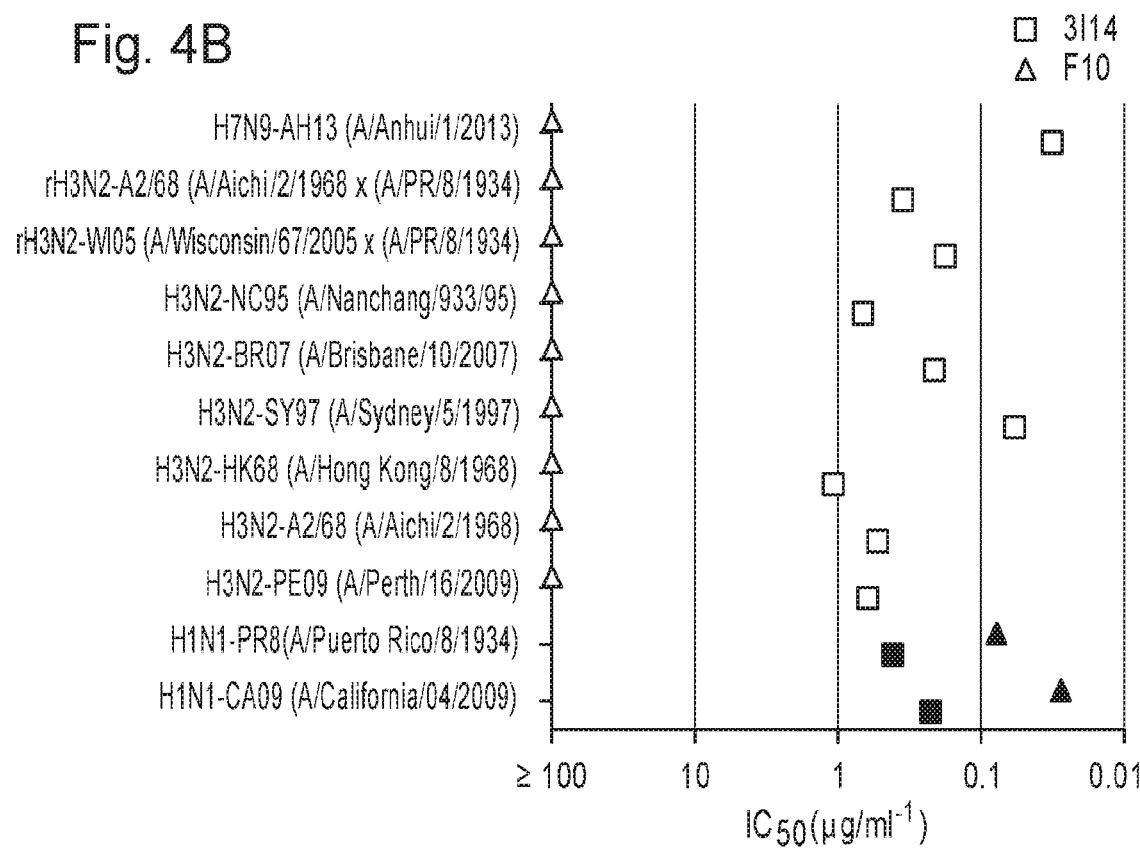
Figure 17:
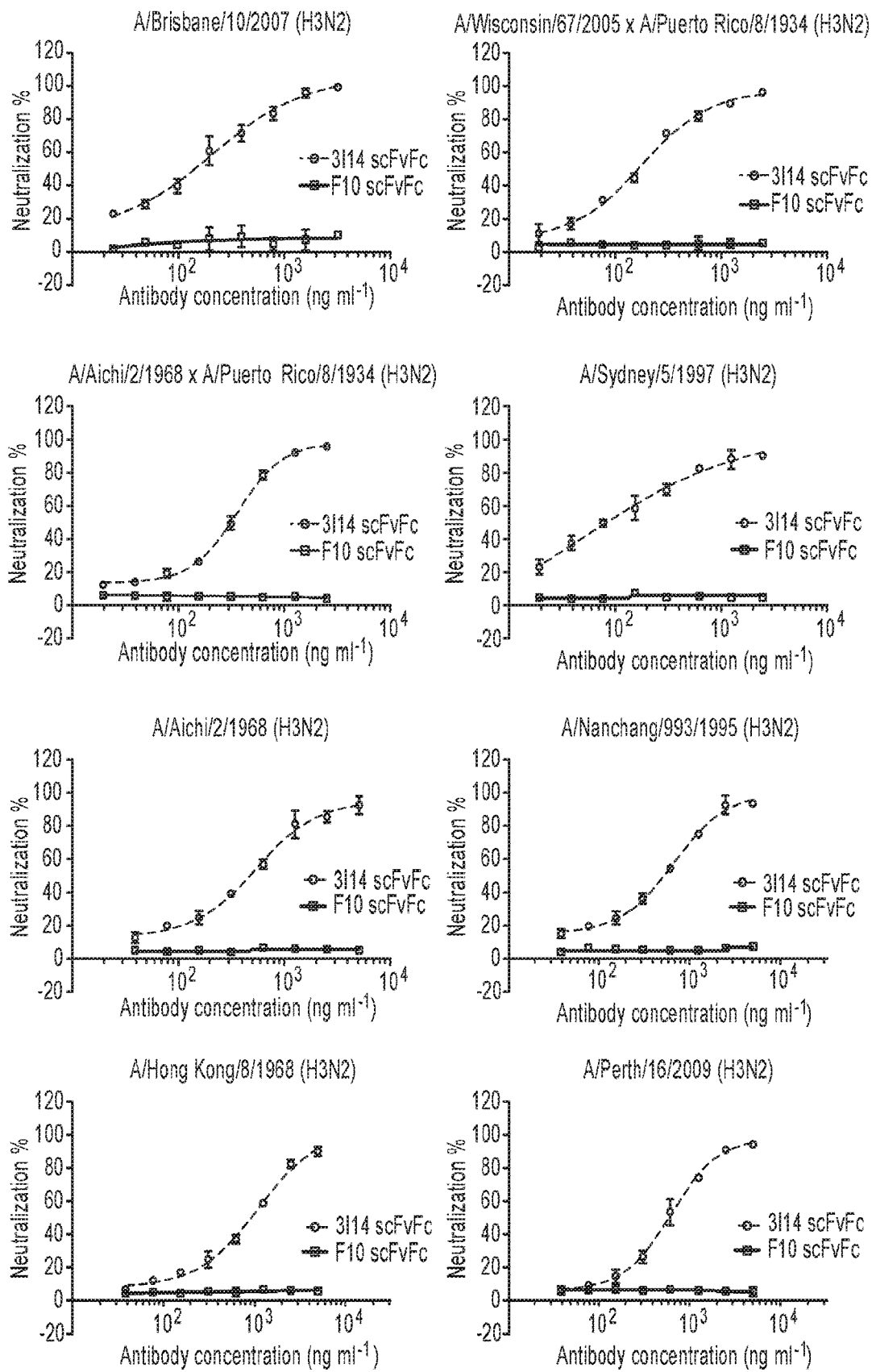
FIG. 17 is a series of graphs that depict 3I14 scFvFc Ab neutralized influenza viruse infection and HA-pseudotyped luciferase reporter viruses. MAb 3I14 (black) and Antigroup 1 mAb F10 (red) neutralized different strains of infectious viruses and pseudotyped viruses. The data represent average neutralization titers from 2-3 independent experiments.
Figure 17:
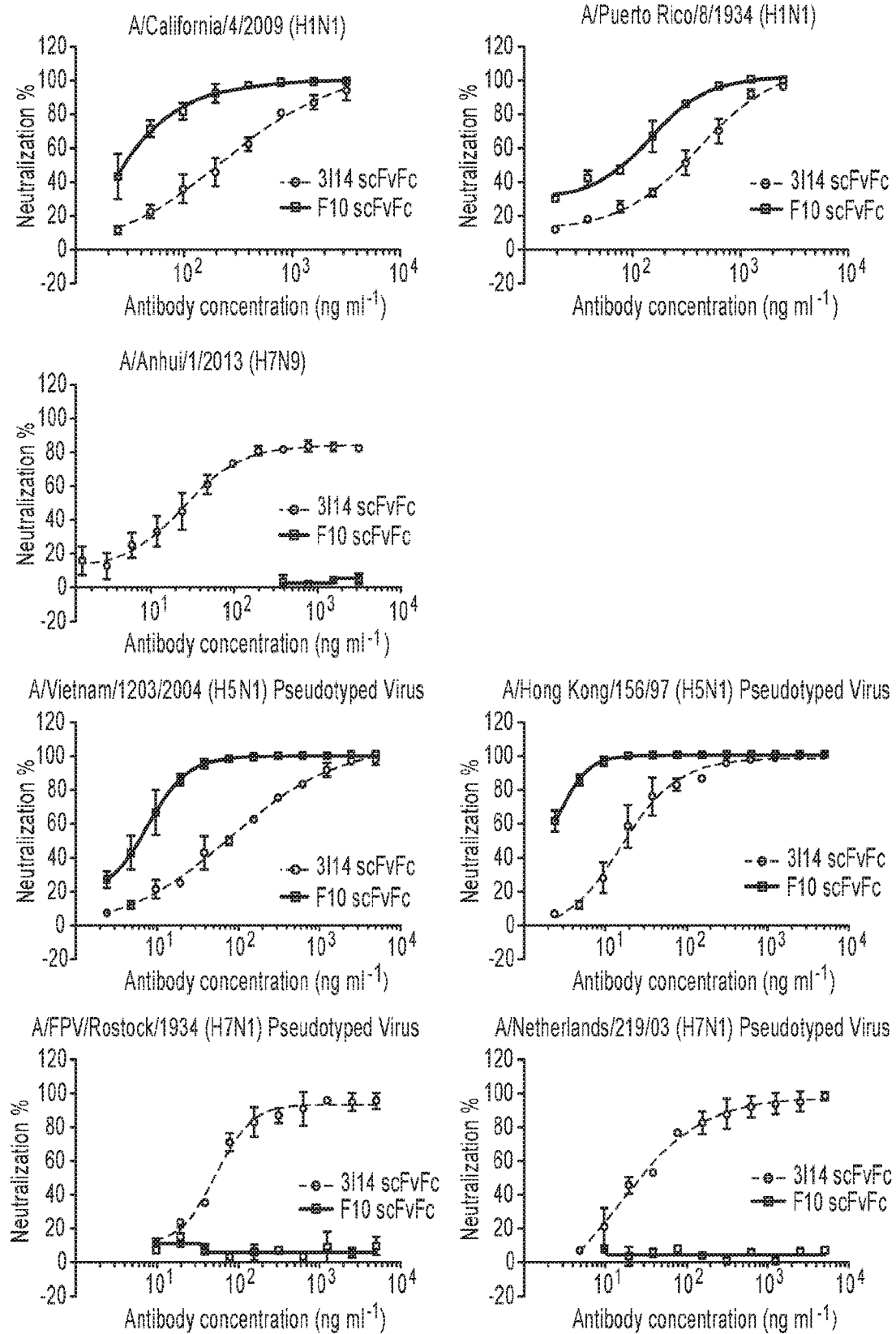

3I14 potently neutralized numerous group 2 (H3 and H7) viruses including two reassortant viral strains (A/Wisconsin/67/05 (HA, NA)×A/Puerto Rico/8/34 and A/Aichi/2/68 (HA, NA)×A/Puerto Rico/8/34) and the novel H7N9-AH13 stain with half maximal inhibitory concentration (IC50) values ranging from 0.032 to 1.074 µg ml-1 (FIG. 4 and FIG. 17). It also neutralized pseudoviruses H7N1-FPN and H7N1-NL219 stains with IC50 values ranging from 0.007 to 0.027 µg ml-1 (FIG. 5B and FIG. 17). In addition, 3I14 neutralized group 1 H1 stains (H1-CA09 and H1-PR8) with IC50 values of 0.225 and 0.413 µg ml-1 (FIG. 5B and FIG. 10) and pseudoviruses H5-VN04 and H5-HK97 with IC50 values of 0.040 and 0.008 µg ml-1, respectively (FIG. 5B and FIG. 17).

Example 3: 3I14 IgG1 Binding (KD Values)

Kinetic analyses of bnAbs binding to recombinant HAs trimer were performed on bio-layer interferometry using an Octet® RED96 instrument (ForteBio, Inc.) at 25° C. The bnAbs IgG1 at 5 nM were captured onto anti-human IgG Fc biosensors in Pierce Protein-free blocking buffer (PBS with Tween-20) for 180 sec. Recombinant full length HAs were load at concentrations ranging from to 6.25 to 100 nM. All experiments contained an additional anti-human IgG Fc antibody biosensor that test for potential nonspecific interactions between HAs and anti-human IgG Fc. For the measurement of kon, association of 3I14 IgG1 was measured for 600 sec by exposing the sensors to up to 20 concentrations of HAs. For the measurement of koff, dissociation of 3I14 IgG1 was measured for 900 sec. The affinity constants (Kd) were calculated using ForteBio Data Analysis 7.0 software.

3I14 bound purified HA protein of different subtypes belonging to Group 1 (H1 and H5) and Group 2 (H3, H4, H7 and H14) with Kd values ranging from 0.01 nM and 10 nM (FIG. 3). 3I14 bound most of Group 2 HAs (H3, H4, H7 and H14) with high affinity (mean Kd<0.1 nM). In contrast, 3I14 bound to H1 subtypes (H1-CA409, H1-SI06 and H1-PR8) with high affinity, whereas its affinity for other Group 1 subtypes (H5-VN04 and H5-IN05) was considerably lower (mean Kd>1 n M).

Recombinant full length HA proteins (rHAs) of H1 subtypes A/California/04/09 (H1-CA409), A/Solomon Island/3/06 (H1-SI06) and A/Puerto Rico/8/34 (H1-PR8); H3 subtypes A/Perth/16/09 (H3-PE09), A/Uruguay/716/07 (H3-UY07), A/Wisconsin/67/05 (H3-WI05), A/Brisbane/10/07 (H3-BR07), A/New York/55/04 (H3-NY04), and A/Victoria/341/11 (H3-VIC11); H5 A/Vietnam/1203/04 (H5-VN04), A/Hong Kong/213/03 (H5-HK03) and A/Indonesia/05/05 (H5-ID05); H7 A/Netherlands/219/03 (H7-NL219), A/Canada/RV444/04 (H7-CA444) and A/Anhui/1/13 (H7-AH13) were obtained from the NIH BEIR Repository (NIAID, NIH). Recombinant full length H3 A/Wisconsin/12/2010 (H3-WI10) was obtained through Influenza Reagent Resources (IRR, Manassas, USA). Recombinant full length HAs of subtypes H3 A/Aichi/2/68 (H3-A268), H4 A/mallard/Netherlands/2/05 (H4-NL05) and H14 A/mallard/Astrakhan/263/82 (H14-A582) were kindly gifted from Dr. R. C. Liddington (Burnham Institute for Medical Research, CA, USA).

Example 4. 3I14 IgG1 Neutralization (IC50 Values)

Figure 5A:
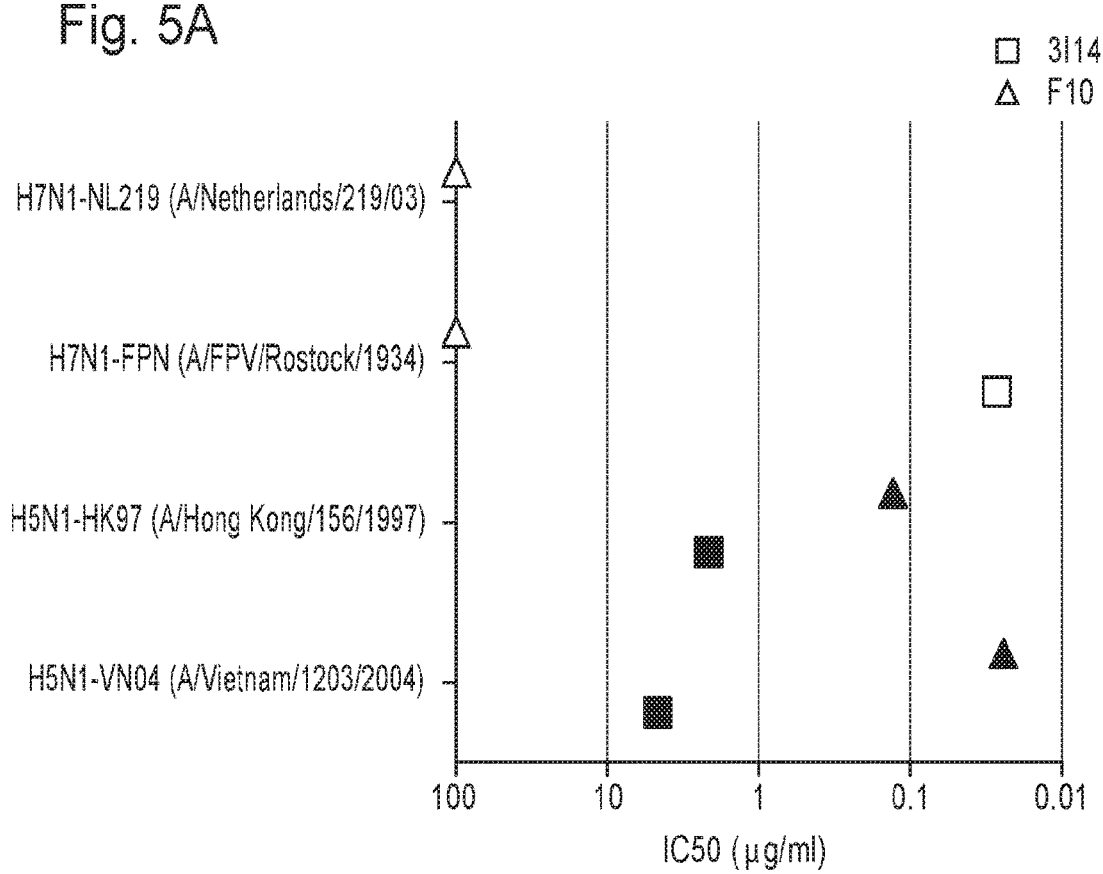
FIG. 5 is a graph that depicts 3I14 IgG1 neutralization (A) ($IC_{50}$ values) or 3I14 scFvFc neutralization (B) ($IC_{50}$ values) of pseudoviruses representative of group 1 or group 2 subtypes. These data represent average neutralization titers of 2-3 independent experiments.
Figure 5B:
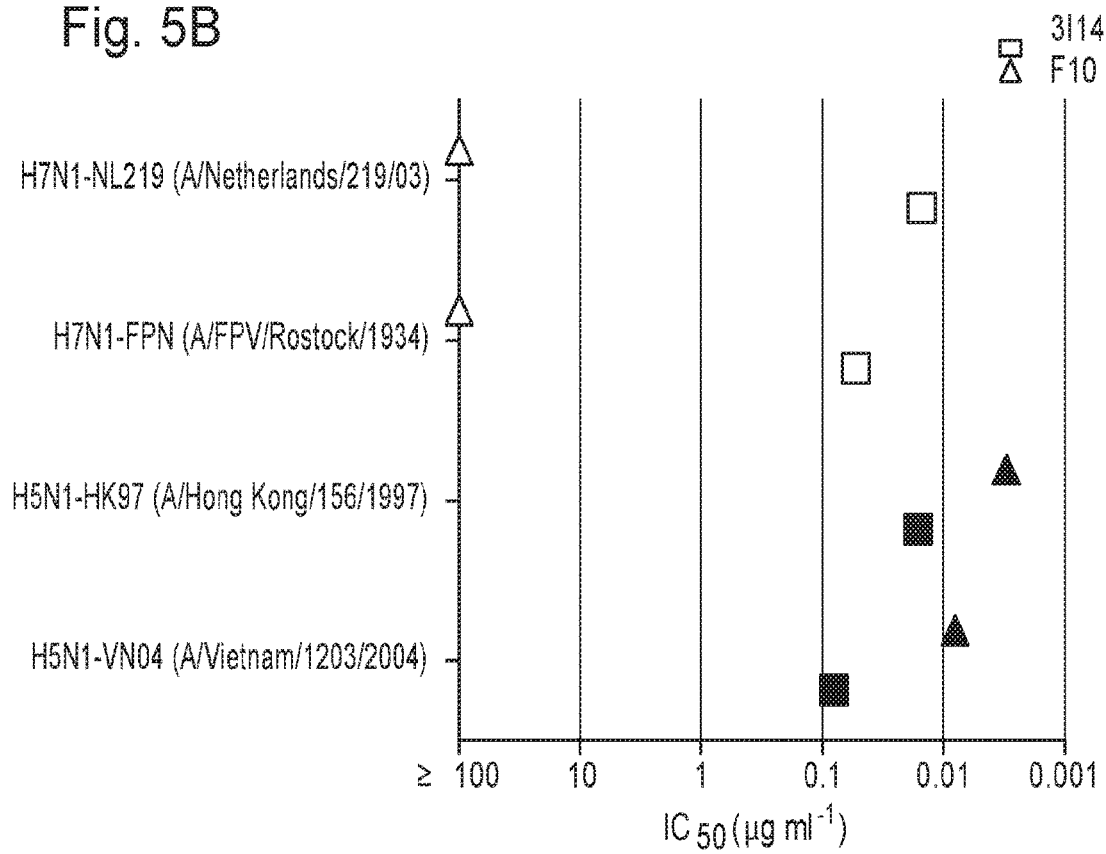

The IC50 graphs depict the average neutralization titer of 2-3 independent experiments. 3I14 was represented as a square, while anti-group 1 mAb F10 IgG1 (represent as triangle) was used as controls (FIGS. 4 and 5).

MDCK cells ($1.5 \times 10^4$ cells per well) were seeded into 96-well tissue culture plates and washed twice with PBS, followed by incubation in DMEM supplemented with 2 µg/mL trypsin and 0.5% BSA. 100 TCID50 (median tissue culture infectious doses) of virus were mixed in equal volume with two-fold serial dilutions of Ab or antibody containing supernatant in 96-well plates, and incubated for 1 h at 37° C. After the incubation, the Ab-virus mixture was transferred to confluent MDCK monolayers in duplicate, followed by incubation at 37° C. for 21 h. Cells were washed with PBS, fixed in acetone, and viral antigen detected by indirect ELISA with a mAb against influenza A Virus Nucleoprotein (NP) (clone A3, BEI). The half maximal inhibitory concentration (IC50) is the Ab concentration at which the effectiveness is reduced by 50% compared to wells containing virus control after subtraction of backgrounds.

3I14 neutralized Group 1 (H1) and Group 2 (H3 and H7) viruses in vitro. 3I14 potently neutralized different H1, H3 and H7 viruses with IC50 values ranging from 0.032 to 1.336 µg/ml (FIGS. 4 and 5).

Example 5. 3I14 IgG1 Neutralization (IC50 Values) of Pseudoviruses Representative of Group 1 and Group 2 Subtypes The IC50 graphs depict the average neutralization titer of 2-3 independent experiments. 3I14 was represent as square, while anti-group 1 mAb F10 IgG1 (represented as triangles) was used as controls.

3I14 potently neutralized H7N1-FPN and H7N1-NL219, both of which are group 2 pseudoviruses, with IC50 values ranging from 0.032 to 1.336 µg/ml. It also neutralized group 1 pseudoviruses H5-VN04 and H5-HK97 with IC50 values ranging from 2.137 and 4.601 µg/ml, respectively (FIG. 5).

Figure 6A:
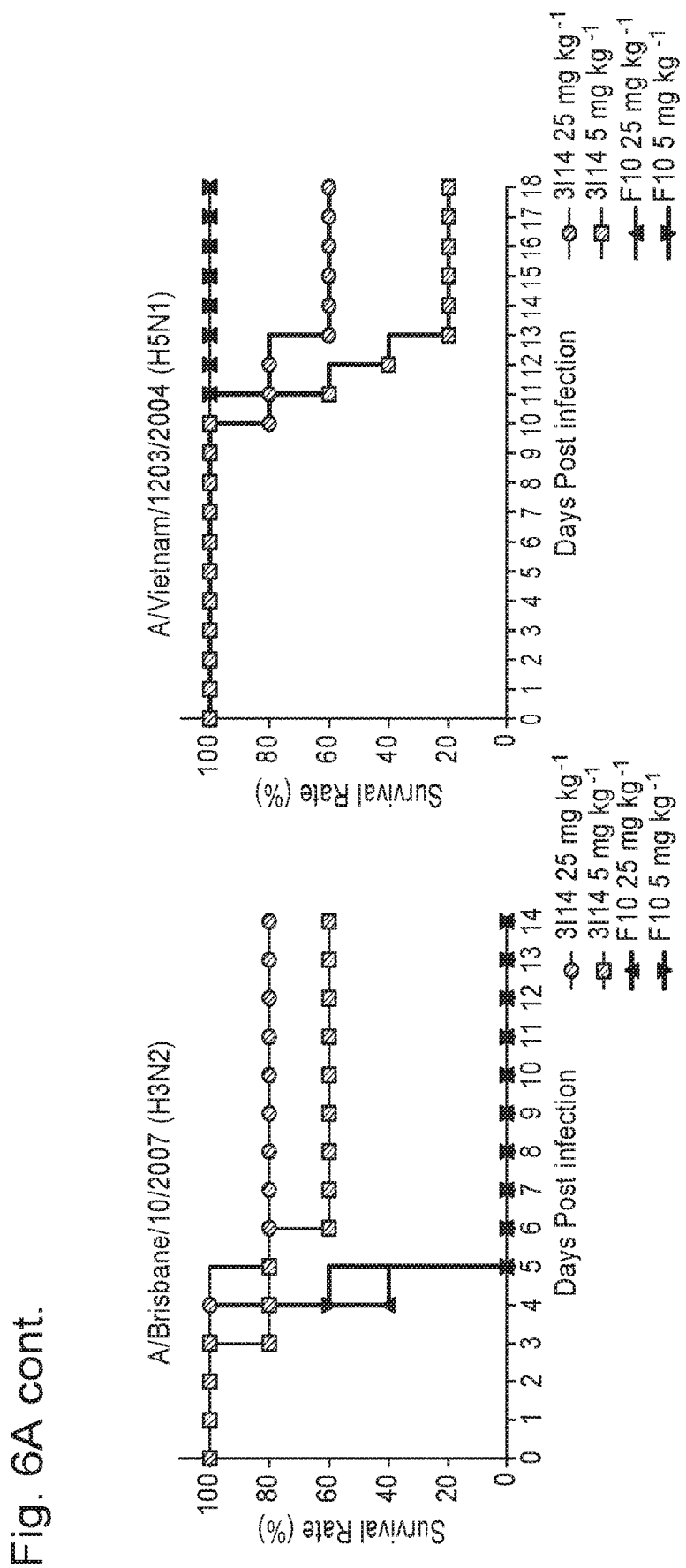
FIG. 6 is a series of graphs that depicts the survival rate (A) of mice exposed to influenza virus and administered purified IgGs intraperioneally at one of the following concentrations, 5, 20, or 25 mg.
FIG. 6B is a series of graphs that depict changes in body weight composition in mice that were exposed to influenza virus and administered the specified antibody concentrations indicated. For these assays, groups of 5 mice were treated with 20/25 or 5 mg/kg doses of purified IgGs given intraperitoneally 24 h before lethal challenge by i.n. inoculation with H7N7-NL219, H7N9-AH13, H3N2-BR07 or H5N1-VN04 influenza viruses (~10 LD50). (a) Survival (%) and (b) body weight change (%) of mice that were treated with bnAb 3I14 (red) and group 1 control mAb F10 (black).
Figure 6B:
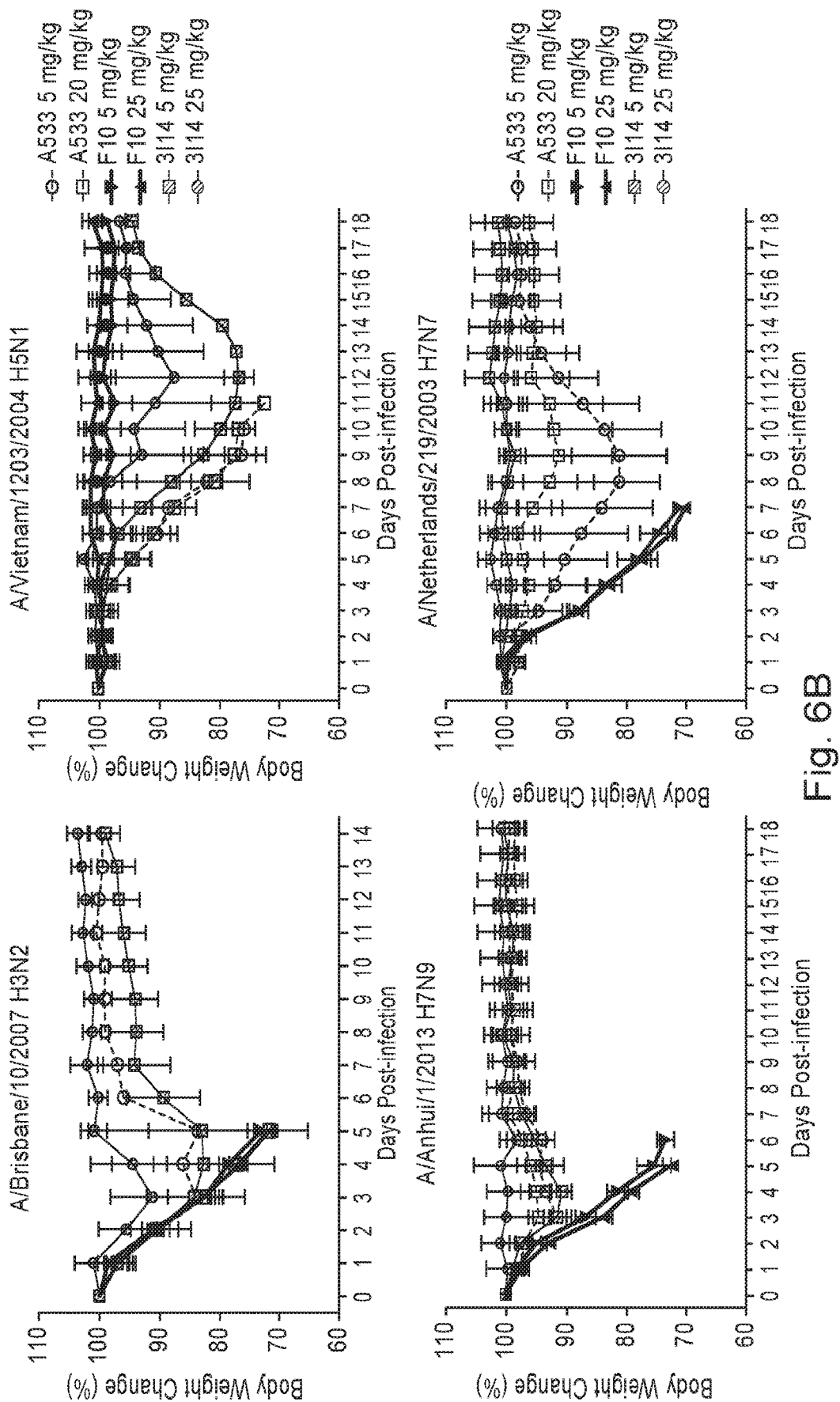
Figure 6B:
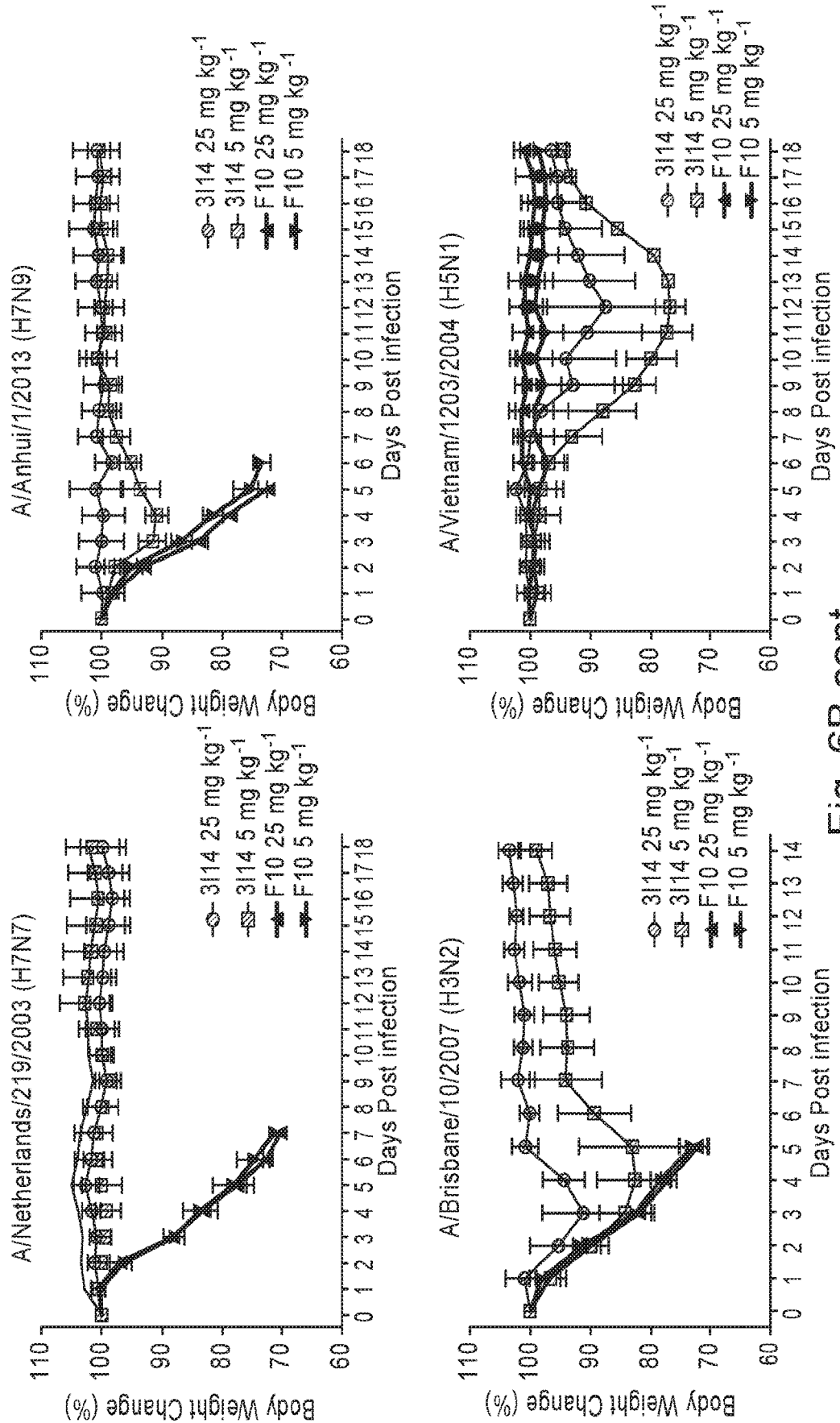

Example 6. Prophylactic Efficacy of 3I14 Against Group 2 and 1 Influenza Viruses in Mice We converted 3I14 into full-length human IgG1 to evaluate protective efficacy against H5N1, H3N2, H7N7 and H7N9 infection in a BALB/c mouse model (FIG. 6). Anti-group 1 Ab, F1012 was using as stain-specific control. Mice were treated with varying doses of 3I14 and F10 IgG1 one day before challenge with a lethal dose of H7N7-NL219, H7N9-AH13, H3N2-BR07-ma and H5N1-VN04 viruses. Prophylaxis using 5 mg kg-1 3I14 IgG1 fully protected mice from death after H7N7-NL219 or H7N9-AH13 challenge with minimal body weight loss at 14 to 18 days (FIG. 6A). At the dose of 25 mg kg-1 3I14 IgG1 showed 80% protection against H3N2-BR07 and 60% protection against H5N1-VN04. All surviving mice showed the reversal of weight loss by the end of the observation period (FIG. 6b). Groups of 5 mice were treated intraperitoneally 25 or 5 mg/kg of purified IgGs with 24 h before lethal challenged by i.n. inoculation with H3N2 BR07, H5N1 VN04, H7N9 AU13 or H7N7 NL219 influenza viruses. (A) survival rate (%) of mice and (B) body weight change (%) that treated with bnAb 3I14 (RED), group 1 control mAb F10 (BLACK) and group 2 control mAb A533 (BLUE).

One day prior to the experiment, groups of five female 8-10 week old BALB/c mice were injected with 3I14, F10 and A533-IgG1 at low concentration of 5 mg/kg and high concentration of 20 or 25 mg/kg by intraperitoneal (i.p.) route in 0.5 mL volume, respectively. 6 groups of mice were intranasally infected 10 LD50 of either mouse-adapted A/Vietnam/1203/04 (H5N1), A/Brisbane/10/07 (H3N2), A/Netherlands/219/03 (H7N7) or A/Anhui/1/13 (H7N9). Mice were weighed on the day of virus challenge and then monitored for survival and weighed daily for 14 days or 18 days. Animal studies were conducted per approved Institutional Animal Care and Use Committee protocols.

Mice were treated with varying doses of 3I14, F10 (Group 1 control Ab) and A533 (Group 2 control Ab) IgG1s 1 day before challengwith a lethal dose of H5N1-VN04, H3N2-BR07, H7N7-NL219 and H7N9-AU13 viruses. Prophylaxis using ≥5 mg/kg 3I14 IgG1 fully protected mice from death after H7N7-NL219 or H7N9-AU13 challenge with minimal body weight loss in the observation period. These results indicate that 3I14 IgG1 effectively protected (60-80%) mice when challenged with a lethal dose of H3N2-BR07, and partially protected (20-60%) mice with a lethal dose of H5N1-VN04 (FIG. 6A). Although a dose of 5 mg/kg 3I14 IgG1 was only partially protective to prevent morbidity caused by H3N2 and H5N1, all surviving mice showed a reversal of weight loss at the end of the observation period at doses of 5 or 25 mg/kg (FIG. 6B).

Figure 7:
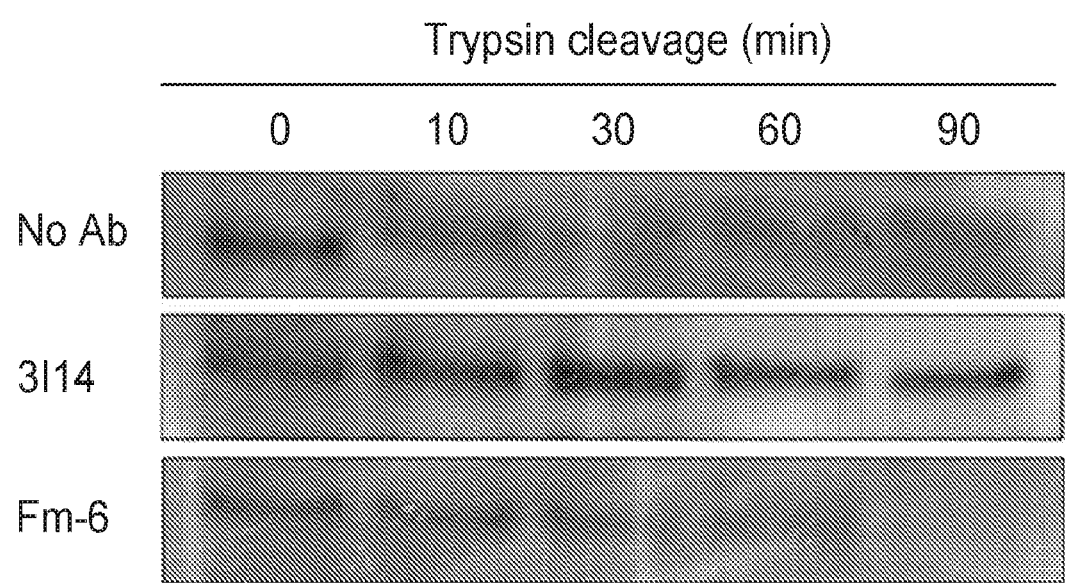
FIG. 7 is a gel that shows the results from a Trypsin Cleavage Inhibition Assay in which no antibody, 3I14 or Fm-6 (an IgG1 control) was used. For this assay, 0.4 µg recombinant H3-histidine (H3-BR07) was incubated in the presence of 2.5 µg 3I14 or Fm-6 IgG1, or in the absence of antibody in Tris-HCl buffer at pH 8.0 containing 100 µg/mL Trypsin-ultra (New England Biolabs, USA) at 37° C. Trypsin digestion was inhibited at several time-points by addition of 1% BSA. Samples were run on 12% reduced SDS-PAGE and blotted using a HisProbe-HRP Abs.
Figure 8:
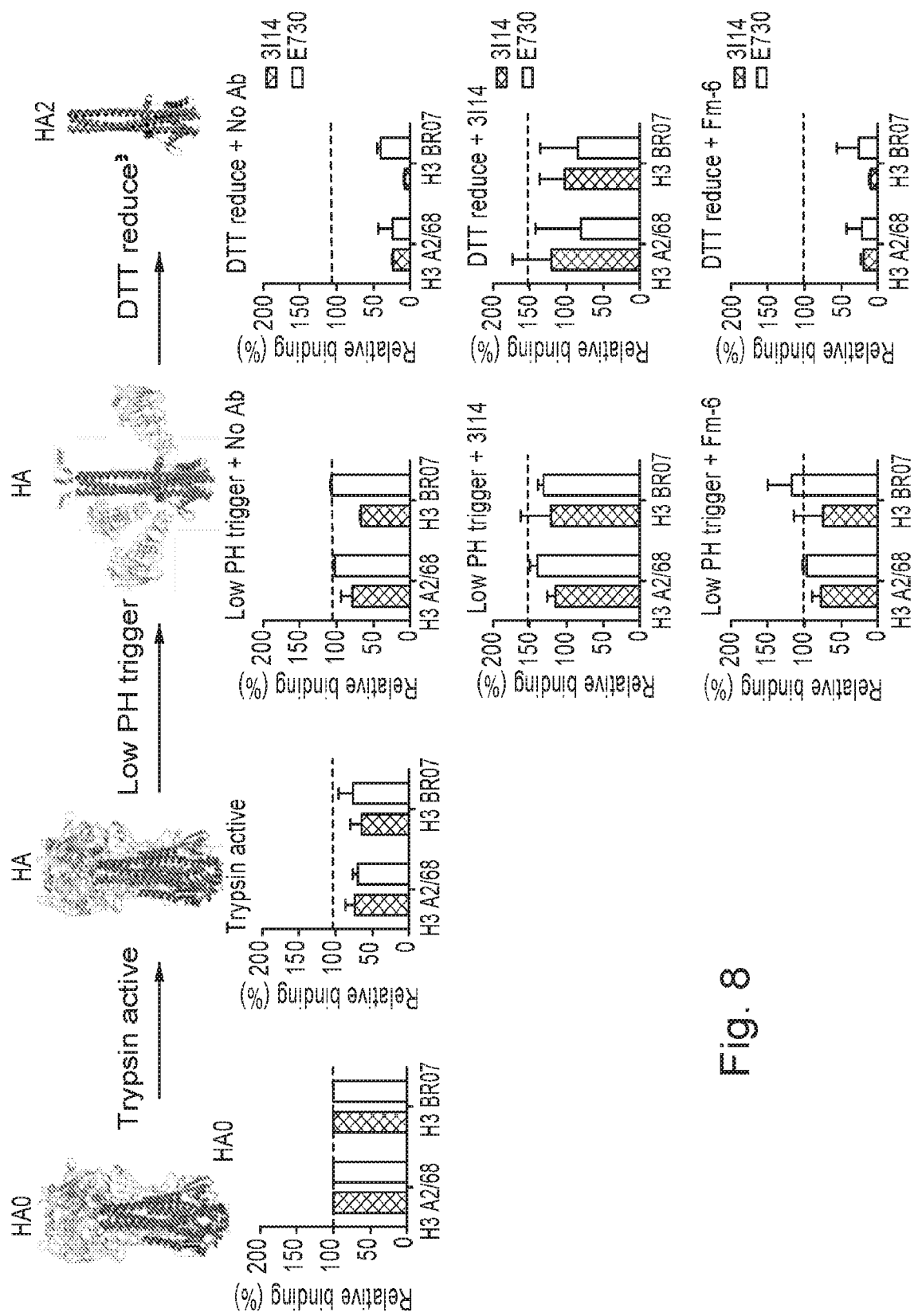
FIG. 8 is a series of schematics and graphs that depict 3I14 IgG1 prevented low-pH triggered conformational rearrangements on surface-expressed H3-A268 and H3-BR07. The conformation rearrangements of surface-expressed H3 were detected by FACS staining of 3I14 (solid bars) and the head binding control mAb E730 (open bars). Binding is expressed as the percentage of binding to untreated HA (HA0). For this antibody inhibition assay, H3 was pretreated without mAb, with 3I14, or with control Ab, Fm-6 IgG1 before exposure of the cleaved HAs to pH 4.9. Data represent mean+SD of three independent experiments.

Example 7: 3I14 Blocks Trypsin-Mediated HA Maturation and pH-Dependent Conformational Changes Stem-directed bnAbs are known to interfere with pH-dependent conformational changes and membrane fusion of HA[12, 14, 16]. Cleavage of the precursor HA0 primes HA for subsequent activation of membrane fusion in the acidic endosome environment. Immature HA0 is normally processed by surface protease on respiratory epithelial cells to HA1 and HA2[28, 29] which is mimicked experimentally by treatment of HA0 with trypsin[30]. Since 3I14 targets the stem domain of HA comprising the HA0 cleavage site and the HA2 N-terminal fusion peptide, we tested whether 3I14 could also block trypsin cleavage activation of HA0 or interfere with HA-mediated virus-host membrane fusion. FIG. 7 shows that 3I14 IgG1 but not control anti-SARS IgG1 (Fm-6) prevented cleavage of immature HA0. We also analyzed 3I14's prevention of low pH-triggered conformational rearrangements using the surface-expressed H3-A2/68 and H3-BR07. FIG. 8 (upper) illustrates that 3I14 binds to both uncleaved HA precursor (HA0) (left) and two mature forms (HA), either after trypsin activation alone (left middle) or when followed by low-pH trigger (right middle). In contrast, it did not bind to dissociated HA2 mediated by DTT reduction (right). When 3I14 is pre-bound to mature HAs before low-pH trigger, the antibody maintained binding after DTT treatment (FIG. 8, 4th panel), indicating that 3I14 inhibits the pH-dependent HA rearrangement (FIG. 8, lower). In addition, pre-binding of 3I14 prevented HA1-HA2 dissociation, because binding of E730 Ab (anti-HA1) was preserved after DTT treatment (FIG. 8, lower). From these data we conclude that 3I14 binding to the HA stem epitope leads to inhibition of HA0 cleavage and pH-dependent conformational changes.

Example 8: 3I14 IgG1 Prevented Low-pH Triggered Conformational Rearrangements on Surface-Expressed H3-A268 and H3-BR07

The conformation rearrangements of surface-expressed H3 were detected by FACS staining of 3I14 (solid bars) and the head binding control mAb E730 (open bars) (FIG. 8). The various conformations are indicated above the corresponding graphs and were as follows: uncleaved precursor (HA0); trypsin activated, cleaved (HA); low pH trigger, cleaved (pH 4.9); and DTT reduced, trimeric HA2 (tHA2). Binding is expressed as the percentage of binding to untreated HA (HA0). For antibodies inhibition assay, H3 was pretreated without mAb, with 3I14, or with control Ab, Fm-6 before exposure of the cleaved HAs to pH 4.9. Data represent mean+SD of three independent experiments.

As shown in FIG. 8, 3I14 bound to both uncleaved HA precursor (HA0) and mature forms (HA) after trypsin activation and low-pH trigger, but didn't bind dissociated HA2 mediated by DTT reduction. While 3I14 pre-bound to mature HAs before low-pH trigger, the antibody remained bound after DTT treatment, indicating that 3I14 inhibits the pH-dependent HA rearrangements and the subsequent membrane fusion. In addition, pre-binding of 3I14 prevented the dissociation of HA' from HA2, because the binding of E730 Ab (anti-HA1) was preserved after DTT treatment.

MDCK cells were transfected with full-length recombinant influenza A pcDNA3.1-H3-A268 and H3-BR07 plasmids. After ~30 hours of transfection, the cells were detached from the plastic support using 0.2% EDTA/PBS. To measure mAb binding to different HA structural forms and conformations, cell samples were split and stained with 3I14 or E730 IgG1 (anti-H3 head) after each processing step. Detached cells subsequently treated with trypsin (TrypLE™ Select Enzyme, Gibco) for 5 min at room temperature, washed with 1% BSA/PBS and incubated for 15 min in citric acid-sodium phosphate buffer pH 4.9, washed, and then incubated for 20 min with 50 mM dithiothreitol (DTT) in PBS at room temperature. Alternatively, the 5 μg 3I14 or Fm-6 IgG1 was added before the low pH step. Samples of subsequent treatments were stained with APC-conjugated anti-human Fc (BioLegend, Inc.). Stained cells were analyzed using a BD FACSAria™ II with FACS Diva software (Becton Dickinson).

Example 9: 3I14 Mediates FC-Dependent Viral Clearance

Anti-stem bnAbs are reported to efficiently mediate FcγR-dependent cytotoxicity of influenza virus-infected cells[31], which is considered to be a major mechanism of mAb-mediated antiviral clearance. To investigate the properties of antibody-dependent cellular cytotoxicity (ADCC) by 3I14 and other anti-stem bnAbs, we performed a surrogate reporter-based ADCC assay in vitro using the engineered Jurkat effector cells stably expressing human FcγIIIa and nuclear factor of activated T-cells (NFAT)-induced luciferase[32] together with HA-expressing 293T cells as targets. Following incubation with H3-expressing 293T target cells, 3I14 induced a significant luciferase response in Jurkat reporter cells in a dose-dependent manner and at a comparable level to other anti-stem bnAbs including FI6v3, CR9114, 39.29 and group 2 mAb CR8020 (FIG. 9). The specificity of this assay was demonstrated by the lack of response from anti-group 1 mAb, F10. 3I14 also specifically induced the luciferase response against H5-expressed 293T cells but at a lower level than FI6v3, CR9114, 39.29 and F10. We observed low reactivity for CR8020 against H5-expressed 293T target cells (FIG. 9). These data support that 3I14 also likely engages an Fc-dependent immune-mediated mechanism for in vivo protection.

Example 10. 3I14 Cross-Competes for Binding to H3 or H5 with Other Anti-Stalk bnAbs, FI6, CR9114, 39.29, F10 and CR8020

5 μg/ml H3-BR07 or H5-VN04 protein immobilized on ELISA plates were incubated with a 2-fold serial dilution of 3I14 $F_{ab}$ ranging from 80 nM to 0.3 nM and mixed with other scFvFc Abs at 5 nM. After coincubation for 1 h, the binding of scFvFc Abs was detected using HRP conjugated anti-human CH2 antibodies. 3I14 Fab cross-competed for binding to H3-BR07 with other anti-stalk Abs, including CR8020, CR9114, F16 and 39.29, but did not compete with E730, an anti-HA1 antibody (FIGS. 10A-D). 3I14 also inhibited the binding of 39.29 and F10 to H5-VN04, but did not inhibit the binding of anti-head antibody, 2A (FIGS. 10E-F). These results suggest that 3I14 targets an epitope in the HA stem region that overlaps with or is very close to the known epitopes of other anti-stalk bnAbs.

Example 11. Structural Based Affinity Maturation In Vitro

Figure 12A:
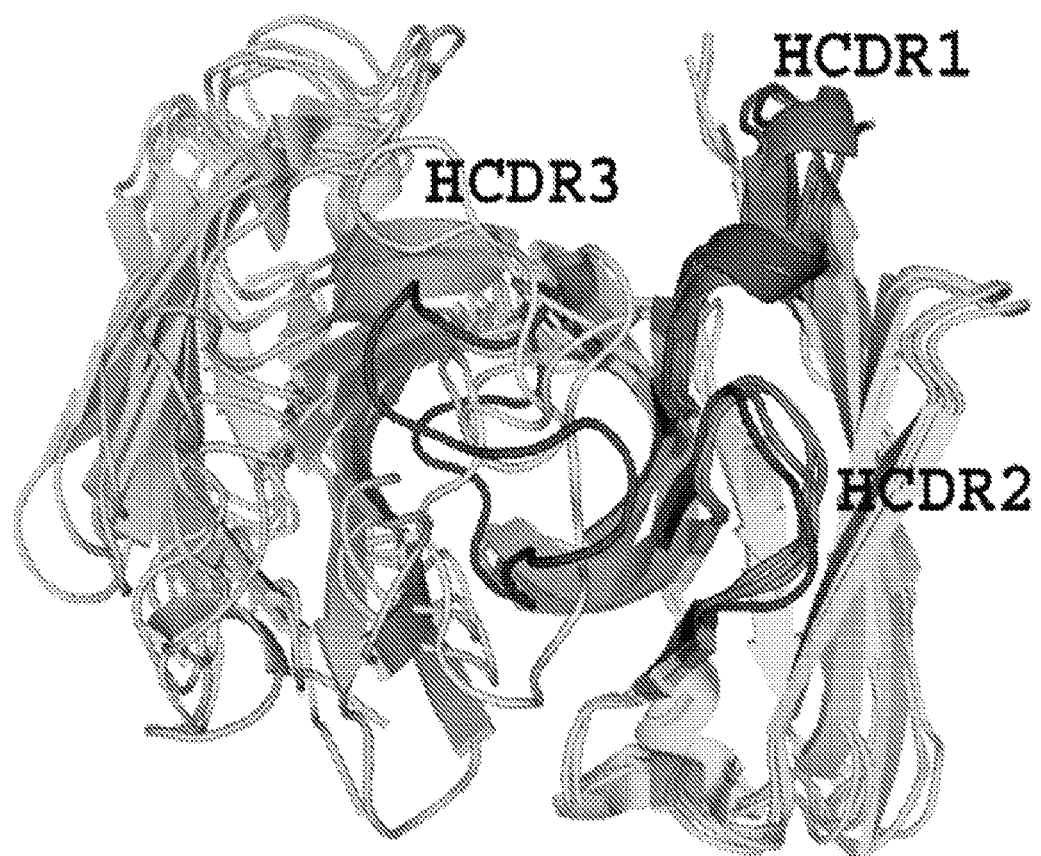
FIGS. 12A and 12B is a series of schematics depicting the superimposition of the 3I14 model with three VH3-30 BnAbs, 39.29 (from 4KVN), FI6 (from 3ZTJ) and Mab3.1 (4PY8). A protein model schematic is depicted that shows the relative positioning of the heavy and light chain as well as the heavy CDRs of the 3I14 antibody. The heavy chain is shown in green and the light chain is in grey. The heavy chain CDRs in FIG. 12 are color coded as follows: 3I14 HCDRs as blue, HCDR1 of other BnAbs are red, HCDR2 are magenta and HCDR3 are cyan.
Figure 12B:
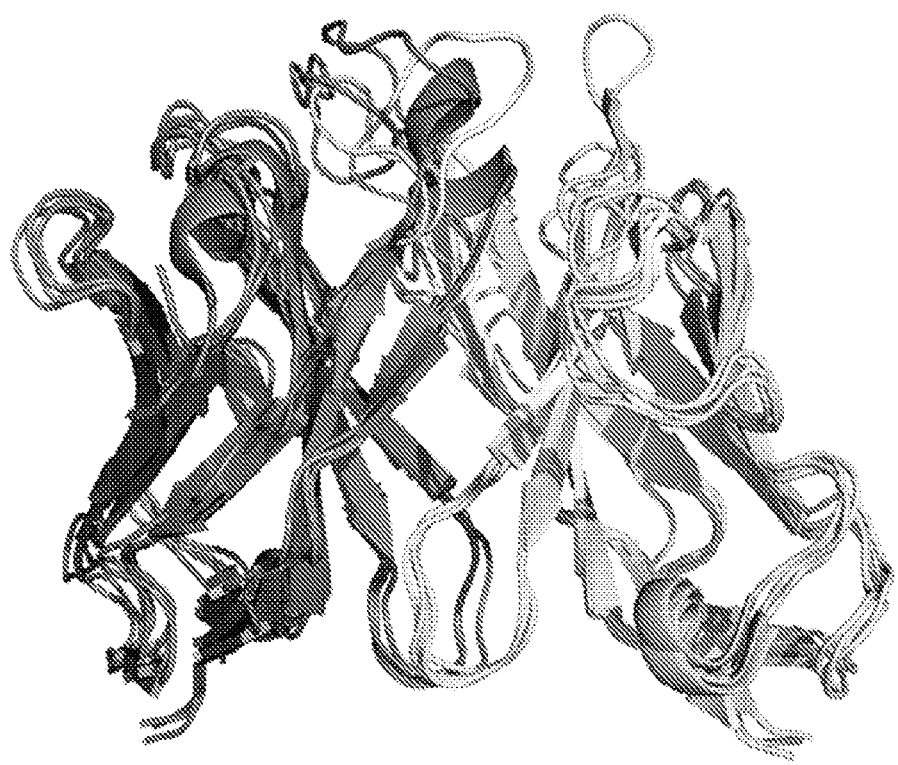

In order to characterize the molecular basis for unequal binding strengths to H3 and H5 and to engineer 3I14 with improved affinity to H5N1 strains, we first used an antibody structure prediction program BioLuminate[33] for in silico simulation of the 3I14 structure. The superimposition of the 3I14 model with other three IGHV3-30 bnAbs, FI6v3, 39.29 and MAb 3.1, is shown in FIG. 12B. It is clear that the major difference among these antibodies is the conformation of HCDR3 with the exception of the longer LCDR1 of FI6v3 that forms a loop structure which makes contact with HA.

Next, the 3I14 model was docked to the H3 trimer structure with RosettaDock server[34]. Since 3I14 competes with FI6v3 and 39.29 for binding to H3 and H5, and MAb 3.1 occupies the same conserved epitope with FI6v3 and 39.29[18], we hypothesized that 3I14 adopts a similar binding scheme to interact with H3/H5 as FI6v3, 39.29 and MAb 3.1. For these three Ab-HA co-crystal structures, HCDR3 plays a major role in forming a hydrophobic core with the fusion peptide and helix A[15, 17, 18]. Rather than making significant interactions with HA, HCDR1 and HCDR2 appear to stabilize the HCDR3 loop to facilitate binding. The hydrophilic light chain CDR residues also interact with HA and surround the hydrophobic core, however the orientation of the light chains are not conserved nor are the residues involved in binding. These observations suggest that the light chains mainly contribute to the binding by orienting the HCDR3 to an optimal position to interact with the epitope.

Figure 13A:
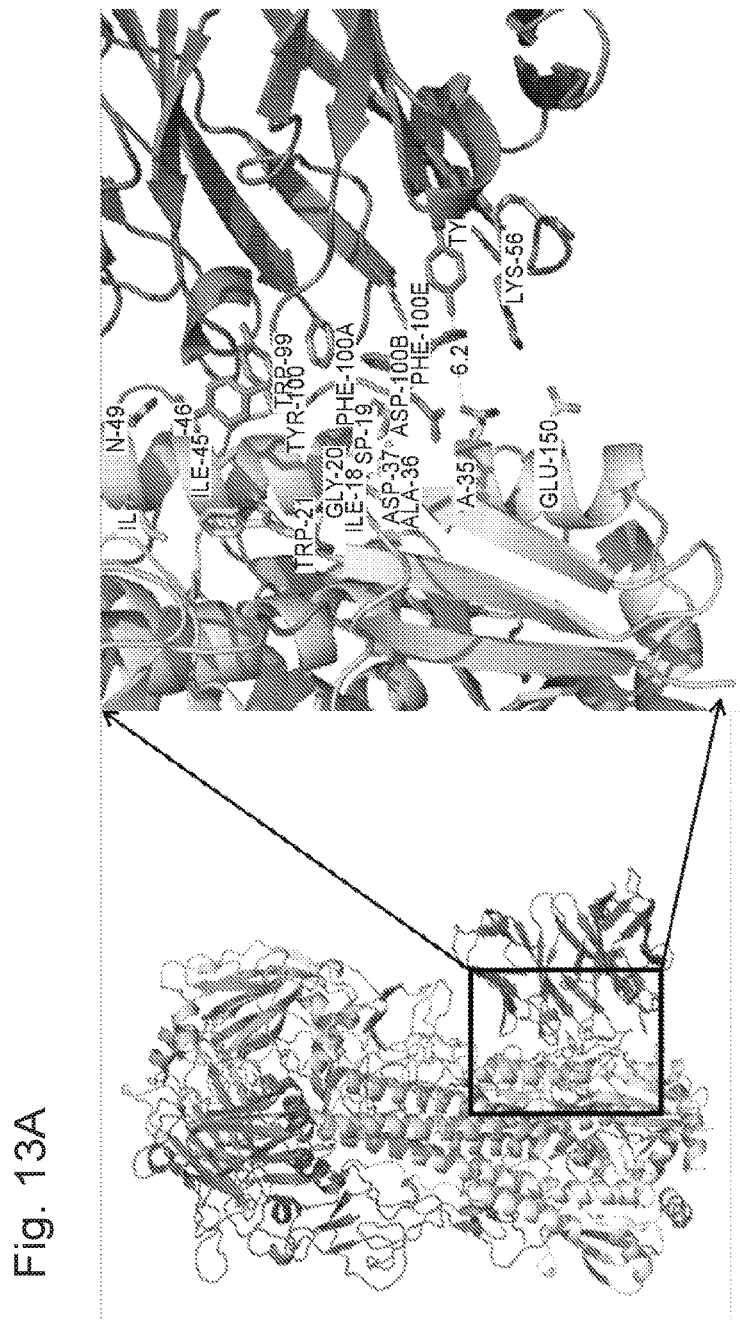
FIGS. 13 A-D are a series schematics that depict modeling of 3I14 and docking with H3/H5. The 3I14 epitope structure on the stalk of H3 trimer models is depicted in FIG. 13A.
FIG. 13B depicts the complex structures of IGVH3-30-derived bnAbs with HAs. The epitope residues on the HAs are displayed in surface representation and the CDR loops of bnAbs are shown are shown as ribbons. HA' of HA monomer is in wheat, HA2 is in salmon, and epitope residues are labeled as red. The key residues L38 and K39 are colored in yellow. Heavy chain CDRs of bnAbs are in blue and light chain CDRs are in cyan. 3I14 was homology modeled using the antibody-modeling module in BioLuminate and the model was superimposed to H3/FI6v3 complex structure before docking with RosettaDock. Other three IGHV3-30 bnAbs, FI6v3, 39.29 and MAb 3.1 were downloaded from Protein Data Bank.
FIG. 13C depicts the interaction of D94 in 3I14 with H3/H5. H3 is shown in cyan with K39 shown as stick; H5 is shown in green with E39 shown in stick; 3I14 is shown in orange in H3/3I14 model and in yellow in H5/3I14 model with D94 shown as stick.
FIG. 13D depicts the interactions of G31 of the 3I14 light chain with H3 in the H3/3I14 complex model. The helix A of HA2 domain of H3 is shown as ribbon in cyan; the light chain of 3I14 is shown as ribbon in orange; the main chain atoms of G31 are shown in stick and the side chain atoms of Q42 and D46 of H3 HA2 are shown in stick; the distance between G31 and H3 are illustrated by green dash lines and labeled in black. (The PyMOL Molecular Graphics System, Version 0.99 rc6 Schrödinger, LLC).
Figure 13B:
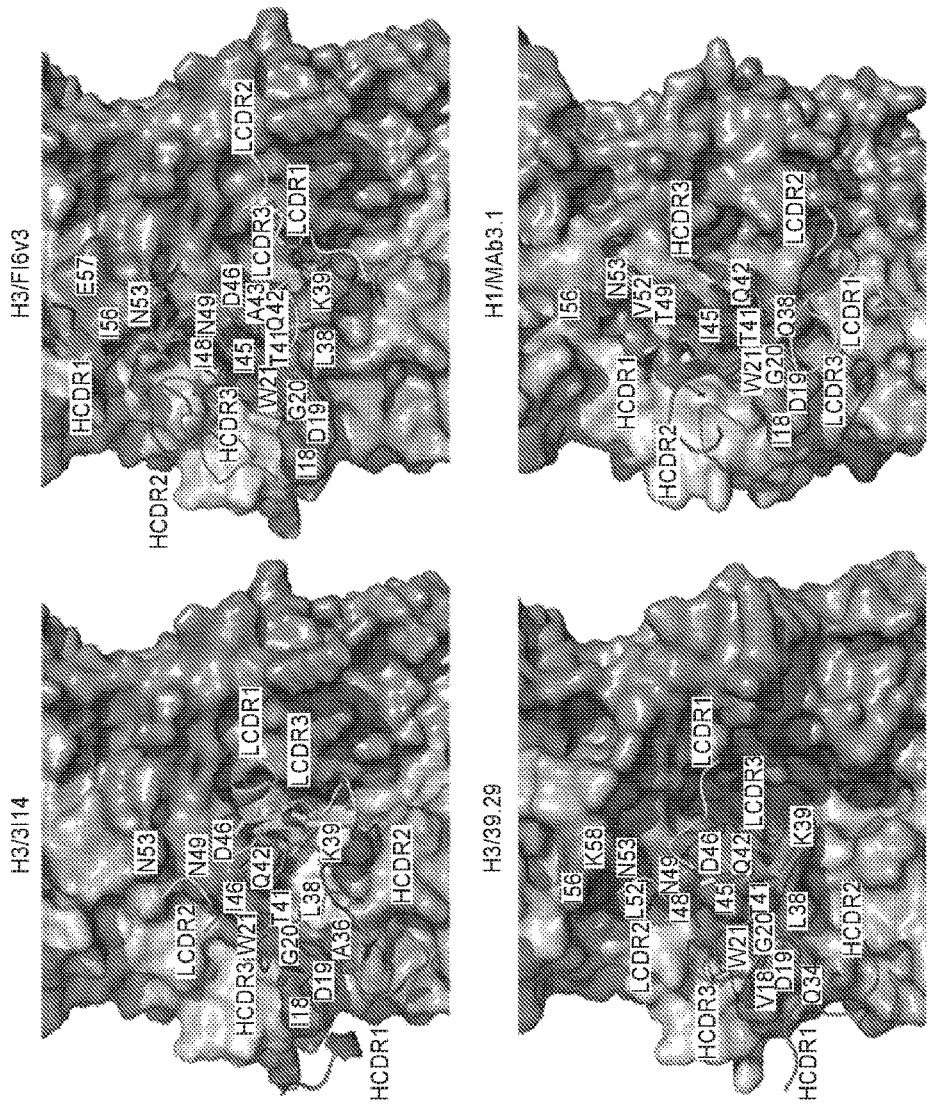
Figure 13C:
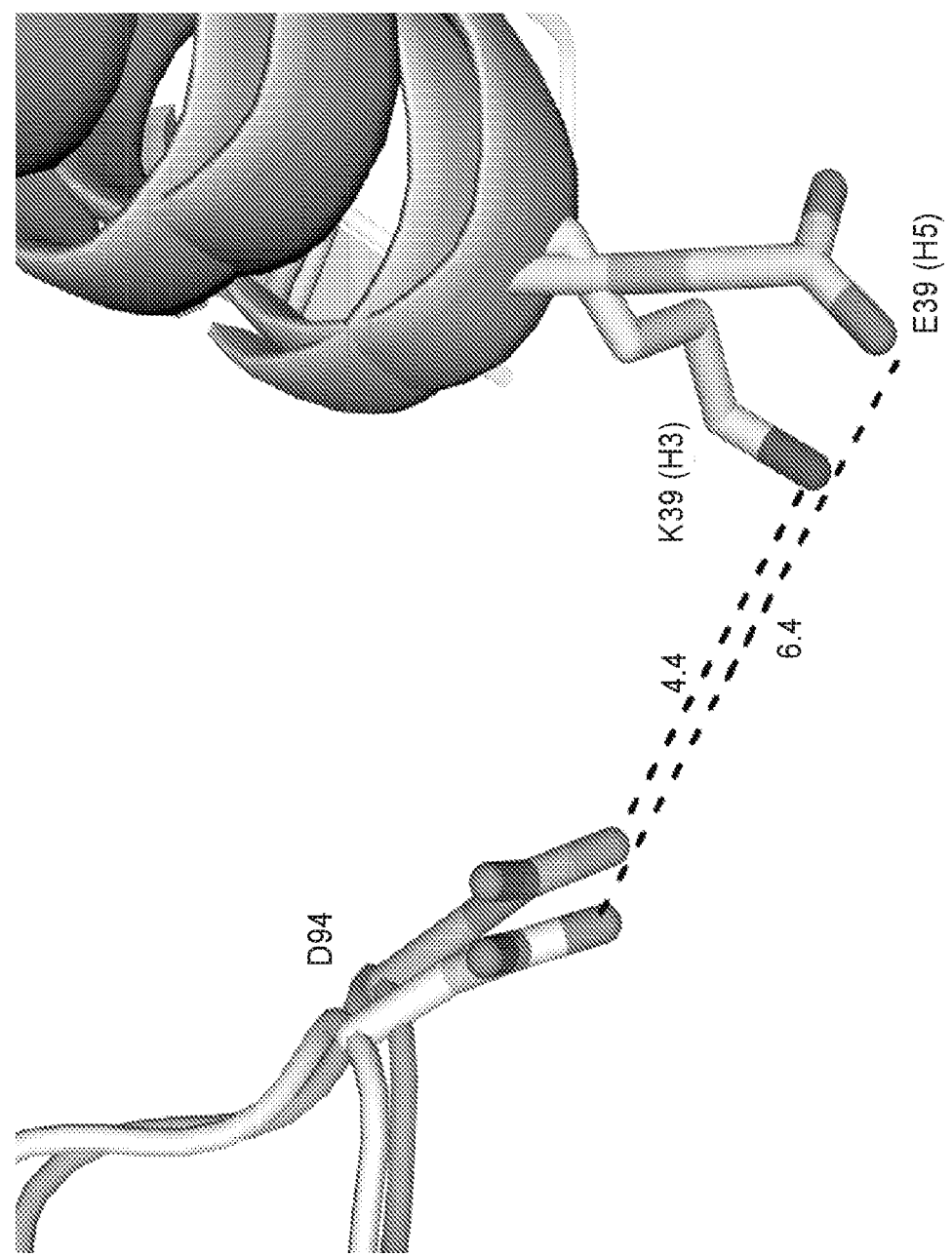
Figure 13D:
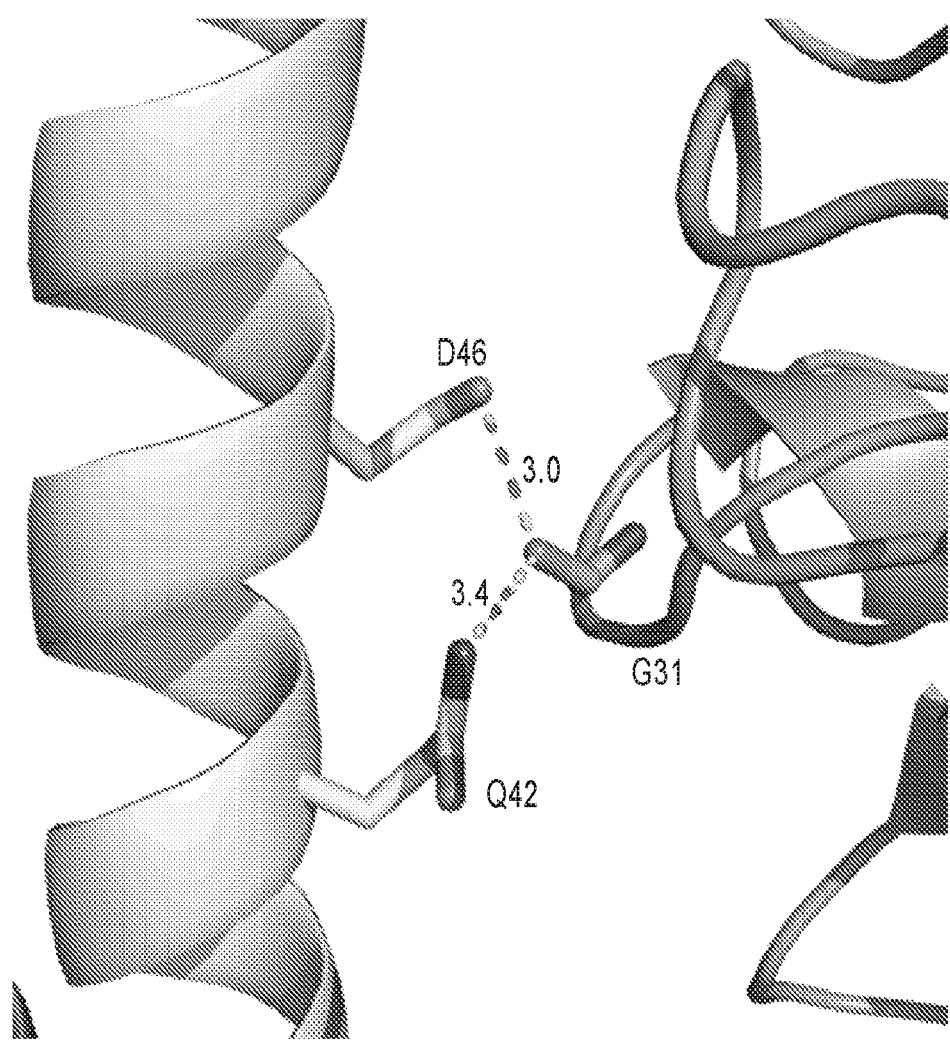

Based on these solved co-crystal structures, we chose from 1000 decoys the most similar binding models of 3I14/H3 (FIG. 13B) and 3I14/H5 complexes (not shown). A thorough analysis of the interfaces of the two complexes was carried out in order to understand why 3I14 binds H3/H1 stronger than H5 (Table 5). Energetic calculations[35] show very favorable binding contributions between D94 of 3I14 light chain and K39 in the H3 model, which may form a salt bridge while E39 is rotating away from D94 in the H5/3I14 model due to the electrical repulsion and may be unfavorable for H5 binding (FIG. 13C). In addition to H5, the E39 amino acid change is also found in group 1 H2, H6, H11 and H13 stains (Table 6). Another striking variation is at H3 position L38, where this residue is changed to K/R38 for some group 1 strains (Table 6). However, the binding contribution shows L/K38 contacts HCDR3 residues Y104, F105 and F109 in both models with favorable to very favorable binding (~70% of the total favorable free energy) and therefore we considered these residues to have a positive effect on binding to both HAs.

TABLE 5

Contact residues at H3/3I14 and H5/3I14 interfaces

| | 3I14 | | | | | | | | | | |
|---|---|---|---|---|---|---|---|---|---|---|---|
| | HCDR3 | | | | | LCDR1 | | | LCDR2 | | LCDR3 |
| | Y103 | Y104 | *F105\ | D106 | F109\*** | *G31\** | N32 | T33 | N52 | *S53\ | D94** |
| H3 | *I18* | W21, L38, I45 | D19, L38 | D19 | L38 | *Q42*, D46 | *Q42* | *Q42* | N49 | | K39 |
| H5 | D19, *I45* | D19, *K38*, T41, *I45* | D19, *K38* | D19 | *K38*, E39 | *Q42*, D46 | *Q42* | | T49 | N53 | E39 |

Contact residues defined by interatomic distances < 4 Å, except residue D94 in H3 and H5 complexes defined by distances < 5 Å and < 7 Å, respectively.
The color scheme indicates contributions to the binding energy: very favorable (underline); favorable (italics); neutral (underline and italics) and unfavorable (black).
*Residues indicate the somatic mutations of germline-encoded residues.

TABLE 6

Sequence comparison of 3I14 epitope among 16 HA subtypes

| | | $K_d$* | Relative $K_d$** | Fusion peptide | | | | | Helix A | | | | | | | |
|---|---|---|---|---|---|---|---|---|---|---|---|---|---|---|---|---|
| Group | Strains | (nM) | To CR9114 | 18 | 19 | 20 | 21 | 36 | 38 | 39 | 41 | 42 | 45 | 46 | 49 | 53 |
| Group 1 | H1-CA09 | 0.28 | — | V | D | G | W | A | L | *K* | T | Q | I | D | T | N |
| | H1-SI06 | 0.03 | — | V | D | G | W | A | Q | *K* | T | Q | I | N | T | N |
| | H1-PR8 | 0.08 | — | I | D | G | W | A | Q | *K* | T | Q | I | N | T | N |
| | H2-JP57 | — | — | V | D | G | W | A | *K* | E | T | Q | F | D | T | N |
| | H5-VN04 | 1.02 | — | V | D | G | W | A | *K* | E | T | Q | I | D | T | N |
| | H5-IN05 | 1.05 | — | V | D | G | W | A | *K* | E | T | Q | I | D | T | N |
| | H6-NY98 | — | — | V | D | G | W | A | *K* | E | T | Q | I | D | T | N |
| | H11-MEM74 | — | — | I | N | G | W | A | *K* | E | T | Q | I | D | T | N |
| | H13-MD77 | — | — | I | N | G | W | A | *K* | E | T | Q | I | D | T | N |
| | H16-SE06 | — | >20 nM | I | N | G | W | A | *K* | A | T | Q | I | D | T | N |
| | H8-ON68 | — | — | I | D | G | W | A | Q | *K* | T | Q | I | D | T | N |
| | H9-HK99 | 5.23 | — | V | A | G | W | A | *R* | D | T | Q | I | D | T | N |
| | H12-AB76 | — | >2.9 nM | V | S | G | W | A | *R* | D | T | Q | I | D | Q | N |
| Group 2 | H3-PE09 | 0.26 | — | V | D | G | W | A | L | *K* | T | Q | I | D | N | N |
| | H3-UY07 | 0.18 | — | V | D | G | W | A | L | *K* | T | Q | I | D | N | N |
| | H3-VIC11 | 0.33 | — | V | D | G | W | A | L | *K* | T | Q | I | D | N | N |
| | H4-NL05 | 0.29 | — | I | D | G | W | A | L | *K* | T | Q | I | D | N | N |
| | H14-AS82 | 0.29 | — | I | D | G | W | A | L | *K* | T | Q | I | D | N | N |
| | H7-NL219 | 0.03 | — | I | D | G | W | A | Y | *K* | T | Q | I | D | T | N |
| | H7-AH13 | 0.67 | — | I | D | G | W | A | Y | *K* | T | Q | I | D | T | N |
| | H10-SE02 | — | — | V | D | G | W | A | Y | *K* | T | Q | I | D | T | N |
| | H15-WA79 | — | <10 nM | I | D | G | W | A | Y | *K* | T | Q | I | D | T | N |

*$K_d$ determined by Surface Plasmon Resonance (SPR) Biosensor (FIG. 1B).
**Relative $K_d$ determined by Flow Cytometry (FIG. 2) and reference 16.
Residues carrying positively charged side chain are *bold and italicized*; while negatively charged side chain residues are bold and underlined.

Example 12: Structure of the 3I14 Epitope on the Stalk of H3 Trimer Models

FIG. 13 is a schematic representation of the 3I14 epitope on the stalk of H3. In the schematic, the heavy chain of 3I14 is shown in blue and the light chain is in magenta. The stalk of H3 trimer is color as salmon, green and cyan. Residue numbering is thoroughly on the basis of the H3 or Ab sequence.

3I14/H3 Docking

The 3I14 model was docked to the H3 trimer structure with RosettaDock as stand-alone software installed in our Linux machine. RosettaDock is chosen for its ability to handle local high-resolution docking and allow for extra rotamers and loop rearrangement. The 3I14 model was superimposed to 39.29 within the H3/39.29 complex structure before docking. The extra side-chain rotamers were added and the high resolution only protocol was carried out. 1000 decoys were generated and the clustered models with best score were analyzed thoroughly with PyMol. Given the that 3I14 competes with FI6 for binding to H3, we hypothesized that 3I14 adopts the same scheme to interact with H3 as 39.29, FI6 and Mab3.1. Therefore, the following criteria were applied when choosing the final model: the HCDR3 and the hydrophobic residues on the fusion peptide and helix A of HA2 of H3 must make close contact to form a hydrophobic core at the interface; the HCDR2 and HCDR1 residues make similar interactions with HCDR3 as other complexes; the light chain CDRs make mainly hydrophilic interactions with H3. Among the top 10 models from 1000 decoys, 6 models fit these criteria and they are very similar to each other. Therefore, the one with the best score within the 6 was chosen for further analysis.

Figures 14A, 14B:
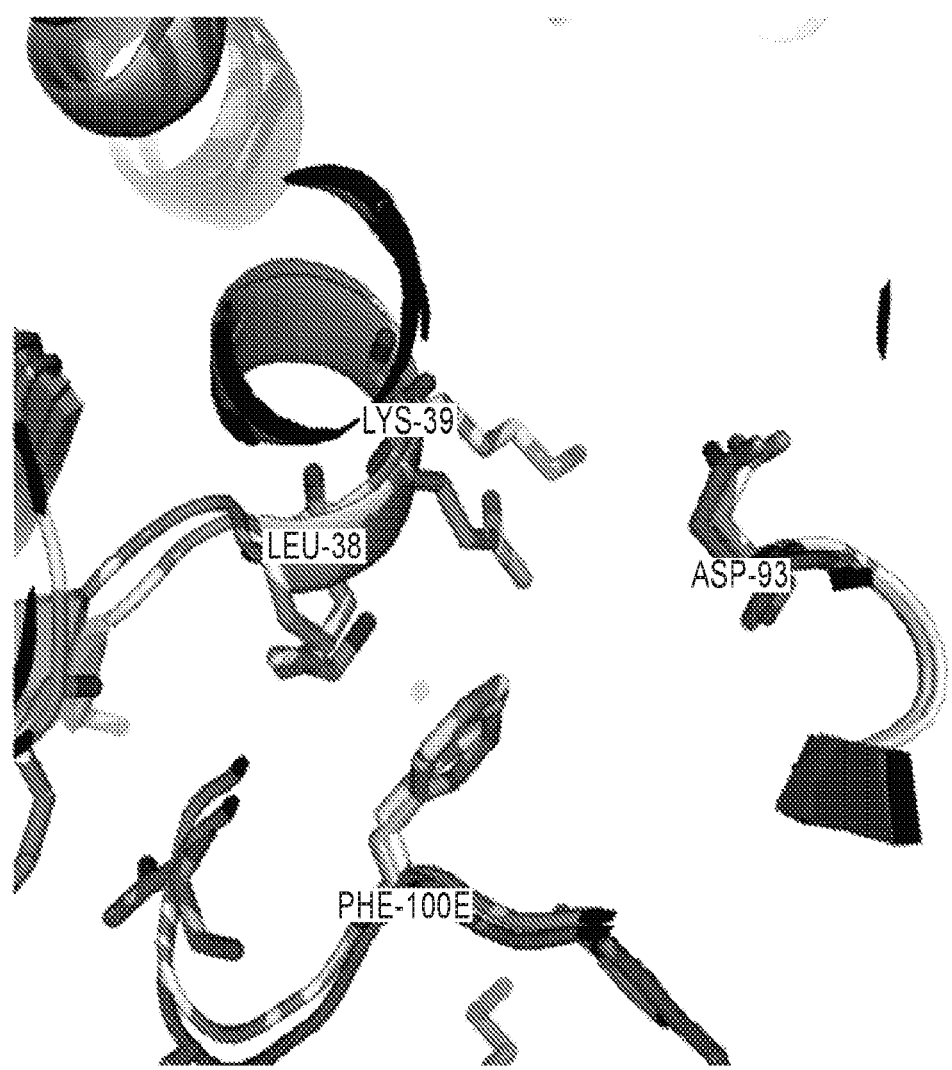
FIG. 14 depicts a sequence alignment (A) and structure superposition of H3/3I14 and H5/3I14 models (B).

Example 13 Sequence Alignment and Structure Superposition of H3/3I14 and H5/3I14 Models FIG. 14A depicts a sequence alignment of the stem epitopes of H3, H5 and influenza B. FIG. 14B depicts a structure superposition of H3/3I14 and H5/3I14 models at residue 38 and 39. H3 is shown as Cyan and H5 is shown as yellow; 3I14 from H3/3I14 model is shown as blue (Heavy chain) and yellow (Light chain) and 3I14 from H5/3I14 model is shown as orange. The H3 residues Leu38 and Lys39 are labeled. The residues F100F from heavy chain and D93 from light chain interact with 38 and 39 respectively and are also labeled.

3I14/H5 Docking

The H5/3I14 and influenza B/3I14 complexes were modeled in the same way as the 3I14/H3 complex. Both the 3I14 model and the H5 trimer or H3 trimer were superimposed to the H3/39.29 complex structure and the two structure files were merged into one 3I14/H5 complex or 3I14/Influenza B complex as the initial model for docking. Interestingly, similar models as those chosen for the H3/3I14 complex model are among the best models for both the H5/3I14 and influenza B/3I14 complexes. Therefore, these similar models were chosen as the final model for further analysis.

3I14 Engineering for Better H5 Binding

A thorough analysis of the H3/3I14 and H5/3I14 interfaces has been carried out in order to understand why 3I14 binds H3 stronger than H5. A sequence alignment of all epitope residues has shown that the most striking variation is that L38-K39 in H3 becomes K38-39E in H5 (FIG. 14A). L38 is part of the hydrophobic core in the H3/3I14 model and it interacts with F100F from the HCDR3 of 3I14 (FIG. 14B). Surprisingly, the K38 in the H5/3I14 model is able to make the same contacts by pointing the charged amine group into the solvent and leaving the aliphatic chain facing F100F. According to the models, this mutation does not appear to be able to affect the binding affinity. On the contrary, K39 makes contacts with D94 from the light chain of 3I14 in the H3/3I14 model while E39 is rotating away from D94 in the H5/3I14 model due to the electrical repulsion (FIG. 14B). Apparently, the K39E mutation is not favorable for H5 binding and perhaps this is the reason that 3I14 has weaker binding to H5 weaker in comparison to H3. In order to test this hypothesis, the residues at position 38-39 of HA from different subtypes were examined in comparison with their ability to bind 3I14. A strong correlation can be unveiled that HAs with L38 and K39 bind 3I14 strongly and HAs with K38 and E39 have weaker binding. Taken together, we hypothesize that the D94K mutation in the light chain of 3I14 will reverse the binding preference of 3I14 toward H5 and lower the binding affinity to H3. In addition, we hypothesize that D94N 3I14 variant will bind equally well to both H3 and H5. We do not expect the D94N mutation will lead to weakening H3 binding since the major driving force for the interaction is the hydrophobic interaction from HCDR3. As long as the interaction at this position is not repulsive, it should not affect the affinity significantly.

Example 14: 3I14 WT and VLD94N Mutations IgG1 Binding (Kd Values) to Recombinant H5-VN04 (A) and H3-PEO9 (B)

3I14 VLD94N Variant Improves the Binding and Neutralization Activity to H5

To eliminate the proposed repulsive effect of E39 and D94, we hypothesized a single Asp-to-Asn (D to N) mutation that leads to a loss of a negative charge at the site will bind equally well to both H3 and H5. To examine this structural-based modification, we first evaluated the binding affinity of both WT 3I14 and VLD94N variant IgG1. As shown in Table 3, VLD94N variant increased binding affinity to H5 by nearly 10-fold but did not cause any significant change in binding to H3. Interestingly, the higher affinity to H5 was also due to decreased dissociation rates, while association rates were equal (Table 7 and FIG. 15).

TABLE 7

The binding affinity of 3I14 VLD94N variants.

| 3I14 Variants | H5-VN04 | | | H3-PE09 | | |
|---|---|---|---|---|---|---|
| | $K_d$ (nM) | $K_{on}$ ($M^{-1}s^{-1}$) | $K_{off}$ ($s^{-1}$) | $K_d$ (nM) | $K_{on}$ ($M^{-1}s^{-1}$) | $K_{off}$ ($s^{-1}$) |
| 3I14 WT | 1.02 | 3.27E+05 | 3.87E−04 | 0.263 | 1.52E+05 | 3.99E−05 |
| 3I14 VLD94N | 0.187 | 3.83E+05 | 7.74E−05 | 0.308 | 1.77E+05 | 5.44E−05 |

Figure 16A:
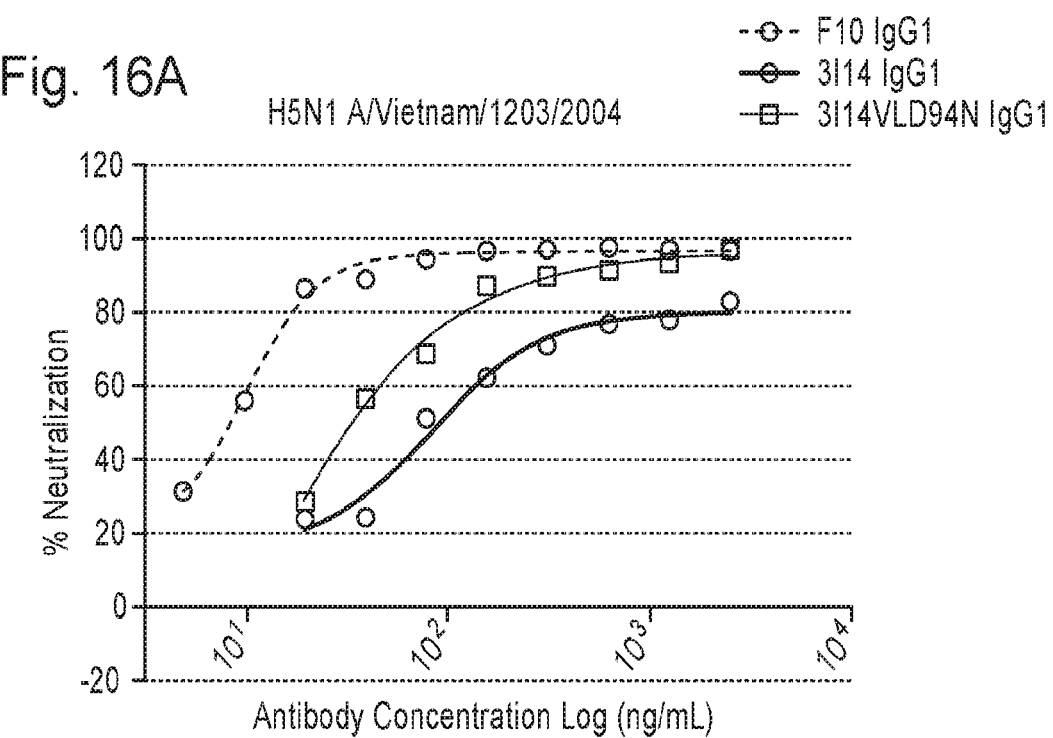
FIG. 16A-D are a series of graphs that depict neutralization values of 3I14 WT and VLD94N mutant IgG1 following incubation with pseudotyped virus H5N1-VN04 and infectious virus H3N2-BR07. Depicted in FIGS. 16C and 16D, the 3I14 (black) and VLD94N variant (red) neutralized pseudotyped virus H5N1-VN04 (C) and H3N2-BR07 virus (D). This data represent average neutralization titers of 2-3 independent experiments.
Figure 16B:
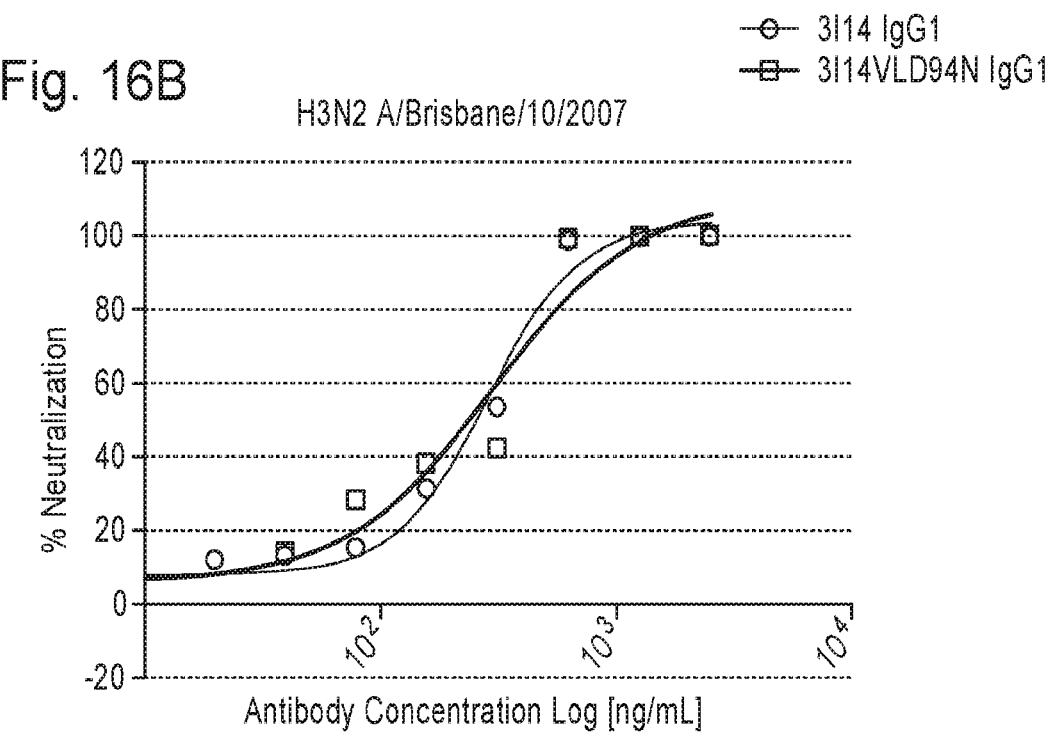
Figure 16C:
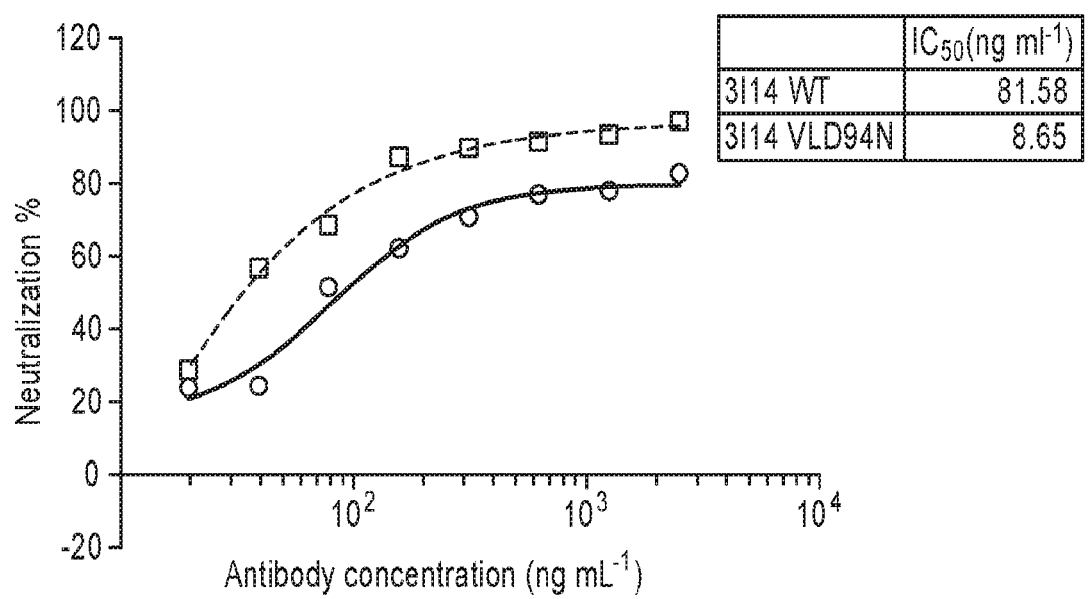
Figure 16D:
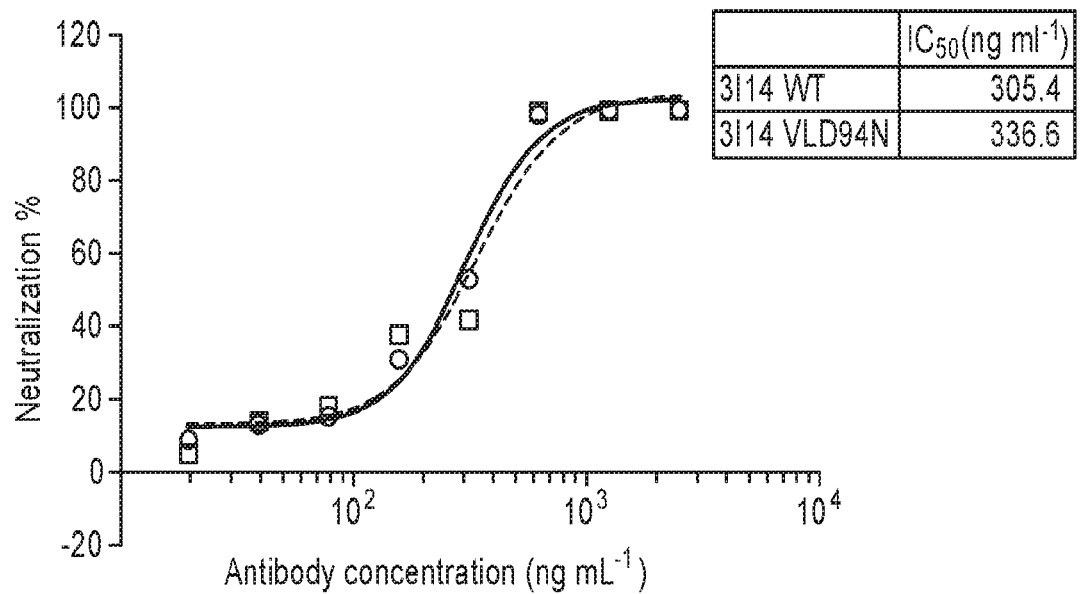

We also performed neutralization assays to assess the activity of 3I14 VLD94N variant against H5 pseudotyped or H3 infectious virus (FIGS. 16C and 16D). Compared with 3I14, the VLD94N variant neutralized H5-VN04 pseudovirus with 10-fold higher potency ($IC_{50}$: 8.65 ng ml$^{-1}$ vs. 81.58 ng ml$^{-1}$), (FIG. 16C). Meanwhile, the neutralization activity against H3-BR07 remained intact of VLD94N variant ($IC_{50}$: 336.6 ng ml$^{-1}$ vs. 305.4 ng ml$^{-1}$) (FIG. 16D). These results demonstrate that the optimized 3I14 VLD94N variant lead to an increase in binding and neutralizing ability to H5 while maintaining its efficacy to H3.

Figure 15A:
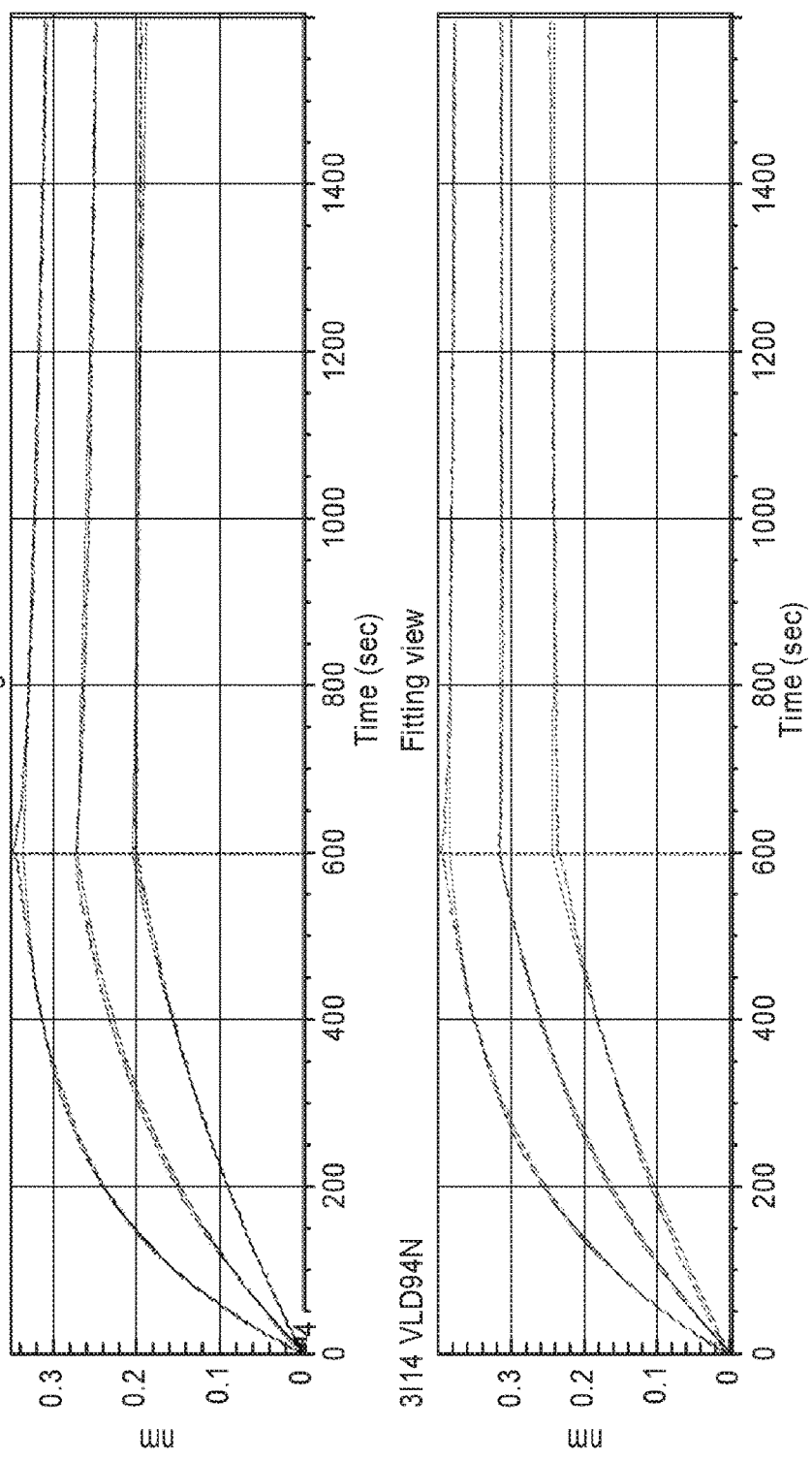
Figure 15C:
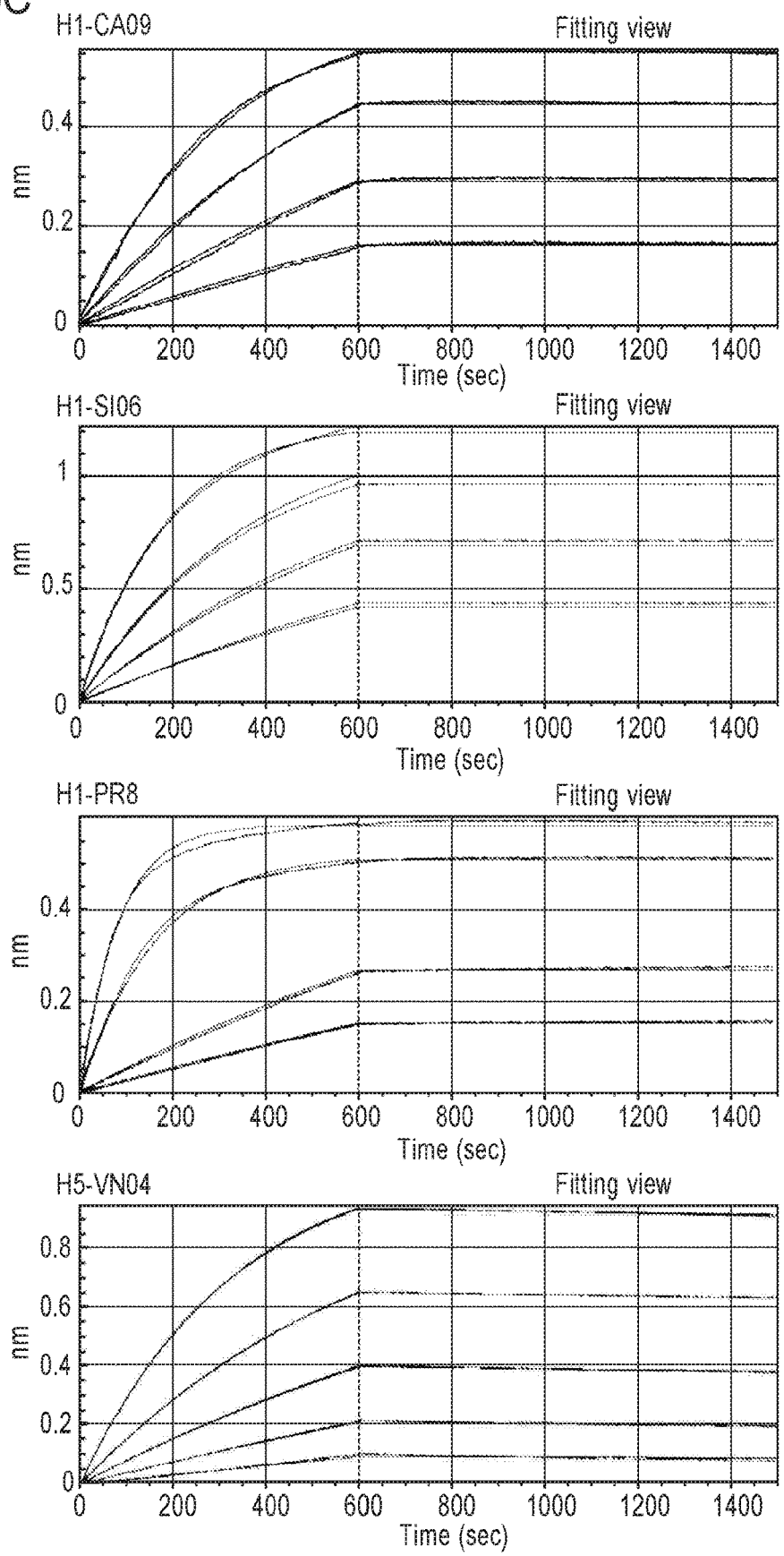
Figure 15D:
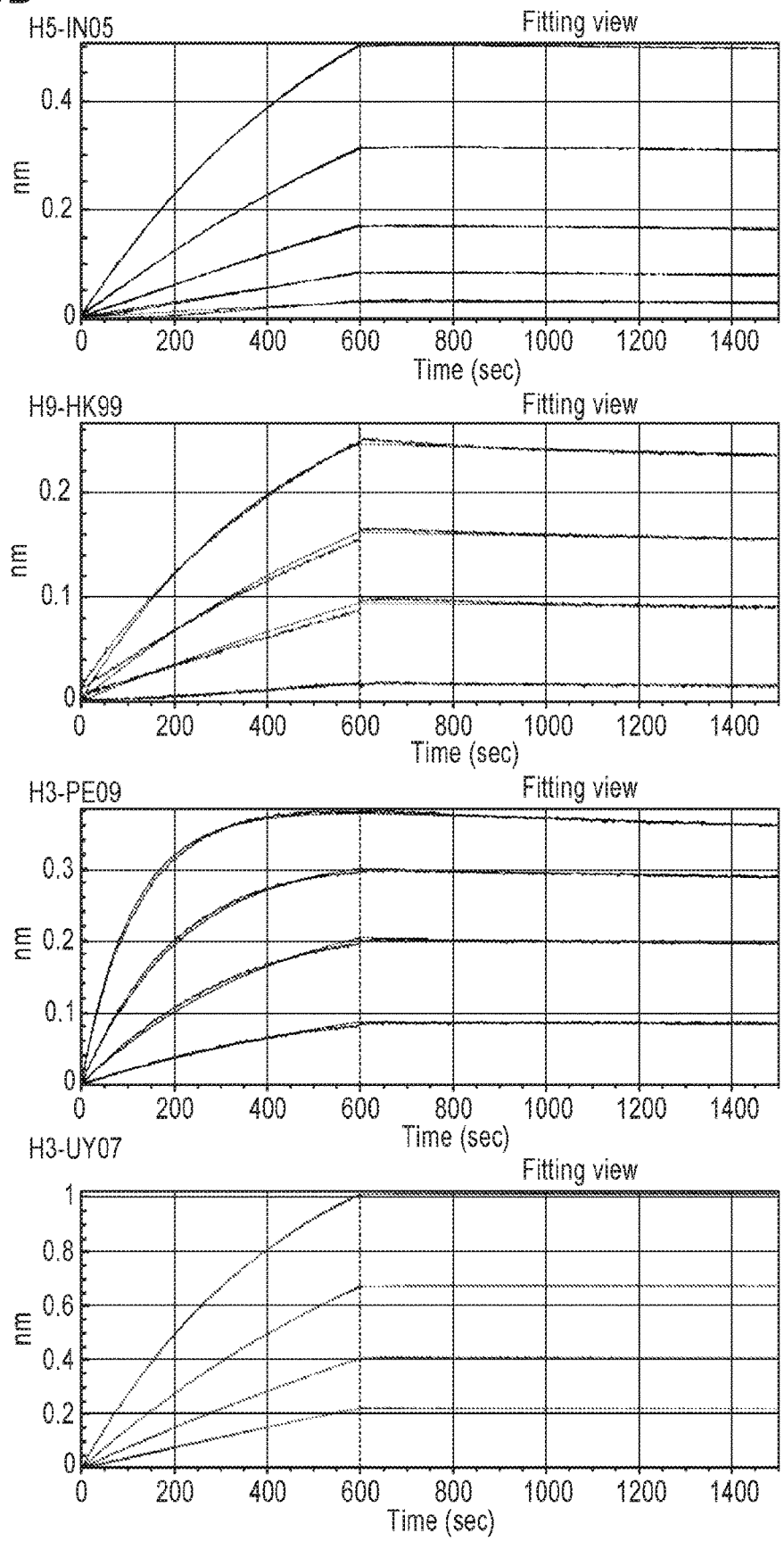
Figure 15E:
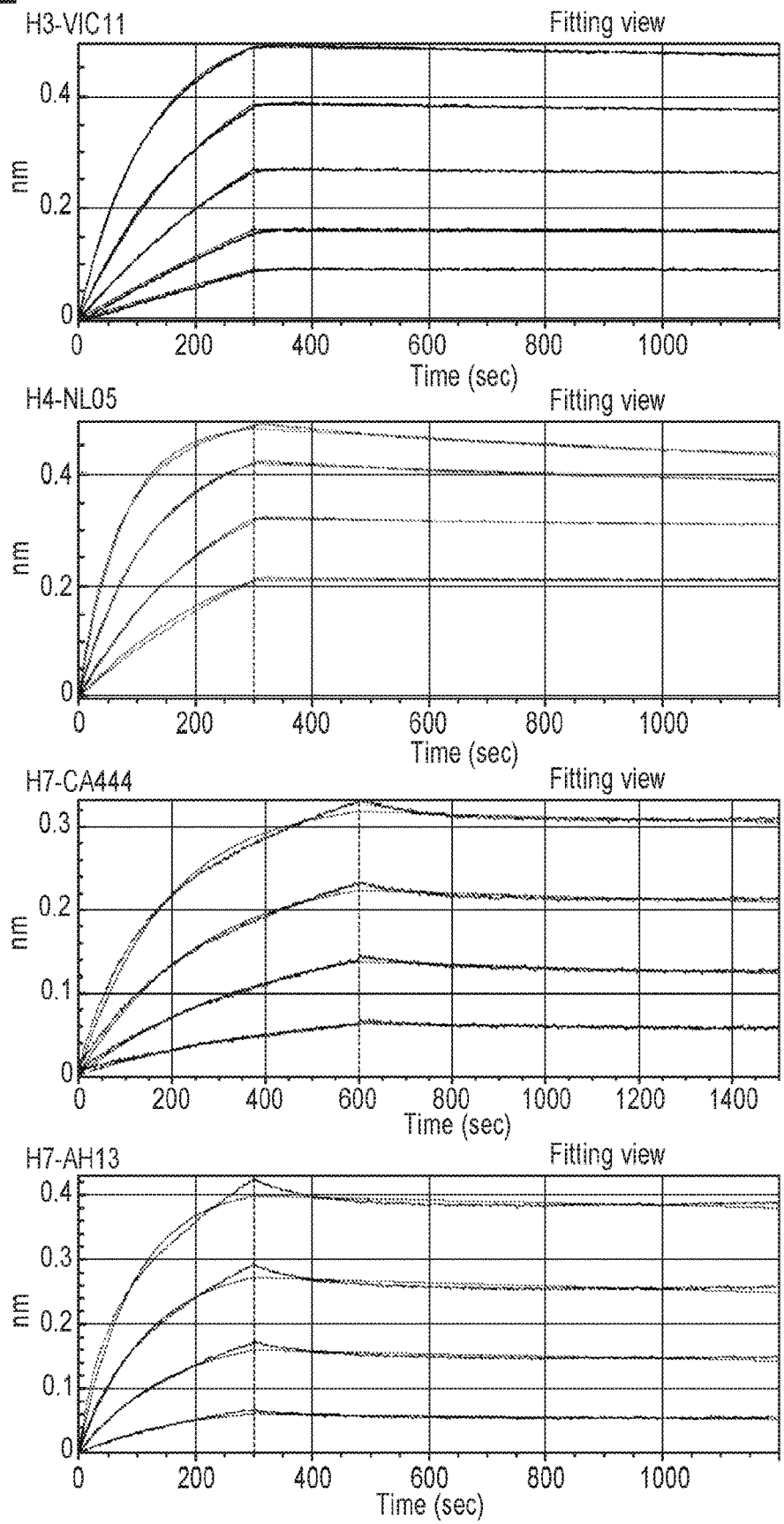

Further experiments demonstrated that 3I14 bound to H3-PEO9 with $K_d$ Value of 1.96 nM, whereas the affinity of 3I14 VLD94N mutant to H3-PEO9 was similar (mean $K_d$=2.34 n M). The D94N mutation does not lead to weakening of H3 binding but does result in an increase in the binding affinity to H5 (FIGS. 15A and 15B).

Example 15: 3I14 WT and VLD94N Mutant IgG1 Neutralize Pseudotyping Virus H5N1-VN04 and Infectious Virus H3N2-BR07

FIG. 16 is a series of graphs that depict the neutralization of H5N1-VN04 and H3N2-BR07 infection virus. The 3I14 WT (BLACK) and VLD94N mutant (RED) neutralized pseudotyping virus H5N1-VN04 (A) and H3N2 BR07 virus (B). Anti-group 1 mAb F10 (BLUE) was used as controls. These data represent average neutralization titer of 2-3 independent experiments.

3I14 VLD94N mutant IgG1 neutralized pseudoviruses H5N1-VN04 with higher IC50 values than 3I14 WT, while it also neutralized H3N2 virus with similar IC50 values.

Example 16: Engineered Yeast Display for Isolation of 3I14 Variant with Increased Binding to H5

7 yeast display libraries were created by randomizing residues of HCDR1, HCDR2, HCDR3, LCDR1, LCDR2, LCDR3 and LCDR4. These yeast display libraries were used to generate a pool of single chain 3I14 variants, which will be selected and cloned into the yeast display vector pCT-CON2. The isolated construct will attach a c-Myc tag at the C-terminus of the antibody to serve as a marker for presentation. The antibody expression and surface display will be induced by growing the library in SGCAA medium at 20 degree for 24-48 hrs. The successful presentation of the 3I14 variants will be detected by anti-c-Myc FITC labeling. H5

HA will be labeled with a fluorescent label and added to the staining for 1 hr. The unbound reagent will be washed away and the labeled library will be sorted for H5 HA positive clones.

Figure 18:
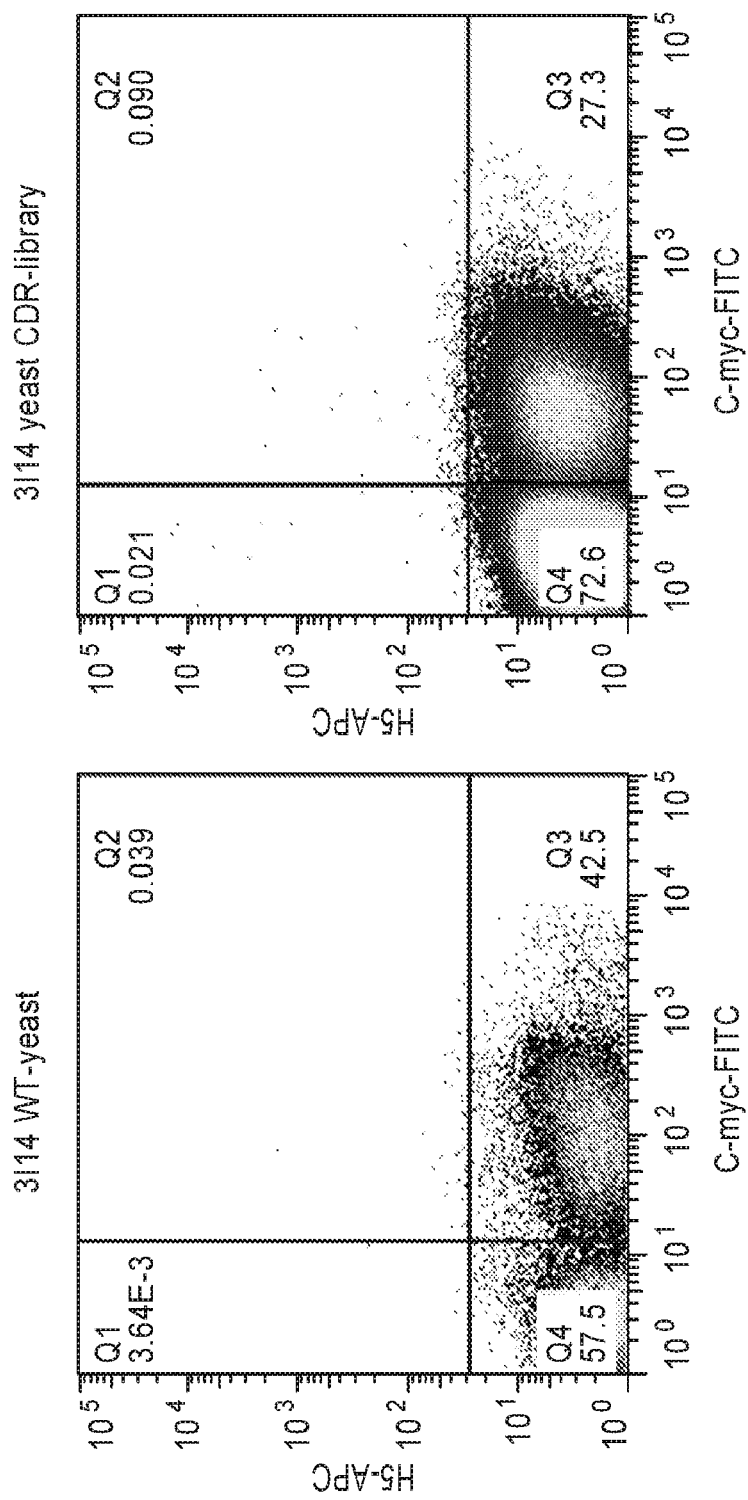
FIG. 18 is a series of flow cytometry graphs that depicts binding of 3I14-WT yeast in comparison to binding of the engineered 3I14 yeast-CDR library to H5. The 3I14 yeast-CDR library was engineered using yeast display for variants that increase binding to H5.

As shown in FIG. 18, both 3I14 WT-yeast and CDR-libraries were positive for C-myc and H5, as demonstrated by FACS analysis. The double positive H5 and c-myc positive population was increased in the 3I14 yeast CDR library from 0.039% to 0.090%, in comparison to the 3I14-WT-yeast library.

In future studies, the positive clones will be grown and sorted again for three times to enrich the positive population. The positive clones will be verified by FACS analysis and identified by sequencing. Yeast display in combination with FACS sorting has been proven successful for antibody engineering and will be used to isolate 3I14 variant clones that are capable of binding to influenza B HA. Once initial binders to influenza B HA are identified, the subsequent rounds of screening will be carried out with multi-color sorting, that is, H3, H5 and influenza B HA will be labeled with different fluorescent labels and triple positive 3I14 variants will be sorted.

Example 17: Epitope Mapping and Binding Competition

Figure 2:
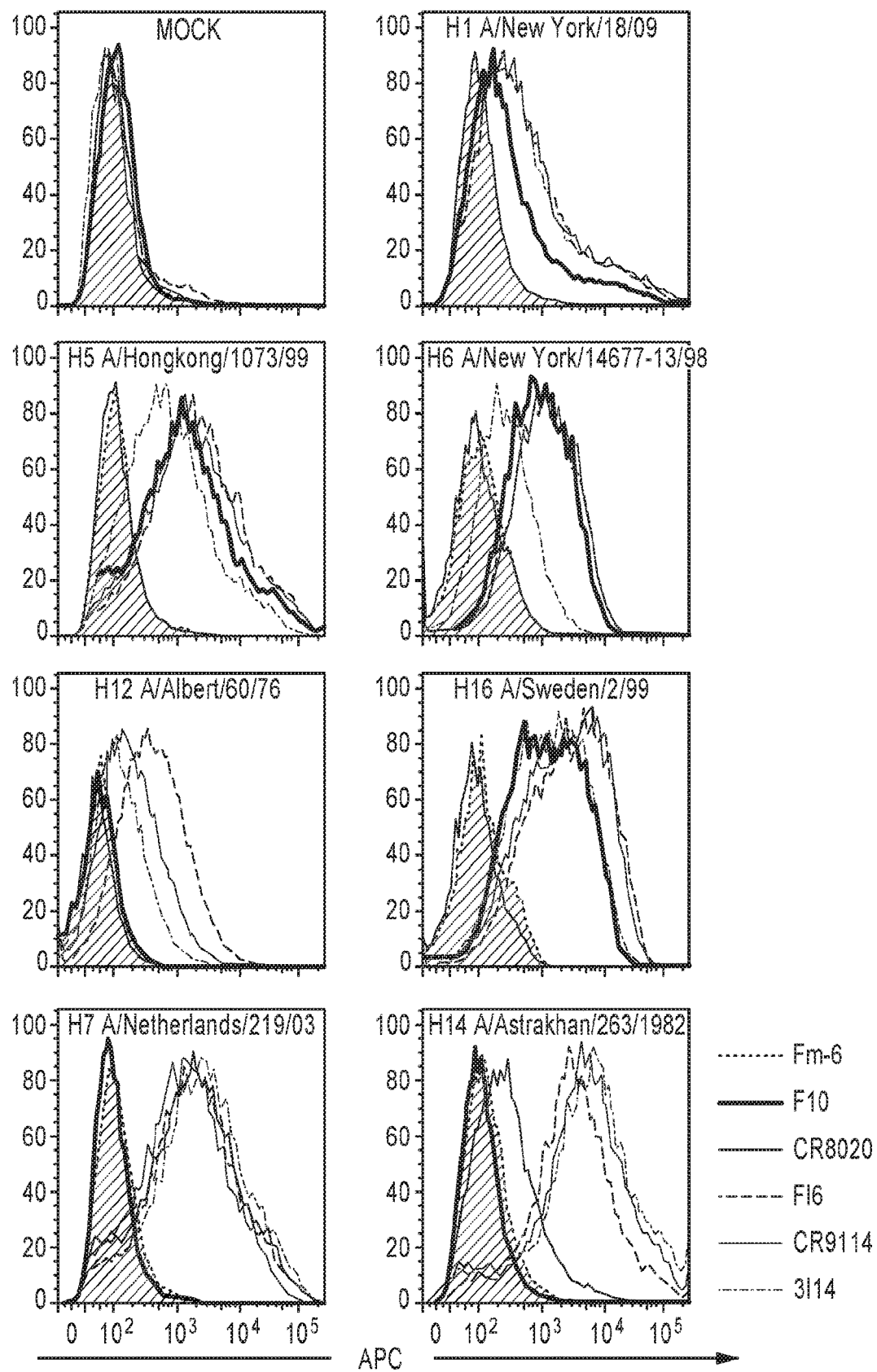
FIG. 2 is a series of FACS graphs that depict 3I14 binding to a broad range of group 1 and group 2 HAs. 293T cells were transiently transfected with different HA-expressing plasmids, followed by staining with the purified scFvFc antibodies and APC-labeled mouse anti-human Fc antibody. Binding of 3I14 (red line), F10 (group 1-specific, green line), CR8020 (group 2-specific, blue line), FI6v3 (group 1 & 2 specific, purple line), CR9114 (group 1 & 2 specific, orange line), and irrelevant mAb Fm-6 (anti-SARS virus, grey filled histogram) were analyzed by flow cytometry.
Figure 2:
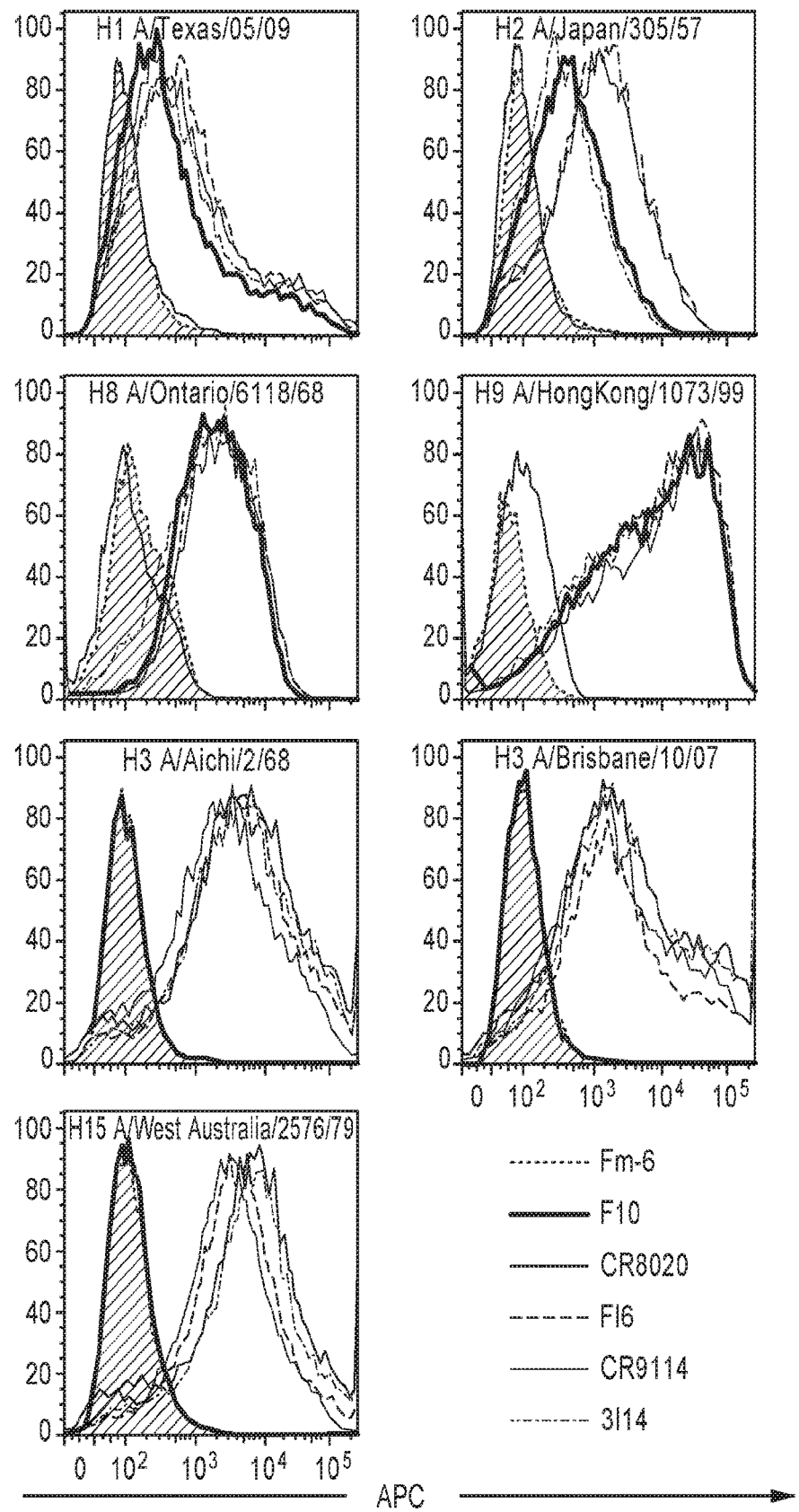
Figure 2:
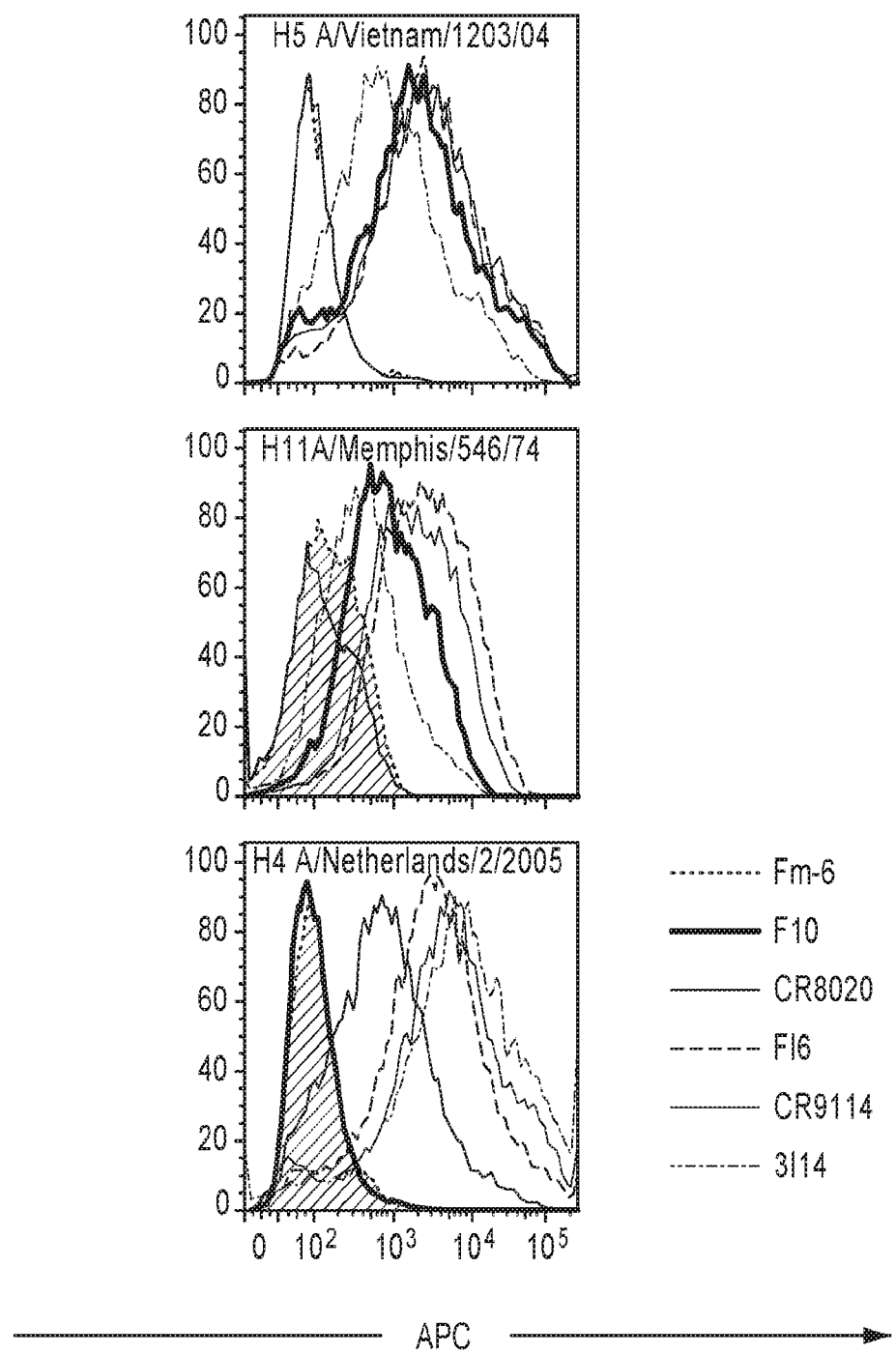
Figure 3A:
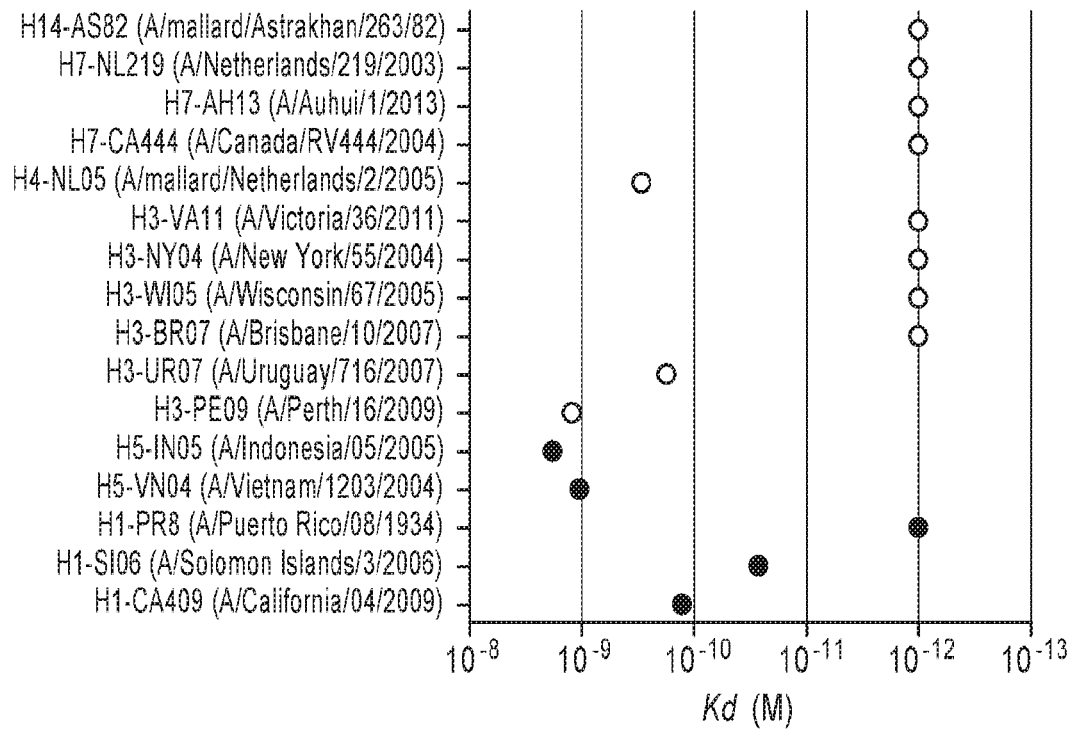
FIG. 3 is a series of graphs that depicts 3I14 IgG1 (A) binding ($K_d$ values) or scFvFc Ab (B) binding ($K_d$ values) to recombinant HAs that are representative of group 1 (red) or group 2 (blue) subtypes.
Figure 3B:
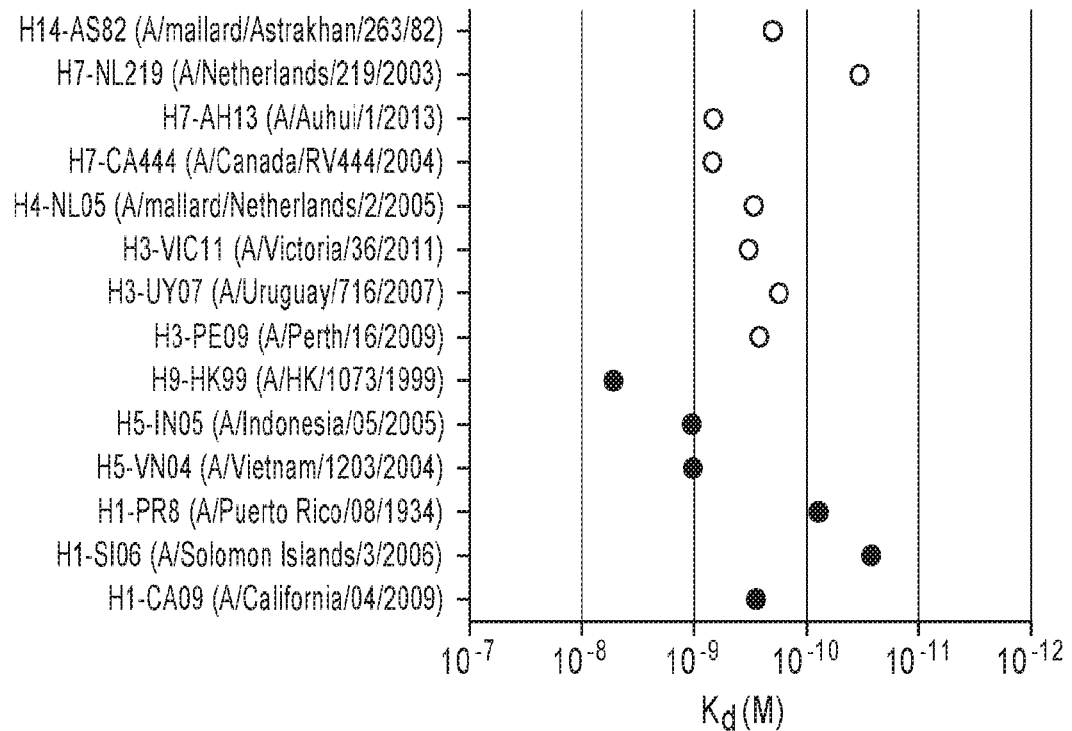
Figure 19:
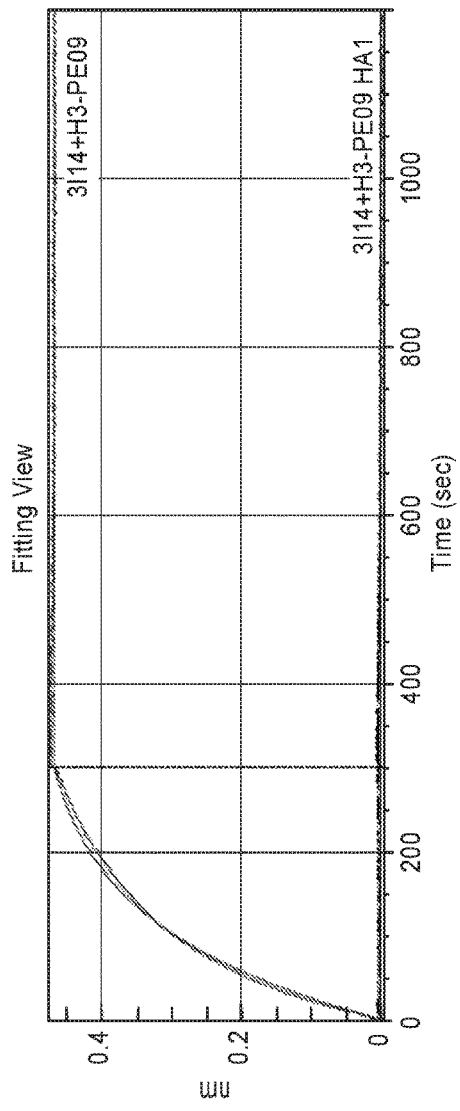
FIG. 19 is a graph that depicts 3I14 scFvFc Ab binding to full-length or HA1 of recombinant H3-PE09.

To investigate the epitope of HA for 3I14 recognition, we assessed its binding activity to either full-length of HA or HA1 subunit in Octet® RED96 instrument. 3I14 bound trimeric full-length H3 strain, A/Perth/16/09 (PE-09), but did not bind its HA' subunit (FIG. 19). We further performed the binding competition assay between 3I14 and other stem-directed bnAbs: FI6v3, CR9114, 39.29, F10 and CR8020 (FIG. 2). 3I14 Fab strongly inhibits the binding of other anti-stem Abs CR9114, FI6v3 and 39.29 to H3-BR07 but not with the head-directed, anti-H3 mAb E730 (unpublished antibody sequence) (FIG. 10). 3I14 also competes with CR8020, which is directed against a more membrane-proximal epitope 14. 3I14 partially inhibits the binding of 39.29 and F10 to H5-VN04 but does not inhibit the binding of the anti-H5 head antibody 2A12 (FIG. 2e,f). These results demonstrate that 3I14 is overlapping with or very close to the known stem epitopes of other bnAbs. In addition, 3I14 is a potent inhibitor of H3 and moderate inhibitor of H5. These results are consistent with the affinity measurements of 3I14 binding to H3 and H5.

Example 18: Materials and Methods

Cells

Fresh PBMCs of 7 healthy adults that reported no recent seasonal influenza vaccination were obtained using discarded "collars" collected during leukapheresis at the DFCI Kraft Family Blood Donor Center in December 2012 under an IRB-approved human protocol. Madin-Darby cainine kidney (MDCK) cells, 293T and 293F cells were obtained from American Type Culture collection (Manassas, Va., USA)

Preparation of Recombinant Hemagglutinins

The extracellular domain of H3 (A/Brisbane/10/2007), residues 17 to 531, was expressed as fusion protein included a C-terminal peptide containing Avitag (amino acid sequence: GGGLNDIFEAQKIEWHE), thrombin cleavage site, trimerization T4 fibritin foldon domain and six histidine residues. The fusion protein H3-ATTH was expressed in 293F cells and purified from the supernatant by Ni-NTA affinity chromatography. Purified recombinant HA protein was cleaved by thrombin enzyme (Novagen, Darmstadt, Germany), then biotinylated with BirA enzyme (Avidity, Aurora, Colo.) according to the manufacturer's instructions.

The full length HA genes of A/New York/18/09 (H1-NY09), A/Texas/05/09 (H1-TX09), A/Japan/305/57 (H2-JP57), A/Aichi/2/68 (H3-A2/68), A/Brisbane/10/07 (H3-BR07), A/Netherlands/2/2005 (H4-NL05), A/Vietnam/1203/04 (H5-VN04), A/Hongkong/1073/99 (H5-HK99), A/chicken/New York/14677-13/98 (H6-NY98), A/Netherlands/219/03 (H7-NL219), A/turkey/Ontario/6118/68 (H8-0N68), A/HongKong/1073/99 (H9-HK99), A/duck/Memphis/546/74 (H11-MEM74), A/duck/Alberta/60/76 (H12-AB76), A/mallard/Astrakhan/263/1982 (H14-AS82), A/shearwater/West Australia/2576/79 (H15-WA79) and A/black-headed gull/Sweden/2/99 (H16-SE06) were cloned into pcDNA3.1 vector and transfected into 293T/17 cells to produce cell surface expressed HA.

Recombinant full length HA proteins of H1 subtypes A/California/04/09 (H1-CA09), A/Solomon Islands/3/06 (H1-SI06) and A/Puerto Rico/8/34 (H1-PR8); H3 A/Perth/16/09 (H3-PE09), A/Uruguay/716/07 (H3-UY07), and A/Victoria/341/11 (H3-VIC11); H5 A/Vietnam/1203/04 (H5-VN04) and A/Indonesia/05/05 (H5-ID05); H7 A/Netherlands/219/03 (H7-NL219), A/Canada/RV444/04 (H7-CA444) and A/Anhui/1/13 (H7-AH13); H9 A/Hong Kong/1073/99 (H9-HK99) were obtained from the NIH BEIR Repository (NIH, Manassas, Va.). Recombinant full length HAs of subtypes H4 A/mallard/Netherlands/2/05 (H4-NL05) and H14 A/mallard/Astrakhan/263/82 (H14-AS82) were kindly gifted from Dr. R. C. Liddington (Burnham Institute for Medical Research, CA, USA).

Preparation of Influenza Viruses and HA Pseudotyped Viruses

Wild type influenza viruses A/California/4/09 (H1N1-CA09), A/Puerto Rico/8/34 (H1N1-PR8), A/Perth/16/09 (H3N2-PE09), A/Aichi/2/68 (H3N2-A2/68), A/Hong kong/8/68 (H3N2-HK68), A/Sydney/5/97 (H3N2-SY97), A/Brisbane/10/07 (H3N2-BR07), A/Wisconsin/67/05 (HA, NA)×A/Puerto Rico/8/34 (H3N2), A/Aichi/2/68 (HA, NA)×A/Puerto Rico/8/34 (H3N2) and A/Nanchang/993/95 (H3N2-NC95) were obtained from the NIH BEIR Repository (NIH, Manassas, Va.), and grown in Madin-Darby canine kidney (MDCK) cells by standard viral culture techniques. A/Brisbane/10/2007-ma (H3N2) used in animal challenge studies is a mouse-adapted virus derived from a PR8 reassortant virus x-171[46].

The full length HA genes of A/Vietnam/1203/04 (H5-VN04), A/Hong Kong/156/97 (H5-HK97), A/Netherlands/219/07 (H7-NL219), A/FPV/Rostock/1934 (H7-FPV) and neuramidase gene N1 of H5-VN04 (Genbank accession AAW80723) were cloned into pcDNA3.1 plasmids, separately. The Env-Pseudotyped luciferase reporter viruses were produced in 293T/17 cells as previously described[12]. Briefly, the pcDNA3.1-H5-VN04, H5-HK97, H7-NL219 or H7-FPV plasmids were separately co-transfected into 293T/17 cells with the N1-expressing plasmid pcDNA3.1-N1-VN04, HIV packaging vector pCMVR8.2 and reporter vector pHIV-Luc. Viral supernatants were harvested at 48 h post-transfection. Viral titration was evaluated by measuring luciferase activity using the POLARstar Omega Microplate Reader (BMG LABTECH, Ortenberg, Germany).

FACS Sorting of H3 Binding Memory Cells

Fresh PBMCs were isolated from the collected blood by use of the Ficoll-Paque gradient (GE HealthCare). The CD19$^-$/CD27$^+$ B cells were stained with biotinylated H3-ATTH and allophycocyanin (APC)-labeled streptavidin. Single H3-reactive memory B cells were sorted into 384-well plate. After 14 days of expansion, the supernatants were tested for reactivity to recombinant H1 (H1-CA09), H3 (H3-BR07), and H7 (H7-CA444) HA proteins and were analyzed by the Meso Scale Discovery multiplex (MSD, Rockville, Md.). Subsequently, the reactive supernatants were measured in vitro neutralizing activity against H3N2-BR07. All H3N2 neutralizing antibodies were rescued by single cell RT-PCR using primers as previously described[47].

Expression and Purification of 3I14 scFV and IgG Antibodies

Figure 1B:
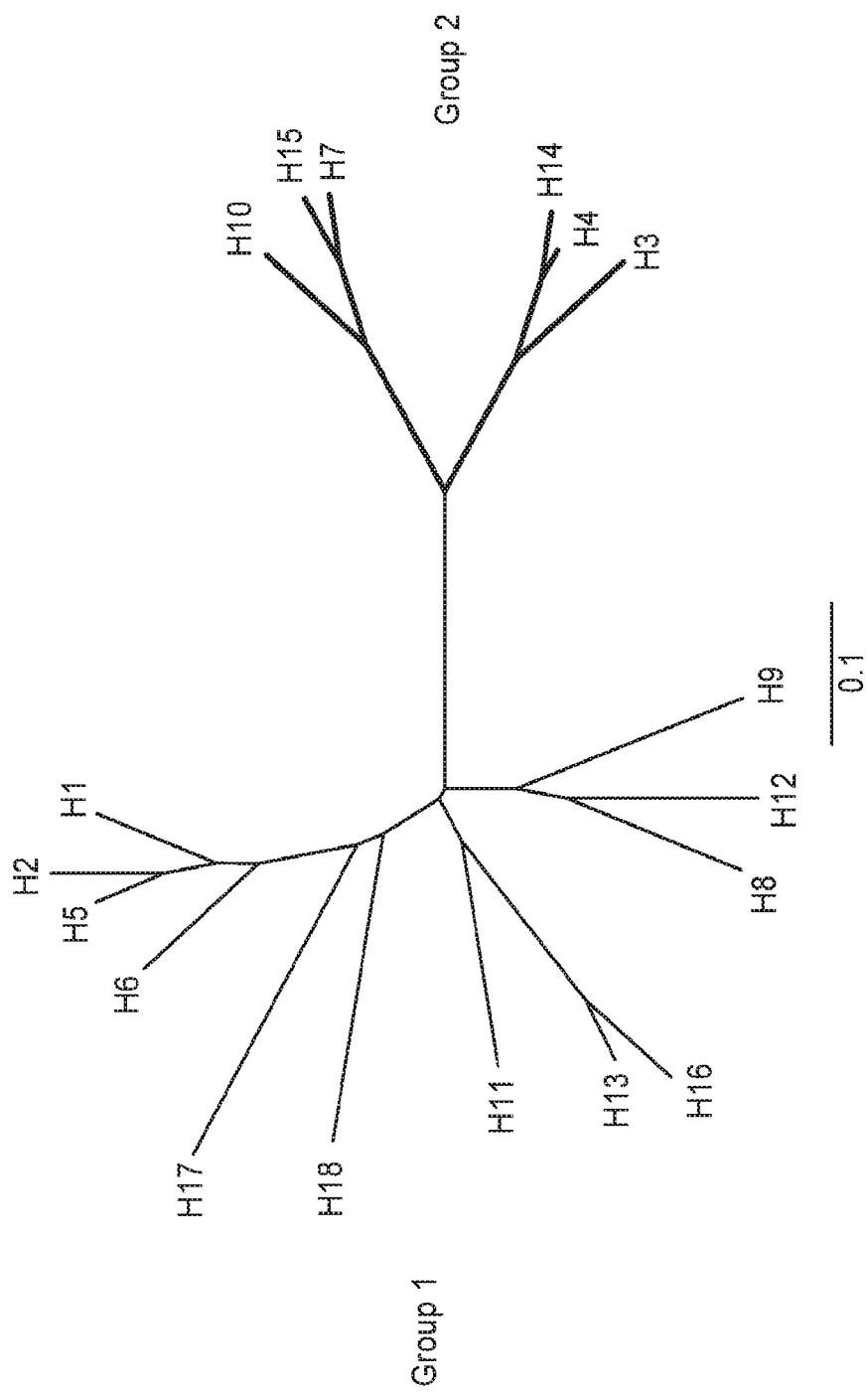
FIG. 1B depicts a phylogenetic tree of the 18 HA subtypes of influenza A viruses based on amino-acid sequences. Group 1 subtypes and group 2 subtypes are indicated in the schematic. The amino acid distance scale bar denotes a distance of 0.1.

We used a rapid single step cloning procedure to initially move the 3I14 Ab into the pcDNA3.1-Hinge scFvFc minibody expression vector, generating the scFv as a fusion product with the hinge, CH2, and CH3 domains of human IgG1[12]. Purified 3I14 scFvFc was used to assess the binding and neutralizing activity against multiple HAs and viruses of different subtypes (FIG. 1A-B and FIG. 2). For whole human IgG1s, the gene fragments of the scFv were separately subcloned into human IgG1 expression vector TCAE6[48]. The scFvFcs or IgG1s were expressed in 293F cells by transient transfection and purified by protein A sepharose affinity chromatography.

Kinetic and $K_d$ Determinations

We used a rapid single step cloning procedure to initially move the 3I14 Ab into the pcDNA3.1-Hinge scFvFc minibody expression vector, generating the scFv as a fusion product with the hinge, CH2, and CH3 domains of human IgG1[12]. Purified 3I14 scFvFc was used to assess the binding and neutralizing activity against multiple HAs and viruses of different subtypes (FIG. 1A-B and FIG. 2). For whole human IgG1s, the gene fragments of the scFv were separately subcloned into human IgG1 expression vector TCAE6[48]. The scFvFcs or IgG1s were expressed in 293F cells by transient transfection and purified by protein A sepharose affinity chromatography.

Microneutralization Assay

Prior to the experiment, MDCK cells ($1.5 \times 10^4$ cells per well) were seeded to the 96-well tissue culture plates and washed twice with PBS, then incubated in DMEM media supplemented with 2 µg/mL trypsin and 0.5% BSA. 100 $TCID_{50}$ (median tissue culture infectious doses) of virus were mixed in equal volume with two-fold serial dilutions of Ab or antibody containing supernatant in 96-well plates, and incubated for 1 h at 37° C. After the incubation, the Ab-virus mixture was transferred to confluent MDCK monolayers in duplicate, followed by incubation at 37° C. for 21 h. Cells were washed with PBS, fixed in 80% acetone, and viral antigen detected by indirect ELISA with a mAb against influenza A Virus Nucleoprotein (NP) (clone A3, BEI).

Prophylactic Studies in Mice

Twenty four hours before virus challenge inoculation groups of five female 8-10 weeks old BALB/c mice were injected with 3I14 and F10 IgG1 at low dose (5 mg kg$^{-1}$) or high dose (20 or 25 mg kg$^{-1}$) by intraperitoneal (i.p.) route in 0.5 mL volume, respectively. All groups of mice (n=6) were intranasally infected 10 $LD_{50}$ (median lethal dose) of A/Vietnam/1203/04 (H5N1), A/Brisbane/10/07-ma (H3N2), A/Netherlands/219/03 (H7N7) or A/Anhui/1/13 (H7N9). Mice were weighed on the day of virus challenge and then monitored for clinical signs and body weight recorded daily for 14 days or 18 days. Body weight loss of ≥25% relative to initial weight, or a score of 4 on clinical signs (unresponsiveness or severe neurological symptoms such as hind limb paralysis, ataxia) index were used as survival endpoints. Animal studies were conducted per approved Institutional Animal Care and Use Committee protocols.

Antibody Binding Competition

5 µg/ml H3-BR07 or H5-VN04 protein immobilized on ELISA plates were incubated with 2-fold serial dilution of 3I14 Fab, ranging from 80 nM to 0.3 nM and mixed with other scFvFc Abs at 5 nM. After co-incubation for 1 h, the binding of scFvFc Abs was detected using HRP-conjugated anti-human CH2 antibodies (Life Technologies, Grand Island, N.Y.) and measured using Super AquaBlue ELISA substrate (ebioscience, San Diego, Calif.) on the POLARstar Omega Microplate Reader (BMG LABTECH, Ortenberg, Germany).

Trypsin Cleavage Inhibition Assay 0.4 µg recombinant H3-histidine (H3-ATTH) protein was incubated in the presence of 2.5 µg 3I14 or anti-SARS Fm-6 IgG1, or in the absence of antibody in Tris-HCl buffer at pH 8.0 containing 100 µg ml$^{-1}$ Trypsin-ultra (New England Biolabs, Ipswich, Mass.) at 37° C. Trypsin digestion was inhibited at several time-points by addition of 1% BSA. Samples were run on 12% reduced SDS-PAGE gel under reducing conditions and blotted using a HisProbe-HRP and SuperSignal West HisProbe Kit (Pierce Biotechnology, Rockford, Ill.).

Conformational Change FACS Assay

293T/17 cells were transfected with full-length recombinant influenza A pcDNA3.1-H3-A2/68 and H3-BR07 plasmids. At ~30 hours after transfection, cells were detached from the culture vessel using 0.2% ethylenediaminetetraacetic acid (EDTA). To measure mAb binding to different HA structural conformations, cell samples were exposed to different treatments, aliquoted and stained with 3I14 or E730 scFvFc Abs. Detached cells consecutively treated with trypsin (Gibco, Grand Island, N.Y.) for 5 min at room temperature, washed with 1% BSA/PBS and incubated for 15 min in citric acid-sodium phosphate buffer pH 4.9, washed, and then incubated for 20 min with 50 mM dithiothreitol (DTT) in PBS at room temperature. Alternatively, 5 µg 3I14 or anti-SARS Ab Fm-6 IgG1 was added before the low pH step. Samples of consecutive treatments were stained with APC-conjugated anti-human Fc (BioLegend, San Diego, Calif.). Stained cells were analyzed using a BD FACSAria™ II with FACS Diva software (Becton Dickinson, Franklin Lakes, N.Y.).

Antibody-Dependent Cell Cytotoxicity Assay

The ADCC Reporter Bioassay uses engineered Jurkat cells stably expressing the FcγRIIIa receptor, V158 (high affinity) variant, and an NFAT response element driving expression of firefly luciferase as effector cells (Promega). Antibody biological activity in ADCC is quantified through the luciferase produced as a result of NFAT pathway activation; luciferase activity in the effector cell is quantified with luminescence readout. As target cells, $1 \times 10^4$/well H3- or H5-expressed 293T cells were attached to the flat bottom 96-well plates prior to assay, and the medium was then replaced with Low IgG Serum assay buffer (RPMI 1640 with 0.5% low IgG FBS). scFvFc antibodies were added to each well at 1, 0.2 and 0.04 µg ml$^{-1}$ final concentration. After one-hour, Jurkat effector cells were added for $6.0 \times 10^4$/well to assay plates in Low IgG Serum assay buffer and incubated for 6 hours. The supernatants were recovered by centrifugation at 300×g and measured using Bio-Glo™ Luciferase Assay kits (Promega, Madison, Wis.) at 490 nm by the POLARstar Omega Microplate Reader (BMG LABTECH, Ortenberg, Germany).

Figure 9B:
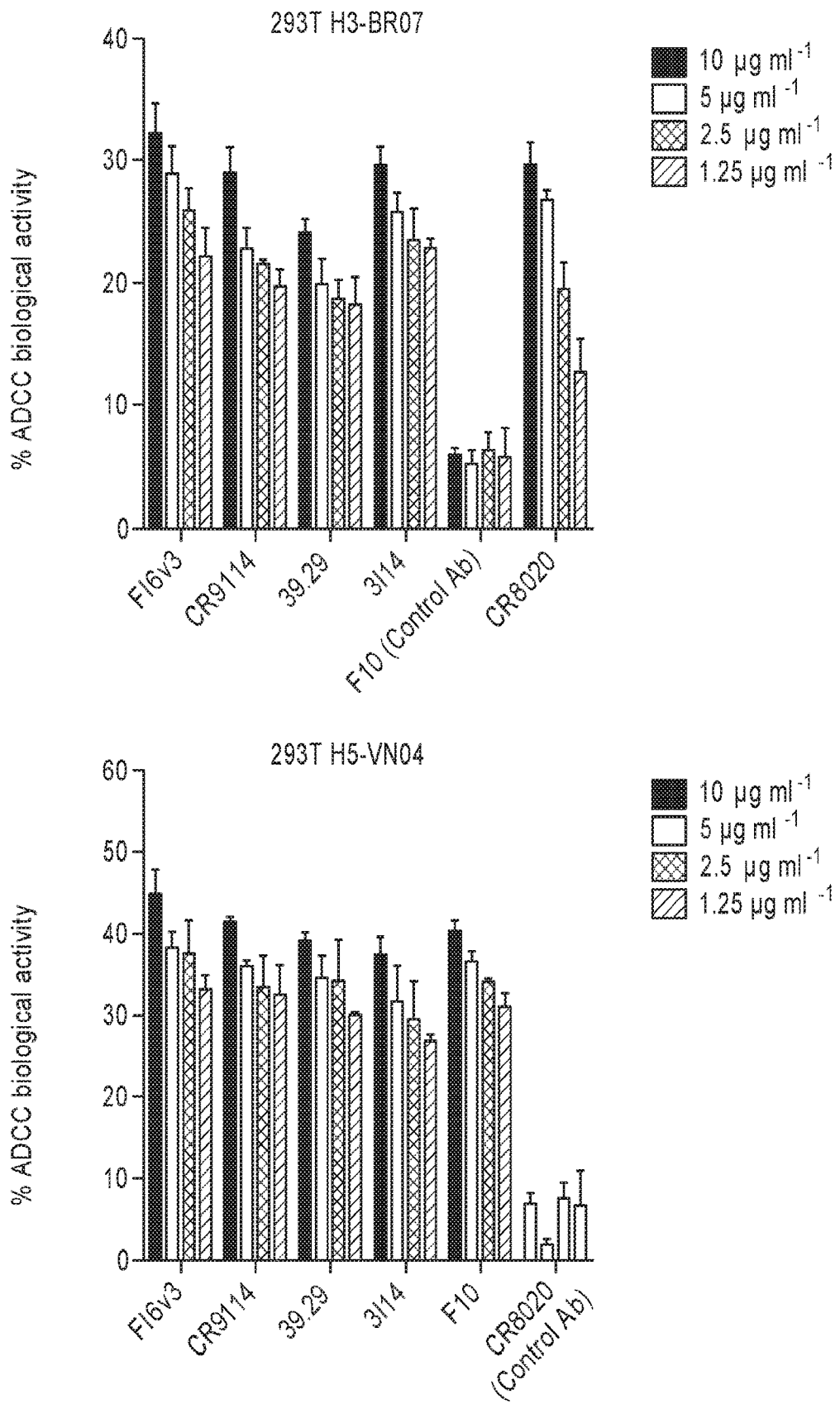

Additional ADCC methods for FIG. 9B are described forthwith. The ADCC assay was performed on HAs-expressed 293T cells with fresh PBMCs from healthy human donors. The ADCC activity was determined by a lactose dehydrogenase (LDH) release assay (Pierce Biotechnology, Rockford, Ill.). Fresh PBMCs as effector cells were isolated from the collected blood by use of the Ficoll-Paque gradient (GE HealthCare). As target cells, $2 \times 10^4$/well H3- or H5-expressed 293T cells were attached to the solid round bottom 96-well plates prior to assay, and the medium was then replaced with Low IgG Serum assay buffer (RPMI 1640 with 0.5% low IgG FBS). The scFvFc antibodies were added to each well at 10, 5, 2.5 and 1.25 µg ml$^{-1}$ final concentration. After one-hour, PBMCs were added for $1.2 \times 10^5$/well to assay plates in Low IgG Serum assay buffer and incubated for 6 hours. The supernatants were recovered by centrifugation at 300×g and measured using LDH Cytotoxicity Assay Kit (Pierce Biotechnology, Rockford, Ill.) at 490 nm and 680 nm by the Benchmark Plus Reader (Bio-Rad, Hercules, Calif.). The LDH activity was determined by subtracting the 680 nm absorbance value (background) from the 490 nm absorbance reading. The percent cytotoxicity was calculated as: % Cytotoxicity=100×(E−SE−ST)/(M−ST); E, released LDH from E/T culture with antibody; SE, spontaneous released LDH from effectors; ST, spontaneous released LDH from targets; M, the maximum released LDH from lysed targets. Data represent a representative experiment from three independent experiments, and all tests were performed in triplicate. Data represent a representative experiment from three independent experiments, and all tests were performed in triplicate.

Sequence Analysis

The full-length influenza A HA sequences were downloaded from the Influenza Virus Resource at the National Center for Biotechnology Information (NCBI) database. The Phylogenetic (PHYML) trees are based on their amino acid sequence comparison using Geneious software. The new bnAb, 3I14, was analyzed for germline gene usage, somatic mutations, N-nucleotides insertion and cognate variable heavy (VH) and light (VL) chain gene pairs using IMGT database (http://imgt.cines.fr). Antibody variants in which single or multiple germline mutations were reverted to the germline were produced by synthesis (Genewiz, South Plainfield, N.J.) and confirmed by sequencing. The VH and VK sequences of F10, FI6v3, CR9114, CR8020 and 39.29 were obtained through the Protein Data Bank (PDB accession code) and the corresponding genes were synthetized and expressed by transient transfection.

In Silico Structure Modeling

3I14 was homology modeled using the antibody-modeling module in BioLuminate. The model was superimposed to H3/F16 complex structure before docking with RosettaDock. Only high resolution docking is performed with side chain and loop rearrangement allowed. 1000 decoys were generated for each docking and clustered based on RMSD values. The final model was selected based on the cluster size and the criteria described in the result session.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated recombinantly produced monoclonal antibody that neutralizes an influenza virus comprising
   a. a heavy chain comprising a CDR1 comprising the amino acid sequence of SEQ ID NO: 7; a CDR2 comprising the amino acid sequence of SEQ ID NO: 8 and a CDR3 comprising the amino acid sequence of SEQ ID NO:9; and
   b. a light chain comprising a CDR1 comprising the amino acid sequence of SEQ ID NOs: 10; a CDR2 comprising the amino acid sequence of SEQ ID NO: 11; and a CDR3 comprising the amino acid sequence of SEQ ID NO: 12,
   wherein the antibody is a single chain Fv antibody.

2. The antibody according to claim 1, wherein said antibody binds to the stem region of HA of the influenza virus.

3. The antibody according to claim 1, wherein said influenza virus is an influenza A virus.

4. The antibody according to claim 1, wherein said antibody neutralizes influenza A virus Group I and Group II.

5. The antibody according to claim 1, wherein said antibody binds a conformational epitope defined by amino acids 18, 19, 20, 21, 36, 38, 39, 41, 42, 45, 46, 49 and 53 of an HA2 polypeptide, wherein the HA peptide comprises SEQ ID NO: 17.

6. The antibody according to claim 1, wherein the antibody is linked to a therapeutic agent.

7. The antibody of claim 6, wherein said therapeutic agent is a toxin, a radiolabel, a siRNA, a small molecule, or a cytokine.

8. A composition comprising the antibody of claim 1 and a carrier.

9. A method of preventing or treating an influenza virus infection in a subject, the method comprising administering to a person at risk of suffering from influenza virus infection, a therapeutically effective amount of the composition of claim 8.

10. The method of claim 9, further comprising administering an anti-viral agent.

* * * * *